US011007118B2

(12) United States Patent
Cowan et al.

(10) Patent No.: US 11,007,118 B2
(45) Date of Patent: May 18, 2021

(54) SYRINGE FILL ADAPTER

(71) Applicant: BAYER HEALTHCARE LLC, Whippany, NJ (US)

(72) Inventors: Kevin Cowan, Allison Park, PA (US); James A. Dedig, Pittsburgh, PA (US); Michael Spohn, Fenelton, PA (US); Michael McDermott, Pittsburgh, PA (US); Matthew McGee, Plymouth Meeting, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 140 days.

(21) Appl. No.: 15/778,350

(22) PCT Filed: Nov. 23, 2016

(86) PCT No.: PCT/US2016/063461

§ 371 (c)(1),
(2) Date: May 23, 2018

(87) PCT Pub. No.: WO2017/091643

PCT Pub. Date: Jun. 1, 2017

(65) Prior Publication Data

US 2018/0344571 A1 Dec. 6, 2018

Related U.S. Application Data

(60) Provisional application No. 62/259,906, filed on Nov. 25, 2015.

(51) Int. Cl.

*A61M 5/30* (2006.01)
*A61J 1/20* (2006.01)

(Continued)

(52) U.S. Cl.

CPC .......... *A61J 1/2096* (2013.01); *A61J 1/1406* (2013.01); *A61J 1/201* (2015.05); *A61J 1/2037* (2015.05);

(Continued)

(58) Field of Classification Search

CPC .......... A61M 5/30; A61M 37/00; A61M 5/32; A61B 19/00; B67D 7/60; B65D 5/72

See application file for complete search history.

(56) References Cited

U.S. PATENT DOCUMENTS 5,624,402 A * 4/1997 Imbert ................ A61M 5/3134 604/111
7,000,639 B2 * 2/2006 Butera ............... B60H 1/00564 137/829

(Continued)

FOREIGN PATENT DOCUMENTS

JP 2006061673 A 3/2006
JP 2007024159 A 2/2007

(Continued)

OTHER PUBLICATIONS

"International Search Report and Written Opinion from PCT Application No. PCT/US2016/063461", dated Apr. 10, 2018.

*Primary Examiner* — Tatyana Zalukaeva
*Assistant Examiner* — Ilya Y Treyger
(74) *Attorney, Agent, or Firm* — Joseph L. Kent; David Schramm; James R Stevenson

(57) ABSTRACT

A fill adapter for delivery of a medical liquid to a container has a body with a distal end, a proximal end, and a central bore extending between the distal end and the proximal end along a longitudinal axis. The central bore has an angled portion at the proximal end of the body such that a diameter of the central portion increases at the angled portion in a direction from the distal end to the proximal end. The fill adapter further has a flow controller disposed within the central bore at a distal end of the angled portion such that a gap is formed between an outer surface of the flow controller and an inner surface of the central bore. The flow controller is shaped to direct liquid flowing through the central bore to (Continued)

flow through the gap and along the angled portion of the central bore under a Coandă effect.

17 Claims, 43 Drawing Sheets

(51) Int. Cl.

| | |
|---|---|
| ***A61J 1/14*** | (2006.01) |
| *A61M 37/00* | (2006.01) |
| *A61M 5/32* | (2006.01) |
| *B67D 7/60* | (2010.01) |
| *B65D 5/72* | (2006.01) |

(52) U.S. Cl.

CPC ........... *A61J 1/2048* (2015.05); *A61J 1/2075* (2015.05); *A61J 1/2082* (2015.05)

(56) References Cited

U.S. PATENT DOCUMENTS

| | | | |
|---|---|---|---|
| 9,173,995 B1 | 11/2015 | Tucker et al. | |
| 2004/0186457 A1 | 9/2004 | Truitt et al. | |
| 2006/0149213 A1 | 7/2006 | Raybuck | |
| 2009/0050862 A1 * | 2/2009 | Cruce ..................... | E04H 17/00 256/8 |

FOREIGN PATENT DOCUMENTS

| | | | |
|---|---|---|---|
| JP | 2008502422 | A | 1/2008 |
| JP | 2012070929 | A | 4/2012 |
| JP | 2013028006 | A | 2/2013 |
| WO | 2005123159 | A2 | 12/2005 |
| WO | 2015164783 | A1 | 10/2015 |
| WO | WO 2017/083622 | * | 11/2015 |
| WO | 2016172467 | A1 | 10/2016 |

* cited by examiner

SYRINGE FILL ADAPTER

CROSS-REFERENCE TO RELATED APPLICATIONS

This application is a 371 national phase application of PCT International Application No. PCT/US2016/063461, filed Nov. 23, 2016, and claims priority to U.S. Provisional Patent Application No. 62/259,906, entitled "Syringe Fill Adapter" and filed on Nov. 25, 2015, the disclosure disclosures each of which are incorporated by reference herein in their entirety.

BACKGROUND OF THE DISCLOSURE

Field of the Disclosure

The present disclosure relates generally to syringes, fill adapters, and syringe and fluid transfer assemblies for use in fluid delivery systems, and, more particularly, to syringes, fill adapters, and syringe and fluid transfer assemblies for use in medical fluid delivery systems in which fluids are delivered to a patient under time constraints.

Description of the Related Art

In many medical procedures, such as drug delivery, it is desirable to inject a liquid into a patient. Numerous types of liquids, such as contrast media (often referred to simply as "contrast") and/or saline, may be injected into a patient during diagnostic and therapeutic procedures. In some medical procedures, for example, angiography, computed tomography (CT), ultrasound, magnetic resonance imaging (MRI), nuclear medicine, and positron emission tomography (PET), it is necessary to deliver a liquid, such as contrast, in a timed fashion under pressure. Injectors suitable for these applications typically use a relatively large volume syringe and are capable of producing relatively large flow rates.

Medical personnel work under increasingly difficult time and physical constraints. Thus, it is desirable to fill syringes or other liquid containers and to connect and disconnect fluid delivery systems as quickly as possible. However, filling a large syringe with liquid, such as contrast, is typically a time consuming process. Conventional syringes have a distal opening that is typically used for filling the interior of the syringe with liquid. The size of this distal opening places significant constraints on the filling rate. Further, since conventional syringes are typically shipped with the plunger in the fully retracted position, filling a syringe first requires moving the plunger to distal end of the syringe to eject air from the syringe and start the liquid filling process. Since the cost of many medical processes, such as diagnostic imaging, increases in relation to duration, any delays can significantly increase cost.

Furthermore, in many such fluid delivery systems, it is necessary to form a fluid connection between separate fluid path components. For example, it may be necessary to connect an injector-powered syringe to flexible plastic tubing that, in turn, is connected to a catheter inserted into a patient. A common connector used in the medical arts is the luer connector or luer lock. The luer connector includes a male connector or member and a female connector or member. The male member and female member are typically connected via radially inwardly projecting threading attached to the female member, which cooperates with one or more radially outwardly extending flanges on the male luer member to create a leak-free connection.

Medical personnel must connect and/or disconnect fluid delivery elements in a relatively short time and under stressed and/or emergency conditions. It is thus desirable to develop syringe adapters that are configured for filling a syringe and that have durable syringe and connector interfaces capable of connecting or disconnecting simply and quickly.

SUMMARY OF THE DISCLOSURE

In general, the present disclosure relates to syringes and fill adapters used in fluid transfer assemblies for medical fluid delivery systems.

In accordance with some examples of the present disclosure, a fill adapter for delivery of a medical fluid to a container may have a body having a distal end, a proximal end, and a central bore extending between the distal end and the proximal end along a longitudinal axis. The central bore may have an angled portion at the proximal end of the body such that a diameter of the central portion increases at the angled portion in a direction from the distal end to the proximal end. The fill adapter may further have a flow controller disposed within the central bore at a distal end of the angled portion such that a gap is formed between an outer surface of the flow controller and an inner surface of the central bore. The flow controller may be shaped to direct fluid flowing through the central bore to flow through the gap and along the angled portion of the central bore under a Coandă effect.

In accordance with other examples of the present disclosure, at least a portion of the flow controller may be connected to the inner surface of the central bore by one or more spokes. Each of the one or more spokes may have a first end connected to the inner surface of the central bore and a second end connected to the flow controller. Each of the one or more spokes may be resiliently elastic such that the flow controller is movable in a direction of the longitudinal axis of the body with the flow of the liquid. The flow controller may have a curved distal surface. The curved distal surface of the flow controller may be convex. The curved distal surface may have a flow diverter extending distally from a central portion of the curved distal surface. The flow diverter may be shaped to direct fluid flowing through the central bore in a radially outward direction toward the gap. The flow controller may have a curved proximal surface. The curved proximal surface of the flow controller may be convex. The body may have a flange at the distal end, the flange extending radially outward relative to an outer surface of the body. At least a portion of the body may be configured to be removably received within an open distal end of the container.

In accordance with other examples of the present disclosure, a fluid transfer assembly may have a syringe for receiving a medical liquid therein, and a fill adapter. The syringe may have a proximal end, a distal end having an open-ended syringe neck, and a sidewall extending between the proximal end and the distal end along a longitudinal axis. The syringe may define an interior volume for receiving the medical liquid therein. The fill adapter may be received within the open-ended syringe neck. The fill adapter may have a body having a distal end, a proximal end, and a central bore extending between the distal end and the proximal end along a longitudinal axis. The central bore may have an angled portion at the proximal end of the body such that a diameter of the central portion increases at the angled portion in a direction from the distal end to the proximal end. The fill adapter may further have a flow controller disposed within the central bore at a distal end of the angled portion such that a gap is formed between an outer surface of the flow controller and an inner surface of the central bore. The flow controller may be shaped to direct liquid flowing through the central bore to flow through the gap and along the angled portion of the central bore under a Coandă effect.

In accordance with other examples of the present disclosure, an outer portion of the syringe neck may have a flange extending around at least a portion of a circumference of the syringe neck. At least a portion of the flange may be configured to engage a cap for enclosing the distal end of the syringe. The syringe may have a drive member engagement portion protruding proximally from an end wall enclosing the proximal end and configured for engagement with a drive member of a fluid injector. The sidewall of the syringe may be flexible and roll upon itself when acted upon by a drive member of a fluid injector such that an outer surface of the sidewall is folded in a radially inward direction as the drive member is advanced from the proximal end to the distal end and wherein the outer surface of the sidewall is unfolded in a radially outward direction as the drive member is retracted from the distal end to the proximal end. At least a portion of the flow controller may be connected to the inner surface of the central bore by one or more spokes. Each of the one or more spokes may have a first end connected to the inner surface of the central bore and a second end connected to the flow controller. The flow controller may have a curved distal surface.

In accordance with other examples of the present disclosure, a fluid transfer assembly may have a syringe for receiving a medical liquid therein, the syringe having a proximal end, a distal end having an open-ended syringe neck, and a sidewall extending between the proximal end and the distal end along a longitudinal axis. The syringe may define an interior volume for receiving the medical liquid therein. The fluid transfer assembly may further have a fill adapter received within the open-ended syringe neck. The fluid transfer assembly may further have a cap secured to the syringe neck, the cap having a nozzle in fluid communication with the interior volume of the rolling diaphragm syringe. The fill adapter may have a body with a distal end, a proximal end, and a central bore extending between the distal end and the proximal end along a longitudinal axis. The central bore may have an angled portion at the proximal end of the body such that a diameter of the central portion increases at the angled portion in a direction from the distal end to the proximal end. The fill adapter may further have a flow controller disposed within the central bore at a distal end of the angled portion such that a gap is formed between an outer surface of the flow controller and an inner surface of the central bore. The flow controller may be shaped to direct liquid flowing through the central bore to flow through the gap and along the angled portion of the central bore under a Coandă effect. An outer portion of the syringe neck may have a flange extending around at least a portion of a circumference of the syringe neck, and the cap may have one or more tabs configured to releasably engage at least a portion of the flange. The one or more tabs may have a first end connected to the cap and a second end extending proximally from the first end. The second end may be deflectable in a radially outward direction when the cap contacts the flange on the syringe neck.

Various other aspects of the present disclosure are recited in one or more of the following clauses:

Clause 1: A fill adapter for delivery of a medical liquid to a container, the fill adapter comprising: a body having a distal end, a proximal end, and a central bore extending between the distal end and the proximal end along a longitudinal axis, the central bore having an angled portion at the proximal end of the body such that a diameter of the central portion increases at the angled portion in a direction from the distal end to the proximal end; and a flow controller disposed within the central bore at a distal end of the angled portion such that a gap is formed between an outer surface of the flow controller and an inner surface of the central bore, wherein the flow controller is shaped to direct liquid flowing through the central bore to flow through the gap and along the angled portion of the central bore under a Coandă effect.

Clause 2: The fill adapter of clause 1, wherein at least a portion of the flow controller is connected to the inner surface of the central bore by one or more spokes having a first end connected to the inner surface of the central bore and a second end connected to the flow controller.

Clause 3: The fill adapter of clause 2, wherein each of the one or more spokes is resiliently elastic such that the flow controller is movable in a direction of the longitudinal axis of the body with the flow of the liquid.

Clause 4: The fill adapter of any of clauses 1-3, wherein the flow controller has a curved distal surface.

Clause 5: The fill adapter of clause 4, wherein the curved distal surface of the flow controller is convex.

Clause 6: The fill adapter of clause 4, wherein the curved distal surface has a flow diverter extending distally from a central portion of the curved distal surface, the flow diverter shaped to direct liquid flowing through the central bore in a radially outward direction toward the gap.

Clause 7: The fill adapter of any of clauses 1-6, wherein the flow controller has a curved proximal surface.

Clause 8: The fill adapter of clause 7, wherein the curved proximal surface of the flow controller is convex.

Clause 9: The fill adapter of any of clauses 1-8, wherein the body has a flange at the distal end, the flange extending radially outward relative to an outer surface of the body.

Clause 10: The fill adapter of any of clauses 1-9, wherein at least a portion of the body is configured to be removably received within an open distal end of the container.

Clause 11: A fluid transfer assembly comprising: a syringe for receiving a medical liquid therein, the rolling diaphragm syringe comprising: a proximal end, a distal end having an open-ended syringe neck, and a sidewall extending between the proximal end and the distal end along a longitudinal axis, the syringe defining an interior volume for receiving the medical liquid therein; and a fill adapter received within the open-ended syringe neck, the fill adapter comprising: a body having a distal end, a proximal end, and a central bore extending between the distal end and the proximal end along a longitudinal axis, the central bore having an angled portion at the proximal end of the body such that a diameter of the central portion increases at the angled portion in a direction from the distal end to the proximal end; and a flow controller disposed within the central bore at a distal end of the angled portion such that a gap is formed between an outer surface of the flow controller and an inner surface of the central bore, wherein the flow controller is shaped to direct liquid flowing through the central bore to flow through the gap and along the angled portion of the central bore under a Coandă effect.

Clause 12: The fluid transfer assembly of clause 11, wherein an outer portion of the syringe neck has a flange extending around at least a portion of a circumference of the syringe neck.

Clause 13: The fluid transfer assembly of any of clauses 11-12, wherein at least a portion of the flange is configured to engage a cap for enclosing the distal end of the syringe.

Clause 14: The fluid transfer assembly of any of clauses 11-13, wherein the syringe has a drive member engagement portion protruding proximally from an end wall enclosing the proximal end and configured for engagement with a drive member of a liquid injector.

Clause 15: The fluid transfer assembly of any of clauses 11-14, wherein the sidewall of the syringe is flexible and rolls upon itself when acted upon by a drive member of a liquid injector such that an outer surface of the sidewall is folded in a radially inward direction as the drive member is advanced from the proximal end to the distal end and wherein the outer surface of the sidewall is unfolded in a radially outward direction as the drive member is retracted from the distal end to the proximal end.

Clause 16: The fluid transfer assembly of any of clauses 11-15, wherein at least a portion of the flow controller is connected to the inner surface of the central bore by one or more spokes, and wherein each of the one or more spokes has a first end connected to the inner surface of the central bore and a second end connected to the flow controller.

Clause 17: The fluid transfer assembly of any of clauses 11-16, wherein the flow controller has a curved distal surface.

Clause 18: A fluid transfer assembly comprising: a syringe for receiving a medical liquid therein, the rolling diaphragm syringe comprising: a proximal end, a distal end having an open-ended syringe neck, and a sidewall extending between the proximal end and the distal end along a longitudinal axis, the syringe defining an interior volume for receiving the medical liquid therein; a fill adapter received within the open-ended syringe neck, the fill adapter comprising: a body having a distal end, a proximal end, and a central bore extending between the distal end and the proximal end along a longitudinal axis, the central bore having an angled portion at the proximal end of the body such that a diameter of the central portion increases at the angled portion in a direction from the distal end to the proximal end; and a flow controller disposed within the central bore at a distal end of the angled portion such that a gap is formed between an outer surface of the flow controller and an inner surface of the central bore; and a cap secured to the syringe neck, the cap having a nozzle in fluid communication with the interior volume of the rolling diaphragm syringe, wherein the flow controller is shaped to direct liquid flowing through the central bore to flow through the gap and along the angled portion of the central bore under a Coandă effect.

Clause 19: The fluid transfer assembly of clause 18, wherein an outer portion of the syringe neck has a flange extending around at least a portion of a circumference of the syringe neck, and wherein the cap has one or more tabs configured to releasably engage at least a portion of the flange.

Clause 20: The fluid transfer assembly of clause 19, wherein the one or more tabs has a first end connected to the cap and a second end extending proximally from the first end, and wherein the second end is deflectable in a radially outward direction when the cap contacts the flange on the syringe neck.

These and other features and characteristics of the syringes, fill adapter, and syringe and fluid transfer assembly for use in medical fluid delivery systems and combination of parts and economies of manufacture will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure.

DETAILED DESCRIPTION OF THE DISCLOSURE

Figure 2A:
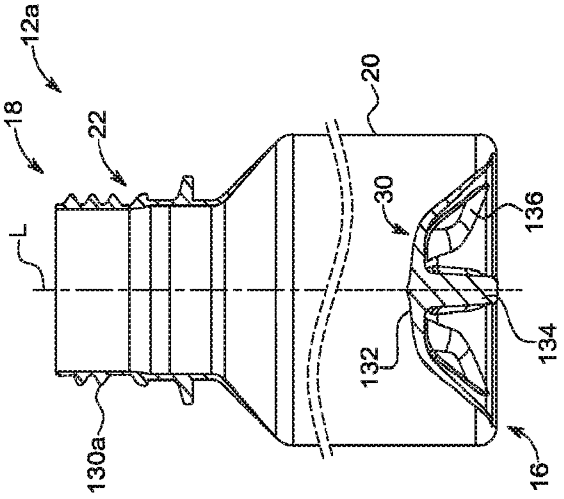
FIG. 2A is a side cross-sectional view of a syringe for use with a fill adapter in accordance with one example of the present disclosure.

The illustrations generally show non-limiting examples of the present disclosure. While the description presents various examples, it should not be interpreted in any way as limiting the disclosure. Furthermore, modifications, concepts, and applications of the disclosure's examples are to be interpreted by those skilled in the art as being encompassed, but not limited to, the illustrations and description provided herein. Any and all such modifications, variations, equivalents, and alternatives are intended to fall within the spirit and scope of the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures. When used in relation to a syringe, the term "proximal" refers to a portion of a syringe nearest to an injector when a syringe is oriented for connecting to an injector. The term "distal" refers to a portion of a syringe farthest away from an injector when a syringe is oriented for connecting to an injector. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of a syringe extending between the proximal and distal ends. The term "flexible", when used in connection with a syringe, means that at least a portion of a syringe, such as a sidewall of a syringe, is capable of bending or being bent to change a direction in which it extends. The terms "roll over", "rolling over", and "rolls upon itself" refer to an ability of a first portion of a syringe, such as a proximal portion of a sidewall of a syringe, to bend approximately 180° relative to a second portion of a syringe, such as a distal portion of a sidewall of a syringe, when urged by a drive member of a fluid injector.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

It is to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

All documents, such as but not limited to issued patents and patent applications, referred to herein, and unless otherwise indicated, are to be considered to be "incorporated by reference" in their entirety.

Referring to the drawings in which like reference characters refer to like parts throughout the several views thereof, syringes, fill adapters, and syringe and fluid transfer assemblies for use in medical fluid delivery systems will be described herein in detail. The present disclosure also provides other connectors suitable for use with the syringes disclosed herein, as well as with other fluid path elements or fluid pumping systems. In general, the connectors of the present disclosure are suitable for use in low-pressure and high-pressure fluid injection systems.

With reference to FIG. 1 and FIGS. 3A-11, a fluid transfer assembly 10 for delivery of medical liquids is illustrated in accordance with one example. The fluid transfer assembly 10 is configured to facilitate transfer of liquid from a second liquid container 36 to a first liquid container 12. In some examples, the first liquid container 12 and/or the second liquid container 36 may be a syringe, vial, bottle, bag, or other containment structure configured for receiving a volume of liquid therein. In some examples, the first liquid container 12 may be a syringe, while the second liquid container 36 may be a bulk-liquid storage container, such as a bottle or a bag.

Figure 1:
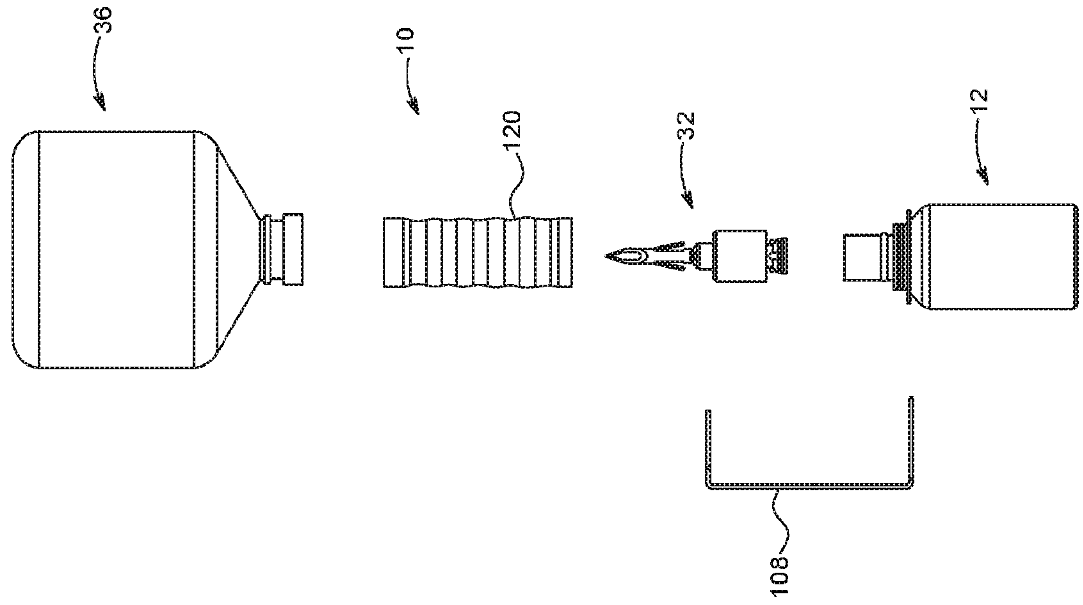
FIG. 1 is an exploded side view of a syringe and fluid transfer assembly in accordance with one example of the present disclosure.

With continued reference to FIG. 1, the fluid transfer assembly 10 further includes a fill adapter 32 configured for facilitating a transfer of liquid between the two liquid containers, such as from the second liquid container 36 to the first liquid container 12. The fill adapter 32 may be removably connectable to the first liquid container 12 and/or the second liquid container 36. In some examples, the fill adapter 32 may be non-removably connected to one of the first liquid container 12 and the second liquid container 36, and be removably connectable to the other of the first liquid container 12 and the second liquid container 36. The fill adapter 32 may have a unitary, single piece structure, or it may be formed from two or more components removably or non-removably coupled together.

The fill adapter 32 may be configured for operation between a first state and a second state. In the first state, liquid flow may be obstructed such that no liquid can be transferred between the two liquid containers, such as from the second liquid container 36 to the first liquid container 12. In the second state, liquid may flow between the two liquid containers, such as from the second liquid container 36 to the first liquid container 12 through the fill adapter 32. As described herein, the fill adapter 32 may be movable between a first position and a second position to affect operation between the first and second states, respectively.

Figure 3A:
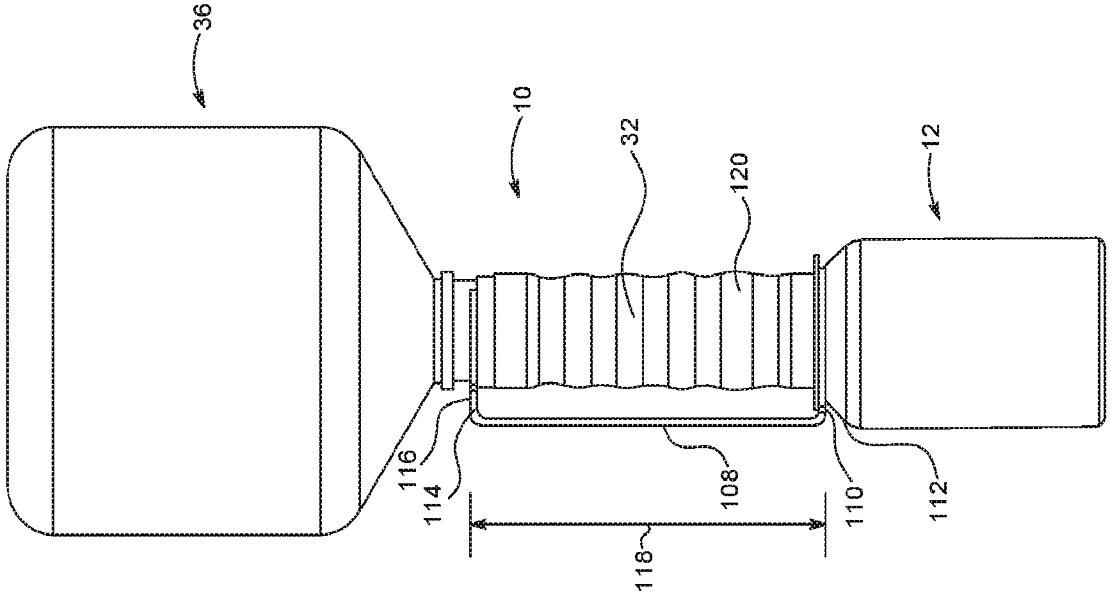
FIG. 3A is a side view of the syringe and fluid transfer assembly of FIG. 1.
Figure 3B:
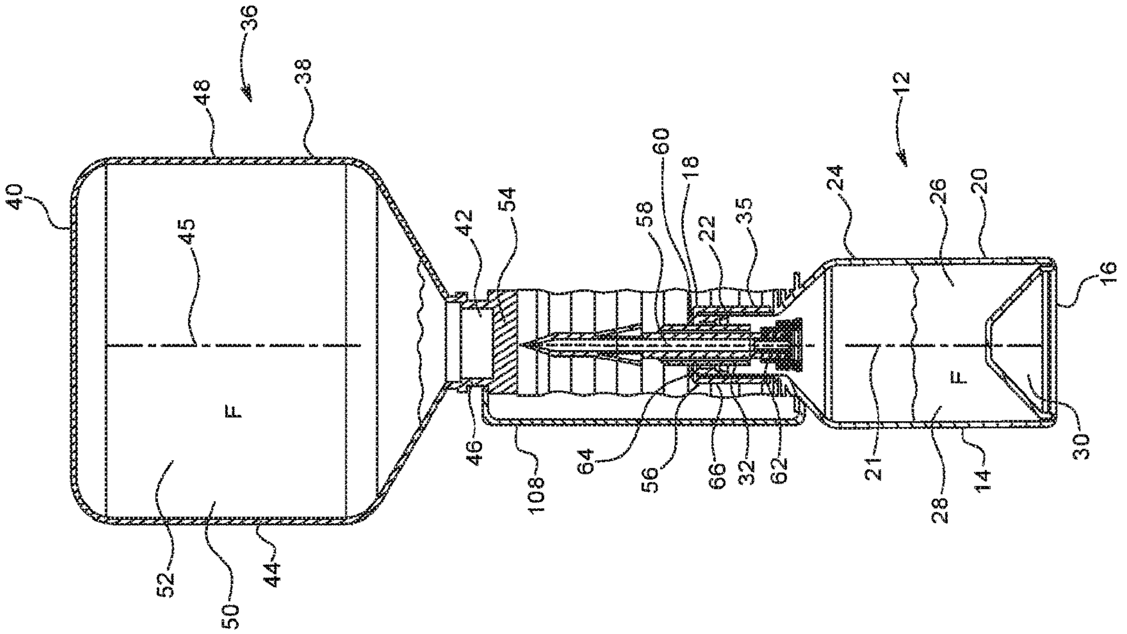
FIG. 3B is a longitudinal cross-sectional view of FIG. 3A.

With reference to FIG. 1 and FIGS. 3A-3B, the fluid transfer assembly 10 may have a locking mechanism 108 removably connectable to at least two of the first liquid container 12, the fill adapter 32, and the second liquid container 36. The locking mechanism 108 may be configured for preventing movement of the components of the fluid transfer assembly 10 between the first position and the second position in order to prevent the flow of liquid between the two containers, such as from the second liquid container 36 to the first liquid container 12. The locking mechanism 108 may be a bracket that is removable from the fluid transfer assembly 10, or it may be movable from a first position to a second position. In the first position, the locking mechanism 108 may prevent activation of the fill adapter 32 from the first state to the second state, thereby preventing liquid from flowing from the second liquid container 36 to the first liquid container 12. In the second position, the locking mechanism 108 may enable the fill adapter 32 to be activated in the second state, thereby allowing liquid to flow from the second liquid container 36 to the first liquid container 12.

With reference to FIG. 2A, a non-limiting example of the first liquid container 12 is shown as a rolling diaphragm syringe **12*a* having a flexible sidewall. The rolling diaphragm syringe 12*a* may be used as the first liquid container in any example of the present disclosure described with reference to FIGS. 3A-33C. The rolling diaphragm syringe 12*a* is adapted for use in CT, MRI, PET, and like procedures and operable at typical operating pressures of, for example, about 10-300 psi, such as 200-300 psi, depending on the viscosity of the liquid and the desired rate of injection. In some examples, the rolling diaphragm syringe 12*a* may be configured for use in procedures requiring pressures on the order of 1,200 psi, such as used in angiography. In some aspects, the rolling diaphragm syringe 12*a*** may be a syringe disclosed in International Patent Application No. PCT/US2015/027582 and/or International Patent Application No. PCT/US2016/028824, the disclosures of which are incorporated herein by reference.

With continued reference to FIG. 2A, the rolling diaphragm syringe **12*a* generally includes a hollow body that includes a forward or distal end 18, a rearward or proximal end 16, and a flexible sidewall 20 extending therebetween along a longitudinal axis L. In use, the proximal end 16 is configured for insertion into a throughbore of a pressure jacket attached to a liquid injector such that the sidewall 20 is surrounded by the interior surface of the pressure jacket. At least a portion of the distal end 18 of the rolling diaphragm syringe 12***a* may be exposed from the distal end 18 of the pressure jacket. In some examples, the rolling diaphragm syringe 12*a* may be formed using a blow-molding technique. In other examples, the rolling diaphragm syringe 12*a* may be injection molded.

With continued reference to FIG. 2A, the proximal end 16 of the syringe 12*a* connects to a closed end wall 30, and the distal end 18 of the rolling diaphragm syringe 12*a* defines a syringe neck 22 opposite the closed end wall 30. The distal end 18 may have a frusto-conical shape that gradually narrows from the sidewall 20 to the syringe neck 22. The syringe neck 22 is open to allow liquid to be introduced into and/or delivered from the syringe interior. The closed end wall 30 may be shaped to interface directly or indirectly with a drive member of a liquid injector (not shown). For example, the closed end wall 30 may define a receiving end pocket for interfacing directly with a similarly-shaped drive member, which may be shaped to substantially match the shape of the closed end wall 30. The sidewall 20 and/or the end wall 30 may have uniform or non-uniform thickness. For example, the sidewall 20 may have increased thickness at the distal end 18 compared to the end wall 30.

The sidewall 20 of the rolling diaphragm syringe 12*a* defines a soft, pliable or flexible, yet self-supporting body that is configured to roll upon itself under the action of the drive member. In particular, the sidewall 20 of the rolling diaphragm syringe 12*a* is configured to roll upon itself such that its outer surface is folded and inverted in a radially inward direction as the drive member is moved in a distal direction, and unroll and unfold in the opposite manner in a radially outward direction as the drive member is retracted in a proximal direction.

The rolling diaphragm syringe 12*a* may be made of any suitable medical-grade plastic or polymeric material, desirably a clear or substantially translucent plastic material, such as, but not limited to, polypropylene random copolymer, polypropylene impact copolymer, polypropylene homopolymer, polypropylene, polyethylene terephthalate, POM, ABS, HPDE, nylon, cyclic olefin copolymer, multilayer polypropylene, polycarbonate, ethylene vinyl acetate, polyethylene, and the like. The material of the rolling diaphragm syringe 12*a* is desirably selected to meet the required tensile and planar stress requirements, water vapor transmission, and chemical/biological compatibility.

The distal end 18 of the rolling diaphragm syringe 12*a*, such as the syringe neck 22, may have a connection member 130*a* at the distal end 18 for connecting to a corresponding cap member, for example at least a portion of the fill adapter 32 described herein. In some aspects, the connection member 130*a* is a threaded interface having one or more threads for mating with corresponding threads on the fill adapter 32. In certain aspects, the connection member 130*a* may be configured to connect with the fill adapter 32 by way of luer-type connection. In other aspects, the connection member 130*a* may have one or more lips or grooves that interact with corresponding grooves or lips on the fill adapter 32 to releasably or non-releasably retain the rolling diaphragm syringe 12*a* with the fill adapter 32. The connection between the fill adapter 32 and the syringe 12*a* may have at least one seal, such as an O-ring seal, to prevent liquid leakage at a connection interface between the fill adapter 32 and the syringe 12*a*. The syringe neck 22 may also be configured for fluid connection with a liquid path set (not shown) that may be connected to the patient. In some examples, the liquid path set may be in the form of tubing configured for delivering liquid from the first liquid container 12 to the patient or a container for receiving the liquid. In some examples, the liquid path set is removably connectable with the syringe neck 22 of the first liquid container 12.

The end wall 30 may have a central portion 132 having a substantially dome-shaped structure and a drive member engagement portion 134 extending proximally from the central portion 132, such as from an approximate midpoint of the central portion 132. In some aspects, a distal most end of the central portion 132 may be substantially flat. The drive member engagement portion 134 is configured for engagement with the engagement mechanism on the drive member of the liquid injector. The proximal end 16 of the rolling diaphragm syringe 12*a* may have one or more ribs 136 protruding radially outward from the drive member engagement portion 134 along a proximal surface of the central portion 132. In certain embodiments, rolling diaphragm syringe 12*a* may be originally in the compressed, rolled configuration when engaged with the injector and the drive member may engage the drive member engagement portion 134 to retract the end wall 30, unrolling the sidewall 20, to allow filling of the syringe interior.

Figure 2B:
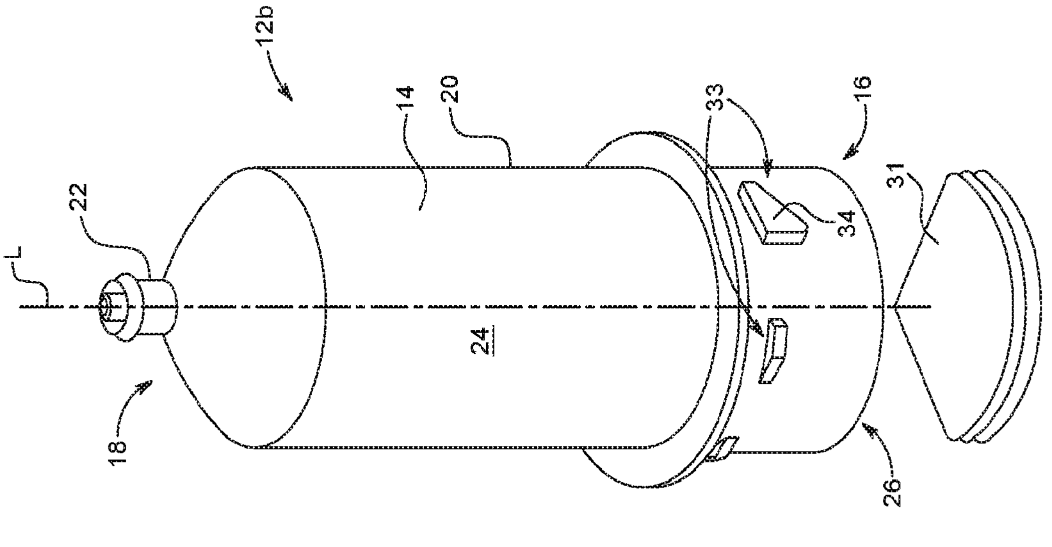
FIG. 2B is a perspective view of a syringe for use with a fill adapter in accordance with another example of the present disclosure.
Figure 4:
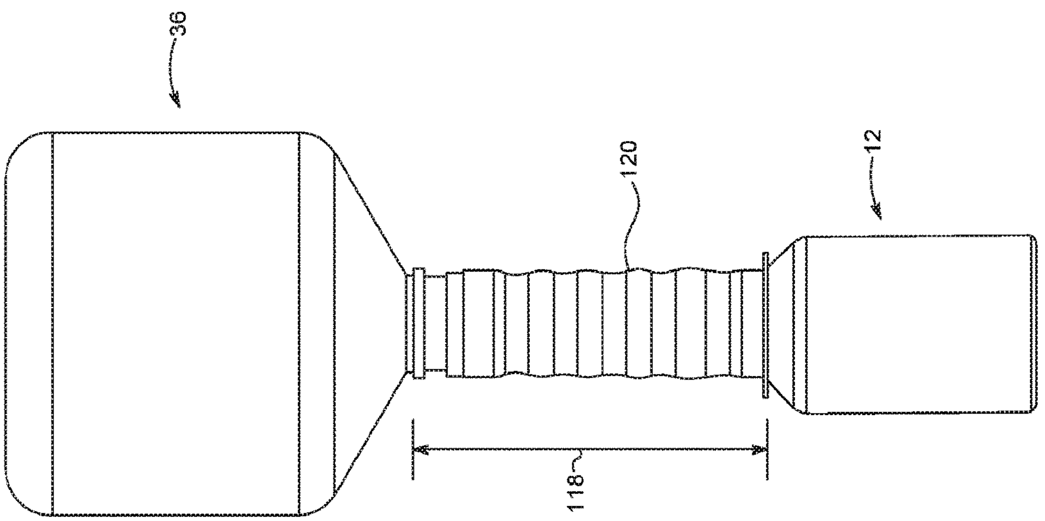
FIG. 4 is a side view of the syringe and fluid transfer assembly of FIG. 3A in a first engagement position.

With reference to FIG. 2B, a non-limiting example of the first liquid container 12 is shown as a syringe 12*b* having a substantially rigid sidewall. The syringe 12*b* may be used as the first liquid container in any example of the present disclosure described with reference to FIGS. 3A-33C. The syringe 12*b* is adapted for use in CT, MRI, PET, and like procedures and operable at typical operating pressures of, for example, about 10-300 psi, such as 200-300 psi, depending on the viscosity of the liquid and the desired rate of injection. In some examples, the syringe 12*b* may be configured for use in procedures requiring pressures on the order of 1,200 psi, such as used in angiography. In some aspects, the syringe 12*b* may be a syringe disclosed in U.S. Pat. No. 9,173,995, the disclosure of which is incorporated herein by reference in its entirety.

The syringe 12*b* generally has a cylindrical syringe barrel 14 formed from glass, metal, a suitable medical-grade plastic, or a combination thereof. The barrel 14 has a proximal end 16 and a distal end 18, with a sidewall 20 extending therebetween along a length of a longitudinal axis L. A syringe neck 22 extends from the distal end 18 of the barrel 14. The barrel 14 has an outer surface 24 and an inner surface 26 that defines an interior volume configured for receiving the liquid therein. The proximal end 16 of the barrel 14 may be sealed with a plunger 31 that is slidable through the barrel 14. The plunger 31 forms a liquid-tight seal against the inner surface 26 of the sidewall 20 of the barrel 14 as it is advanced or retracted therethrough. The plunger 31 may have a rigid inner element configured for engagement with a drive member of a liquid injector (not shown). The plunger 31 may further include an elastomeric cover disposed over at least a portion of the rigid inner element. The elastomeric cover is configured to engage the inner surface 26 of the barrel 14 and provide the liquid-tight seal against the inner surface of the sidewall 20 of the barrel 14.

With continued reference to FIG. 2B, the proximal end 16 of the syringe 12*b* is sized and adapted for being removably inserted in a syringe port of the injector. In some examples, the proximal end 16 of the syringe 12*b* defines an insertion section that is configured to be removably inserted into the syringe port of the injector 10 while the remaining portion of the syringe 12*b* remains outside of the syringe port.

In certain examples, the proximal end 16 of the syringe 12*b* includes one or more syringe retaining members 33 adapted to form a locking engagement with a corresponding locking mechanism in the syringe port of the injector for releasably retaining the syringe 12*b* in the syringe port. The combination of the syringe 12*b* having the one or more syringe retaining members 33 and the locking mechanism of the injector defines a connection interface for loading and unloading the syringe 12*b* to and from the injector. In some examples, at least a portion of the one or more syringe retaining members 33 may cooperate with at least a portion of the locking mechanism to self-orient the syringe 12*b* relative to the syringe port such that the syringe 12*b* may be releasably inserted into and locked with the syringe port. The one or more syringe retaining members 33 may be formed as one or more lugs 34 that protrude radially outwardly from the outer surface 24 of the syringe barrel 14 relative to the longitudinal axis L. In some examples, a plurality of lugs 34 may be separated radially about the circumference of the barrel 14. In such examples, the lugs 34 are separated from each other by portions of the outer surface 24 of the barrel 14. Each of the one or more lugs 34 may have a generally triangular, rectangular, polygonal, or arrowhead shape.

With reference to FIG. 3A, the locking mechanism 108 may be a "U"-shaped bracket with a mount 110 at a first end 112 adapted to connect to the first liquid container 12, and a mount 114 at a second end 116 adapted to connect to the second liquid container 36. The length of the middle portion 118 of the locking mechanism 108, defined as the length between the first end 112 and the second end 116, is longer than a longitudinal length of the fill adapter 32, so that when the locking mechanism 108 is secured to both the first liquid container 12 and the second liquid container 36 the fill adapter 32 will be in a first engagement position (i.e., engaged with only the first liquid container 12 and not engaged with the second liquid container 36).

The fluid transfer assembly 10 may further include a flexible shroud 120, made from any durable and flexible material such as rubber, to enclose and protect the fill adapter 32. The flexible shroud 120 may be collapsible or compressible to accommodate movement of the fill adapter 32 from the first position to the second position.

With reference to FIG. 3B, the second liquid container 36 may have a cylindrical barrel 38 formed from glass, metal, a suitable medical-grade plastic, or a combination thereof or may be a plastic bag, such as a saline bag. The barrel 38 has a proximal end 40 and a distal end 42, with a sidewall 44 extending therebetween along a longitudinal axis 45. A liquid delivery section, such as a neck 46, extends from the distal end 42 of the barrel 38. The barrel 38 has an outer surface 48 and an inner surface 50 that defines an interior volume 52 configured for receiving a liquid F therein. The distal end 42 of the second liquid container 36 may include a connection interface for connecting with the fill adapter 32. In some examples, the distal end 42 may be enclosed by a piercable septum 54. The fill adapter 32 may be configured to pierce through the septum 54 to connect the interior volume 52 of the second liquid container 36 with the interior volume 28 of the first liquid container 12 to facilitate transfer of liquid F from the second liquid container 36 to first liquid container 12.

With continued reference to FIG. 3B, the fill adapter 32 has a generally cylindrical body 56 formed from glass, metal, a suitable medical-grade plastic, or a combination thereof. The body 56 has a longitudinal axis 58, a distal end 60, and a proximal end 62. The distal end 60 is configured for engaging the second liquid container 36 to establish fluid connection between the second liquid container 36 and the fill adapter 32. The proximal end 62 is configured for engaging the first liquid container 12 to establish fluid connection between the first liquid container 12 and the fill adapter 32. In some examples, the proximal end 62 of the body 56 is configured to releasably connect to the syringe neck 22.

The body 56 of the fill adapter 32 is desirably hollow to allow a passage of liquid therethrough. In some examples, the body 56 has an inner sidewall 64 and an outer sidewall 66 extending between the distal end 60 and the proximal end 62 along the longitudinal axis 58. In some examples, the inner sidewall 64 may be configured to interface with the inner surface 26 of the syringe neck 22 while the outer sidewall 66 is configured to interface with the outer surface 24 of the syringe neck 22. The groove 35, configured to engage the tabbed portion 34 located on the outer surface 24 of syringe neck 22, is formed on outer sidewall 64.

Figure 6:
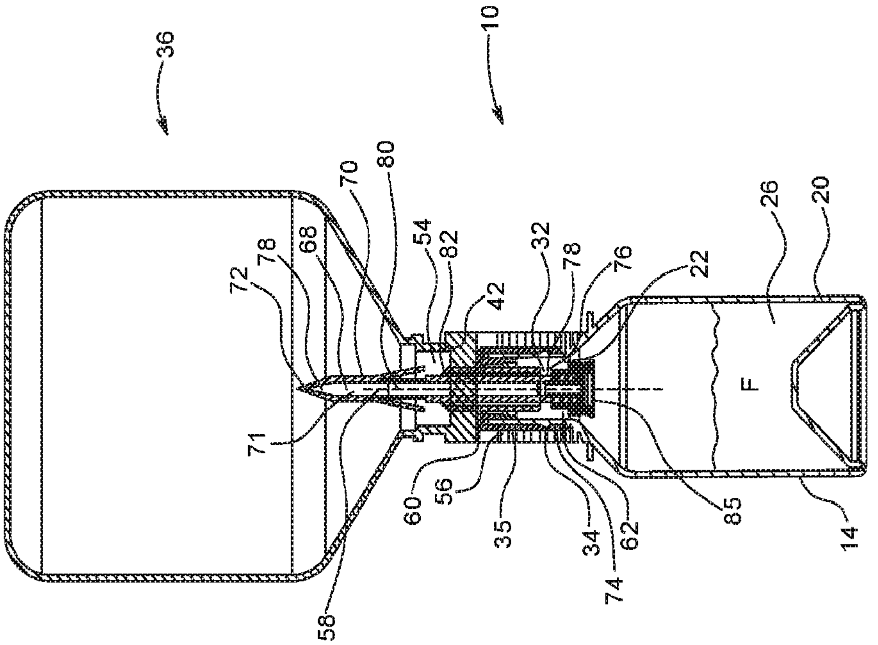
FIG. 6 is a longitudinal cross-sectional view of FIG. 5.
Figure 5:
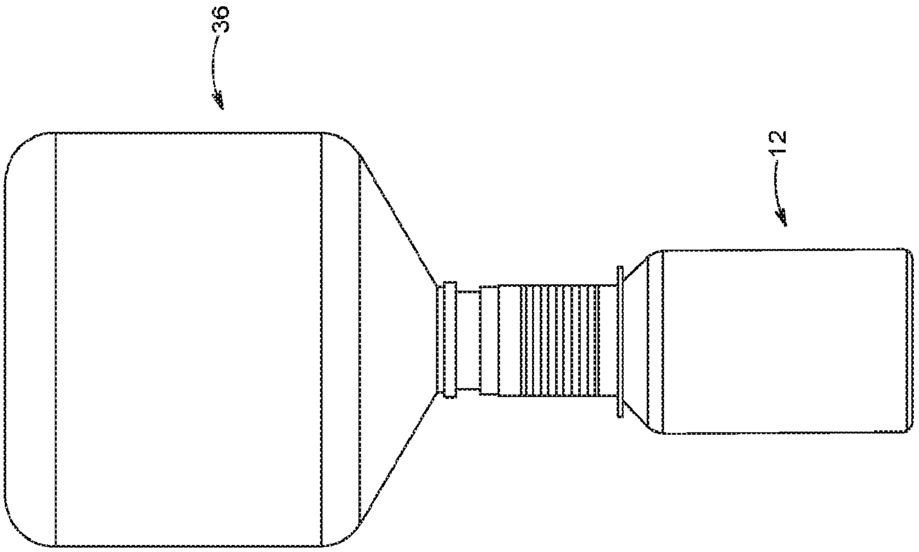
FIG. 5 is a side view of the syringe and fluid transfer assembly of FIG. 3A in a second engagement position.

With specific reference to FIG. 6, the distal end 18 of the first liquid container 12 may include a connection interface for connecting the first liquid container 12 with a fill adapter 32. In some examples, the connection interface may include a tabbed portion 34 located on the outer surface 24 of the barrel 14 on the syringe neck 22 to engage with the groove 35 of the fill adapter 32 to secure the fill adapter 32 to the first liquid container 12. When engaged, the fill adapter 32 facilitates the transfer of liquid F from a second liquid container 36 to the first liquid container 12. In other examples, the connection interface between the first liquid container 12 and the fill adapter 32 may be a threaded connection, a welded connection, a molded connection, an interference fit connection, a snap fit connection, or other mechanical connection.

Figure 8:
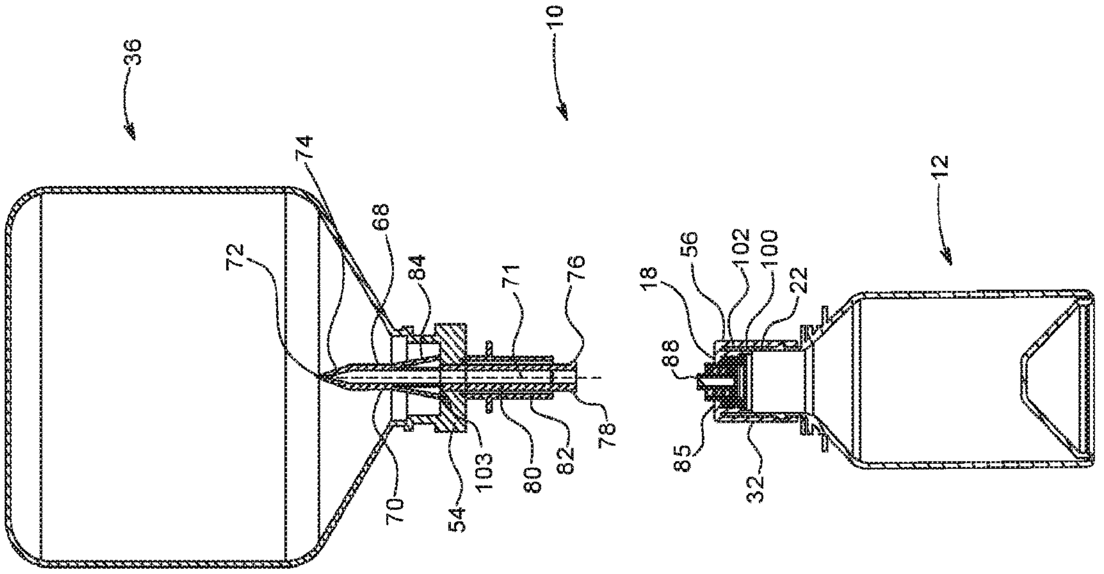
FIG. 8 is a longitudinal cross-sectional view of FIG. 7.
Figure 7:
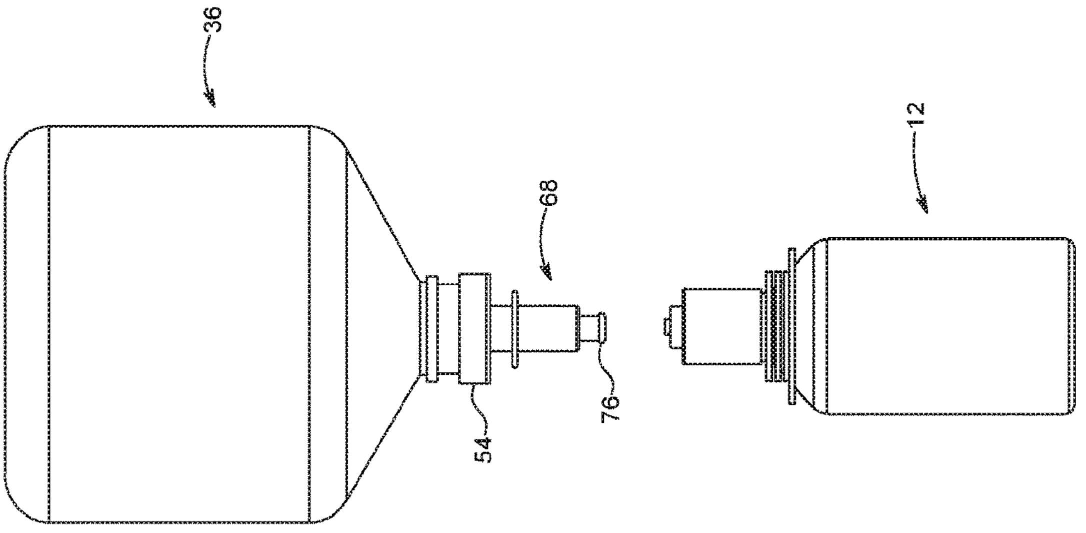
FIG. 7 is a side view of the syringe and fluid transfer assembly of FIG. 1 after the syringe is filled with fluid and a piercing device has been disengaged from a fill adapter.
Figure 9:
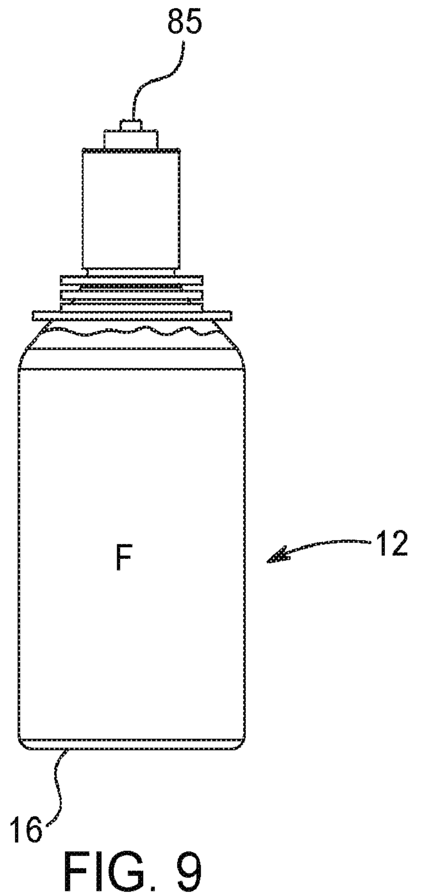
FIG. 9 is a side view of the syringe of FIG. 7.
Figure 10:
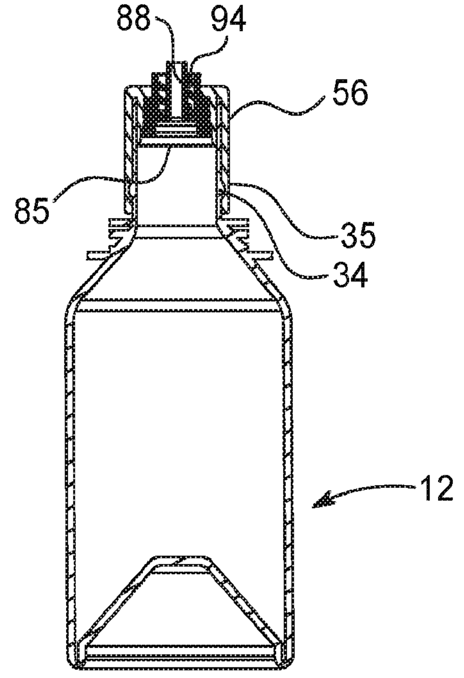
FIG. 10 is a longitudinal cross-sectional view of FIG. 9.

With specific reference to FIG. 8, the body 56 removably receives a piercing device 68 configured for penetrating the piercable septum 54 of the second liquid container 36. The piercing device 68 has a generally cylindrical body 70 and includes a longitudinal axis 71, a piercing point 72 located on a distal end 74, and a flared base 76, flaring radially away from the longitudinal axis 71, located on a proximal end 78. In some examples, the flared base 76 is shaped to promote fluid flow due to the Coandă effect. With reference to FIG. 6, when received within the body 56 of the fill adapter 32, the body 56 of the fill adapter 32 surrounds the body 70 of the piercing device 68 and the piercing point 72 may extend beyond the distal end 60, while the flared base 76 extends toward the proximal end 62 and into the syringe neck 22. The longitudinal axis 71 of the piercing device 68 may be coaxial with the longitudinal axis 58 of the body 56. The piercing device 68 has a first conduit 80 surrounded by a second annular conduit 82. The first conduit 80 is configured to displace air from the interior of the first liquid container 12 during a filling procedure, while the second annular conduit 82 is configured to transfer liquid F from the second liquid container 36 to the first liquid container 12. With some examples, a cross-sectional area of the first conduit 80 can be between 8% and 40% smaller than a cross-sectional area of the second annular conduit 82. Both the first conduit 80 and the second annular conduit 82 extend along the longitudinal axis 71 of the piercing device 68. The first conduit 80 and the second annular conduit 82 may be of equal or different lengths. The first conduit 80 may be concentric with the second annular conduit 82. In some examples, the first conduit 80 and the second conduit 82 may be parallel to each other in a side-by-side arrangement. The first conduit 80 and/or second annular conduit 82 may have a smooth or helical inner sidewall (not shown). With some examples, a ratio of a cross-sectional area of the flared base 76 to a cross-sectional area of the first conduit 80 may be between 5:1 to 20:1. With further examples, a radius of the flared base

76 is desirably less than or equal to a radius of the syringe 12 at a transition between the frusto-conical distal end and the syringe neck 22.

With reference to FIG. 6, the fluid transfer assembly 10 is shown in a second engagement position, where the piercing point 72 penetrates the rubber septum 54 of the second liquid container 36, thereby permitting liquid F to enter the second annular conduit 82. Liquid F travels from the proximal end 78 of the second annular conduit 82 through the fill adapter 32 and into the interior volume 28 of the first liquid container 12 via the syringe neck 22. Liquid flow may be driven by gravity, or it may be vacuum-assisted, such as when the rolling diaphragm syringe 12*a* is unrolled in the proximal direction, or when the plunger 31 of the syringe 12*b* is withdrawn in the proximal direction. The liquid F entering the first liquid container 12 via the second annular conduit 82 contacts the flared base 76 and is deflected radially outward from the longitudinal axis 71 and towards the inner surface 26 of the barrel 14 before dripping down the sidewall 20 of the barrel 14 and accumulating at the bottom of the first liquid container 12. The liquid F initiates flow through the second annular conduit 82 instead of the first conduit 80 because it is at a lower point of the fill adapter 32 and will have a higher head pressure than the inlet for the first conduit 80. The entry of liquid F from the second liquid container 36 into the interior of the first liquid container 12 displaces air contained inside the first liquid container 12 into the second liquid container 36 through the first conduit 80. Any liquid initially flowing through the first conduit 80 is forced out from the first conduit 80 by the air flowing through the first conduit 80 from the first liquid container 12 into the second liquid container 36. Air/liquid exchange within the first fluid container 12 occurs substantially simultaneously through the first conduit 80 and the second annular conduit 82, without any flow hesitation or gurgling due to uneven flow characteristics.

With reference to FIG. 8, the piercing device 68 may further include a plurality of deflectable barbs 84, configured to prevent removal of the piercing device 68 from the second liquid container 36 after the piercing device 68 penetrates the septum 54. The deflectable barbs 84 extend radially outward from the outer surface of the piercing device 68 and form an acute angle therewith. As the piercing point 72 penetrates the piercable septum 54 of the second liquid container 36, the barbs 84 deflect radially inwards towards the longitudinal axis 71 so as to permit the piercing device 68 to pass through the septum 54 and into the second liquid container 36. Likewise, upon exerting a proximally directed force on the piercing device 68, the deflectable barbs 84 extend radially outward to prevent the removal of the piercing device 68 from the second liquid container 36. The proximally directed force causes the piercing device 68 to be disconnected from the body 56 of the fill adapter 32, while the body 56 remains connected to the syringe neck 22 of the first liquid container 12. In this manner, the second liquid container 36 can be discarded, along with the piercing device 68 trapped within the syringe neck 46 of the second liquid container 36.

With reference to FIG. 8, the fill adapter 32 may further include a plug 85 that is releasably connected to the distal end 78 of the piercing device 68. With the removal of the piercing device 68 from the body 56, the plug 85 is moved from a first position (shown in FIG. 6) to a second position (shown in FIG. 8). In the first position, the plug 85 is disconnected from the body 56, while in the second position the plug 85 is connected to the body 56 as described herein. With specific reference to FIG. 11, the plug 85 has an inner member 86 defining a liquid channel 88 that is in liquid communication with the interior volume 28 of the first liquid container 12. The inner member 86 is in alignment with the first conduit of the piercing device (not shown in FIG. 11). The inner member 86 is surrounded by an outer annular skirt 90 that extends axially along at least a portion of the longitudinal length of the inner member 86. The inner member 86 is spaced apart radially from the outer annular skirt 90 by an annular space 92. The outer annular skirt 90 has a threaded portion 94, i.e., a female luer lock member formed on an inner surface 96 facing toward the inner member 86, configured for connecting the first liquid container 12 to a liquid path. An outer surface 98 of the outer annular skirt 90 has at least one foot 100 extending from a portion of a longitudinal length of the outer annular skirt 90 adapted to fit within a correspondingly shaped recess 102 formed on the inner sidewall 64 of the body 56. Once the foot 100 is engaged within the recess 102, the plug 85 is connected to the body 56 to prevent the plug 85 from being removed from the tip of the syringe neck 22. With specific reference to FIG. 8, when the foot 100 is engaged within the recess 102 and the user exerts a proximally directed force on the first liquid container 12 to separate the assembly 10, a bottom portion 103 of the barbs 84 contact the septum 54 of the second liquid container 36 and prevent the piercing device 68 from being withdrawn from the second liquid container 36. As a result, the body 70 of the piercing device 68 and the plug 85 attached to the distal end 78 of the piercing device 68 is forced towards the distal end 18 of the first liquid container 12 until the foot 100 locks within the recess 102. Further, proximal force causes the body 70 of the piercing device 68 to detach from the body 56 of the fill adapter 32, while the plug 85 remains connected to the body 56 and covers the syringe neck 22 of the first liquid container 12. The piercing device 68 may be discarded along with the second liquid container 36.

Figure 11:
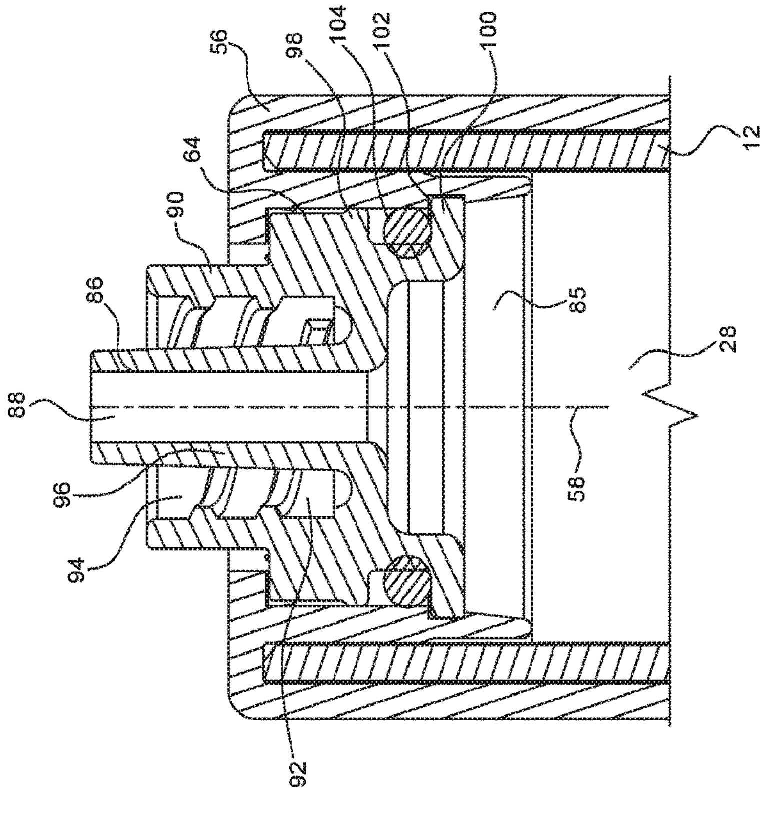
FIG. 11 is a detailed, cross-sectional view of a fill adapter of FIG. 7.

With reference to FIG. 11, tubing (not shown) may optionally be connected to the plug 85, establishing a liquid path from the first liquid container 12 to a patient after the first liquid container 12 has been filled with liquid. In some examples the outer annular skirt 90 of the plug 85 contains a threaded portion 94, i.e., a female luer lock member, formed on an inner surface 96 configured to connect with tubing having a male member (not shown) to create a liquid path. In other examples, the arrangement of the female threading 94 and the male member (not shown) may be reversed. In such examples, the male element is provided on the plug 85, while the tapered female threading 94 is provided on the tubing.

With continued reference to FIG. 11, the inner sidewall 64 of the body 56 may radially flex the at least one foot 100 towards the longitudinal axis 58, to facilitate movement of the plug 85 in a longitudinal direction within the syringe neck 22 when the foot 100 is not engaged within the recess. The outer surface 98 of the plug 85 may further include one or more seals 104 to prevent liquid F from leaking between the body 56 and the plug 85 when the foot 100 is engaged within the recess 102. Alternatively, the one or more seals 104 may optionally be secured on the inner sidewall 64 around the recess 102.

Figure 12:
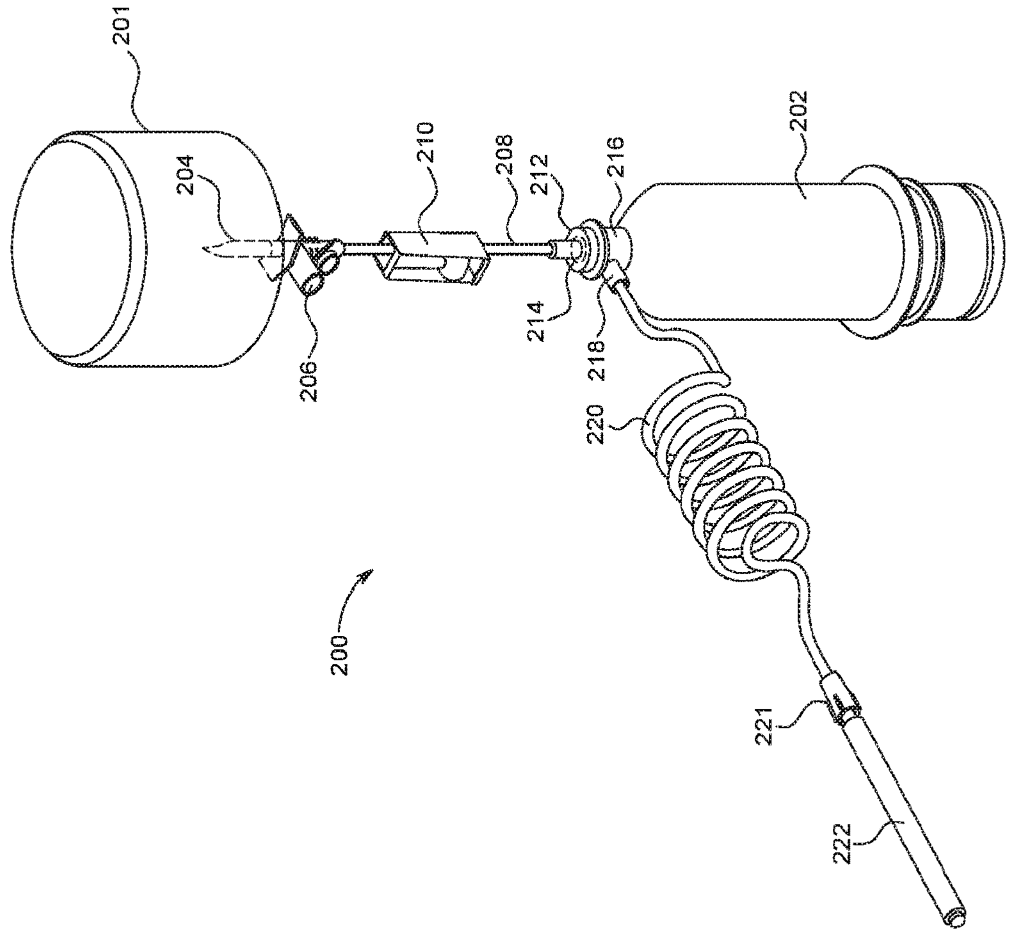
FIG. 12 is a perspective view of a syringe and fluid transfer assembly in accordance with another example of the present disclosure.

Next, referring to FIG. 12, a fluid transfer assembly 200 in accordance with another example of the present disclosure is discussed. The fluid transfer assembly 200 is configured to eliminate the need for vacuum to fill the syringe through activation of the plunger. Instead, the fluid transfer assembly 200 relies upon head pressure of the liquid to increase the fill rate by maintaining the liquid container at a height above the syringe during the filling process. As shown in FIG. 12, the fluid transfer assembly 200 has a syringe 202 and a spike adapter 204 configured for connection to a liquid container 201 above syringe 202. The spike adapter 204 comprises a vent 206 to allow air into the liquid container during the filling process. Connecting the syringe 202 and the spike adapter 204 is a fill tube 208, with the fill tube 208 having a tube clamp 210 placed thereon for selectively stopping or starting the flow of liquid through the fill tube 208. The tube clamp 210 may be any appropriate alternative valve, such as a pinch valve. While the syringe 202 may be connected directly to the spike adapter 204, the fill tube 208 increases the head height of the liquid in the liquid container 201 by increasing the distance between the syringe 202 and the liquid container 201. In this manner, the fill rate of the syringe 202 can be increased because flow rate generally increases with head height when the remaining flow variables are kept constant. In various embodiments, the fill rate for syringe 202 may be selected by selecting a corresponding head height.

Figure 13:
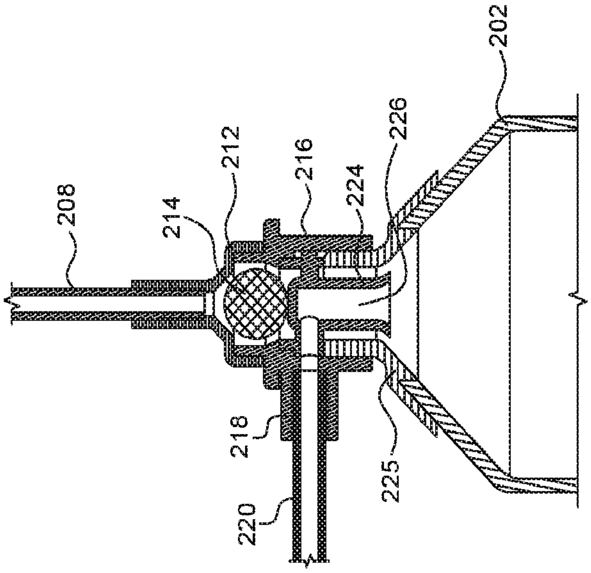
FIG. 13 is a detailed side cross-sectional view of a connection interface of the fill adapter of FIG. 12.

With reference to FIG. 13, and with continued reference to FIG. 12, a valve housing 216 is coupled to the open end of the syringe 202, with the valve housing 216 having a connecting cap 212 thereon and an optional floating ball 214 or other valve design allowing one-way fluid flow retained therein. The valve housing 216 further has a fitting 218, configured for connection with a low-pressure connector tube 220, which may form a wet connection with a separate tube (not shown) connected to the patient once the syringe is filled and the tubing primed. The connector tube 220 has a prime straw 222 connected to a fitting 221 at a distal end thereof. In examples where the floating ball 214 is omitted, a separate valve mechanism (not shown) may be provided to prevent liquid from flowing from the syringe 202 to the liquid container 201.

With continued reference to FIG. 13, the valve housing 216 is shown coupled to the syringe 202, with the fill tube 208 liquidly coupled to the valve housing 216 via the connecting cap 212. Also within the valve housing 216 is a bell-shaped flow controller 224. An open end 226 is configured for fluid communication with the connector tube 220. During the filling process, a liquid from the liquid container 201 (shown in FIG. 12) above the syringe 202 is gravity-fed through the fill tube 208 to the valve housing 216. The floating ball 214 or other one-way valve is configured to allow liquid to flow through the valve housing 216 during the initial fill process, with the liquid flowing down and around an exterior surface of the flow controller 224. Optionally, the bell-shaped contour of the surface of the flow controller 224 urges the liquid along the interior walls of syringe 202 by a ribbed connector 225. The combination of the bell-shaped contour of the flow controller 224 and the conical sidewall of the distal end of the syringe 202 (and/or the ribbed connector 225) results in the liquid filling the syringe 202 in accordance with the Coandă effect. As used herein, the Coandă effect is the tendency for a liquid stream to be attracted to a nearby curved or angled surface as the liquid flows along the surface. Thus, as liquid flows down the flow controller 224 and/or the ribbed connector 225, it is naturally attracted to the inside surface of the conical distal end 250 of the syringe 202, rather than dripping from the edge of the flow controller 224 and/or the ribbed connector 225. The liquid then flows down the tubular sidewall 252 of the syringe 202, ultimately accumulating at the bottom of the syringe 202, filling syringe 202 from the bottom up as air escapes the syringe through flow controller 224 and connector tube 220. This flow along the inside surface of the syringe 202 helps to reduce turbulence as the liquid fills the syringe 202, which aides in reducing air bubbles from forming as the syringe 202 is filled.

As the syringe 202 is filled, the liquid will eventually reach a level within the syringe 202 where it will flow into the open end 226 of the flow controller 224 and flow into the connector tube 220, thereby priming the connector tube 220. When the connector tube 220 is fully primed, any additional liquid flow into the syringe 202 will force the floating ball 214 upward against inner surfaces of the connector cap 212, thereby stopping the flow of liquid from the fill tube 208 into the syringe 202. At this point, the prime straw 222 may be removed and fitting 221 of the connector tube 220 may be connected to a patient-side tube (not shown), and the contents of the syringe 202 may be delivered the patient via a conventional liquid delivery procedure, such as using a powered liquid injector. During an injection procedure where the liquid is delivered from the syringe 202, the floating ball 214 seats against the distal end of the valve housing 216 to prevent the flow of liquid into the liquid container 201. It is to be understood that the rate of liquid flow in the fluid transfer assembly 200 may be optimized via, for example, changes in height between the container and the syringe 202 to increase head pressure, removal of liquid restrictions in the valve areas, increase in the syringe neck size, etc.

Figure 14:
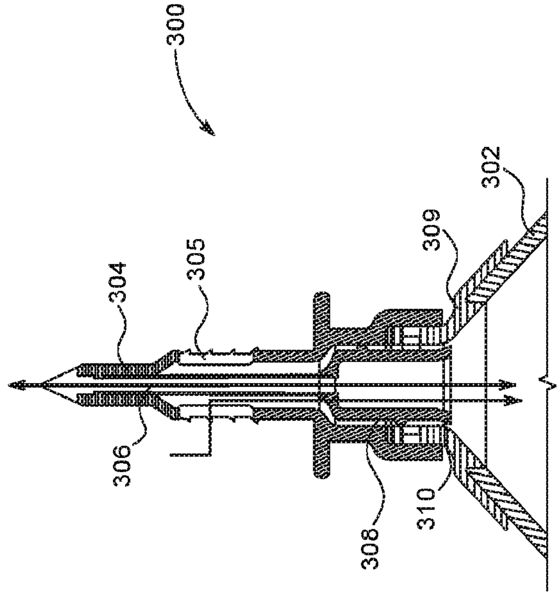
FIG. 14 is a detailed side cross-sectional view of a fluid transfer assembly in accordance with another example of the present disclosure.

Next, referring to FIG. 14, a fill adapter 300 in accordance with another alternative example of the present disclosure is shown. The fill adapter 300 can be used in combination with a syringe 302 having a spike 304 coupled thereto via a snap-on connection, a threaded connection, welding, etc. The spike 304 has a plurality of liquid openings 305 on side surfaces thereof, along with an air exchange conduit 306 running along an axial length therethrough. With some examples, a cross-sectional area of the air exchange conduit 306 can be between 8% and 40% smaller than a cross-sectional area of the conduit in fluid communication with the liquid openings 305. Liquid pressure at the opening 305 is higher than at the air exchange conduit 306 due to head pressure. Thus, liquid in the container will naturally flow through the opening 305. Such an arrangement assures that air exiting from the conduit 306 will not enter into the openings 305 to introduce air bubbles into the syringe during a filling procedure. At an end of the air exchange conduit 306 proximal to the syringe 302 is a bell-shaped flow controller 308. While not shown, the spike 304 is configured for connection to a container (such as the liquid container 201 shown in FIG. 12) above the syringe 302 so as to initiate a flow of liquid from the container into the syringe 302. The liquid within the container is configured to flow into the liquid openings 305 on the spike 304, flowing downward through spike 304 around the periphery of the air exchange conduit 306. Air present within the syringe 302 is simultaneously exchanged with air within the container via the air exchange conduit 306. As the liquid flows along the outer peripheral surfaces of the flow controller 308, it reaches a bell-shaped flare 310 on a proximal end of the flow controller 308, urging the liquid toward a ribbed connector 309 at a distal end of the syringe 302. As discussed above with respect to FIG. 13, this combination of the bell-shaped contour of the flow controller 308 and the ribbed connector 309 results in the liquid filling the syringe 302 in accordance with the Coandă effect. Thus, as liquid flows down the flow controller 308 and the ribbed connector 309, it is naturally attracted to the inside surface of the syringe 302, helping to reduce turbulence as the liquid fills the syringe 302 and aiding in the reduction of air bubbles within the syringe 302.

With some examples, a ratio of a cross-sectional area of the bell-shaped flare 310 to a cross-sectional area of an internal conduit of the flow controller 308 may be between 5:1 to 20:1. With further examples, a radius of bell-shaped flare 310 is desirably less than or equal to a radius of the sidewall of the syringe 302 at a transition between the frusto-conical distal end and the syringe neck.

After the syringe 302 is filled with liquid, the spike 304 may be removed from the container and a connector tube (not shown) may be attached thereto via an appropriate connection, such as a snap-on connection. The connector tube may be connected to a patient-side tube (not shown), and the contents of the syringe 302 may be delivered to the patient via a liquid delivery procedure, such as using a powered liquid injector.

Figure 15A:
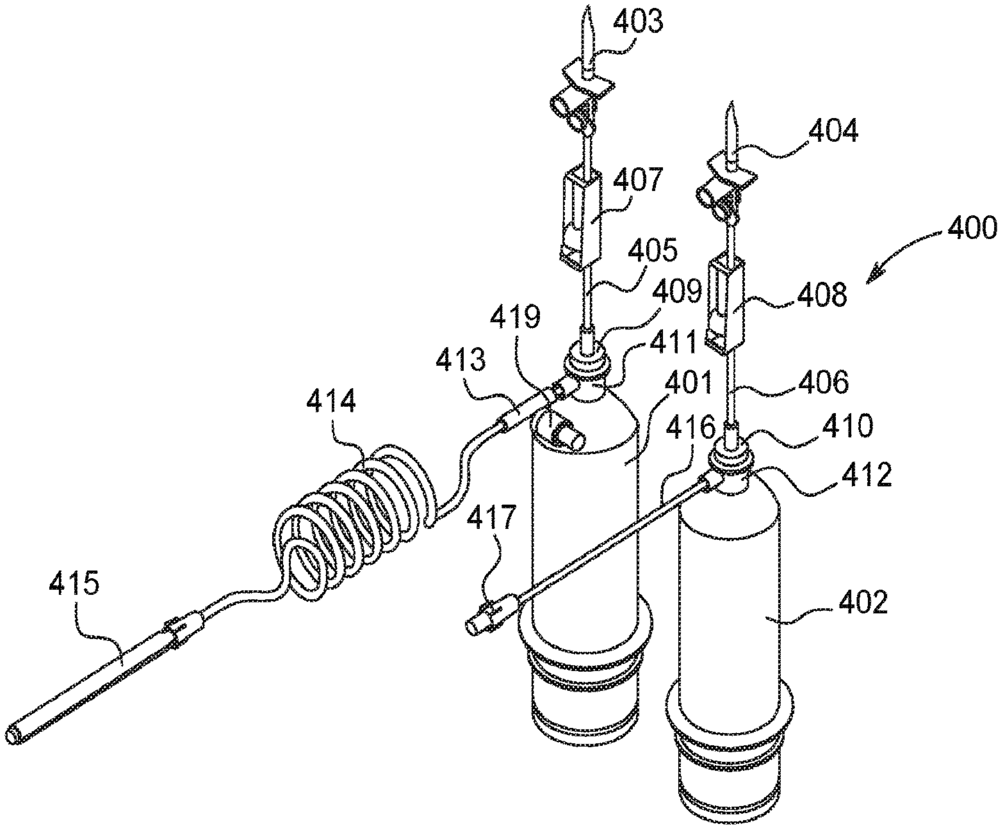
FIG. 15A is a perspective view of a fluid transfer assembly in accordance with another example of the present disclosure.
Figure 15B:
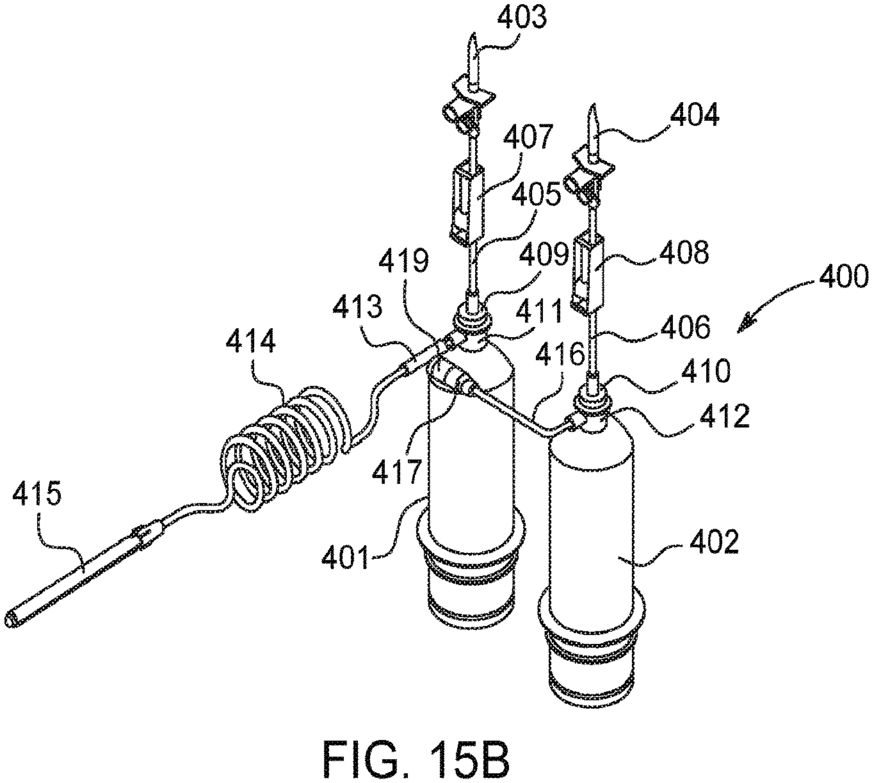
FIG. 15B is another perspective view of the fluid transfer assembly of FIG. 15A.

Referring to FIGS. 15A-15B, a fluid transfer assembly 400 in accordance with another example of the present disclosure is shown. The fluid transfer assembly 400 has dual syringes 401, 402. As is known in the art, many injection procedures involve the injection of two distinct liquids into the patient, for example a contrast agent and saline. The fluid transfer assembly 400 accommodates such a procedure through the use of dual syringes 401, 402. Each syringe 401, 402 is filled in a substantially similar fashion as that described herein, for example as described according to FIGS. 12-14. That is, the syringes 401, 402 and spike adapters 403, 404 are configured for connection to a liquid container (not shown) above the syringes 401, 402. Connecting the syringes 401, 402 and the respective spike adapters 403, 404 are fill tubes 405, 406, with each fill tube 405, 406 having a tube clamp 407, 408 placed thereon for selectively stopping or starting the flow of liquid through the fill tubes 405, 406, respectively.

Each syringe 401, 402 is coupled to a respective valve housing 411, 412 having respective connector caps 409, 410. Accordingly, syringes 401, 402 are filled with respective liquids in substantially the same manner as that described above with respect to FIGS. 12-14. As shown in FIG. 15A, the valve housing 411 is liquidly coupled to a T-connector 413. The T-connector 413 couples the valve housing 411 to a low-pressure connector tube 414, with the connector tube 414 having a prime straw 415 connected at a distal end thereof. The T-connector 413 also comprises a fitting 419. On the other hand, valve housing 412 on syringe 402 is coupled directly to a connector tube 416 having a fitting 417 on a distal end thereof.

After filling of respective syringes 401, 402 in a manner similar to that described above with respect to FIGS. 12-14, the fluid transfer assembly 400 provides that the contents of the syringes 401, 402 may be simultaneously or sequentially injected into the patient through connector tube 414. That is, referring to FIG. 15B, after filling of the syringes 401, 402, the connector tube 416 and the fitting 417 may be coupled to the fitting 419 on the T-connector 413. With this fluid connection, the respective liquids within the syringes 401, 402 may be combined together or flowed sequentially during the injection process and provided to the patient via a wet connection to the connector tube 414.

Figure 16:
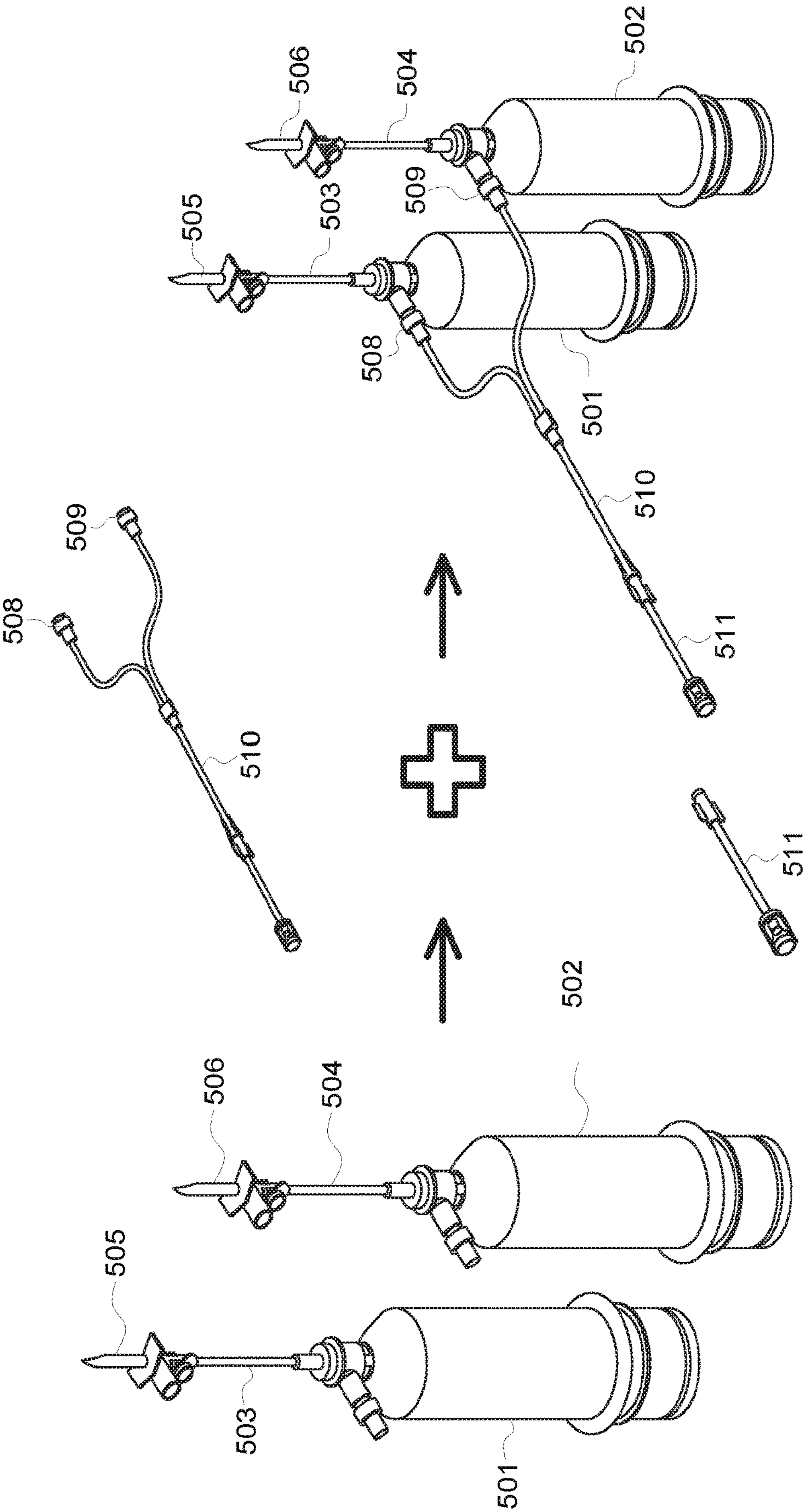
FIG. 16 is an exploded perspective view of a fluid transfer assembly in accordance with another example of the present disclosure.

FIG. 16 illustrates another alternative example of the present disclosure. Dual syringes 501, 502 are shown as liquidly coupled to respective spike adapters 505, 506 via respective fill tubes 503, 504. The filling procedure may be substantially similar to that described above with respect to FIGS. 12-13 and FIGS. 15A-15B. After the syringes 501, 502 are filled with the appropriate liquids, they may be coupled to a Y-shaped connector tube 510 via respective check valve fittings 508, 509. The connector tube 510 may then be connected to a patient-side tube 511 at a distal end thereof. With this fluid connection, the respective liquids within the syringes 501, 502 may be combined together or delivered sequentially during the injection process and provided to the patient via a wet connection to the connector tube 510. Such a configuration may be particularly effective for multi-patient injector applications, as the connector tube 510 can be a disposable connection and the check valve fittings 508, 509 may prevent bi-directional flow of liquids and contamination of the respective syringes 501, 502.

Figure 17A:
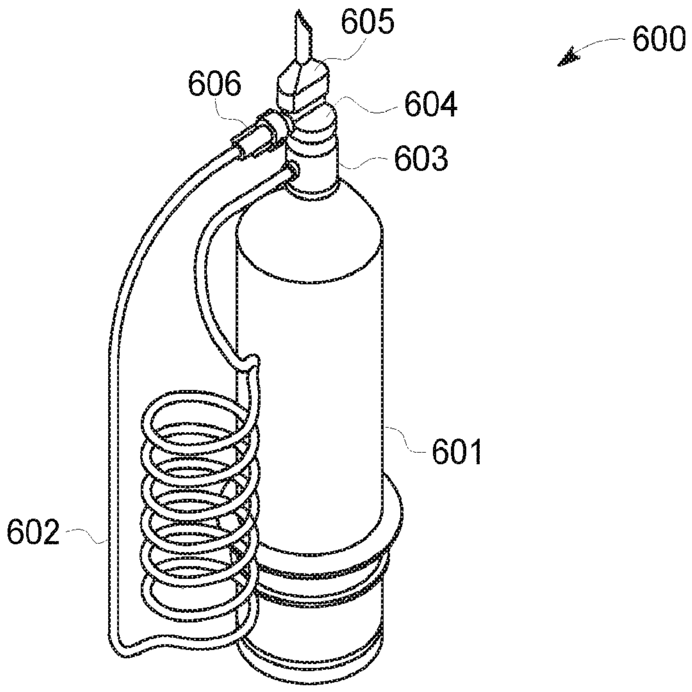
FIG. 17A is a perspective view of a fluid transfer assembly in accordance with another example of the present disclosure.
Figure 17B:
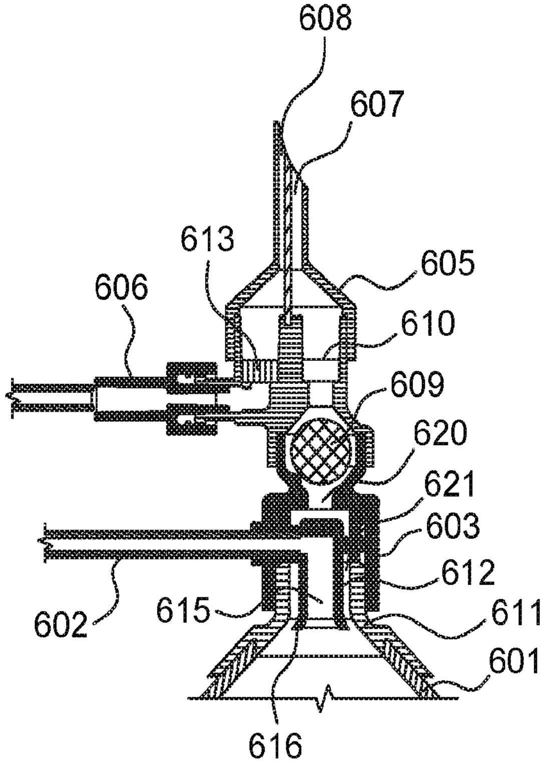
FIG. 17B is a detailed side cross-sectional view of the fluid transfer assembly of FIG. 17A.

Referring now to FIGS. 17A-17B, a fluid transfer assembly 600 in accordance with another example of the present disclosure is described. FIG. 17A illustrates a syringe 601 having a valve housing 603 coupled thereto, wherein the valve housing 603 has a connector cap 604 connected thereon. A spike adapter 605 is coupled to the connector cap 604, while a low-pressure connector tube 602 is liquidly connected between the valve housing 603 and the connector cap 604, with a fitting 606 configured to provide the removable connection between the connector tube 602 and the connector cap 604. FIG. 17B provides greater detail of the liquid paths associated with fluid transfer assembly 600. For example, the spike adapter 605 has a pair of conduits 607, 608. The liquid conduit 607 allows liquid from within a container (not shown) coupled to the spike adapter 605 to flow down to a conduit 610 within the connector cap 604. Air conduit 608 allows air from the container to escape as the fluid is introduced through the liquid conduit 607. With some examples, a cross-sectional area of the air conduit 608 can be between 8% and 40% smaller than a cross-sectional area of the liquid conduit 607. As shown in FIG. 17B, the distal end of air conduit 608 is positioned distally from the distal end of liquid conduit 607. With some examples, the air conduit 608 may extend 0.15 in. to 0.25 in. distally further than the liquid conduit 607. In this manner, liquid pressure at the opening of the liquid conduit 607 is higher than liquid pressure at the air conduit 608 due to difference in head pressure. Due to this difference in pressure, air can be forced out of the container through the air conduit 607 as the container is being filled through the liquid conduit 608. In addition, introduction of fluid into the first fluid container through the liquid conduit 608 also causes a vacuum in the second fluid container, which "pulls" the air from the first fluid container into the second fluid container through the air conduit 608. As the syringe 601 is being filled, liquid is able to flow around an optional floating ball 609 within the valve housing 603 and through a passage 620. The liquid is then able to flow around the periphery of a bell-shaped flow controller 612 via a flow passage 621. As discussed above with respect to FIGS. 12 and 13, the flow controller 612 is shaped and sized so as to direct the liquid to flow along the inner surfaces of syringe 601 as syringe 601 is filled via the Coandă effect. A flared portion 616 of the flow controller 612 and the ribbed connector 611 on a distal end of syringe 601 may also direct such liquid flow. With some examples, a ratio of a cross-sectional area of the flared portion 616 to a cross-sectional area of the flow passage 621 may be between 5:1 to 20:1. With further examples, a radius of the flared portion 616 is desirably less than or equal to a radius of the sidewall of the syringe 601 at a transition between the frusto-conical distal end and the syringe neck.

As the liquid from the container fills syringe 601, air within the syringe 601 is able to pass through a passage 615 formed in the flow controller 612, with the air then passing through the connector tube 602 and into a conduit 608 of the spike adapter 605, where the air enters the container. As the syringe 601 fills with liquid, the liquid itself enters the passage 615 and primes the connector tube 602. The liquid is prevented from entering the conduit 608 (and thus re-entering the container) via a filter 613 at which point connector tube 602 is primed with liquid. After the connector tube 602 is fully primed with liquid, the liquid still entering the syringe 601 urges the floating ball 609 upward, effectively sealing the syringe 601 from receiving more liquid. During an injection procedure where the liquid is delivered from the syringe 601, the floating ball 609 seats against the distal end of the spike adapter 605 to prevent the flow of liquid into the liquid container (not shown).

After the syringe 601 is filled with contrast or saline and the connector tube 602 is fully primed, the connector tube 602 may be detached from the connector cap 604 at the fitting 606, and a patient-side connector tube can, in turn, be connected to the fitting 606 such that the contents of the syringe 601 may be delivered to the patient via a conventional liquid delivery procedure, such as using a powered liquid injector.

Referring to FIGS. 18A-18E, a fluid transfer assembly 700 in accordance with another example of the present disclosure is described. Many of the components of system 700 are the same or similar to those of system 600 described above with respect to FIGS. 17A-17B, so duplicative components will not be discussed in detail. The fluid transfer assembly 700 has a syringe 701 liquidly coupled to a container 702 via two distinct connector tubes 704, 705. One end of the respective connector tubes 704, 705 is coupled to a spike adapter 703 that provides an engagement with the container 702. The syringe 701 has a valve housing 708 coupled thereto, wherein the valve housing 708 has a connector cap 707 connected thereon. Respective connector tubes 704, 705 are coupled to the connector cap 707, while a low-pressure connector tube 709 is liquidly connected between the valve housing 708 and the connector cap 707, with a fitting 710 configured to provide the removable connection between the connector tube 709 and the connector cap 707. Additionally, a tube clamp 706 (or other appropriate valve) is coupled to the connector tube 705 to enable the flow through the connector tube 705 to be shut off.

Figure 18B:
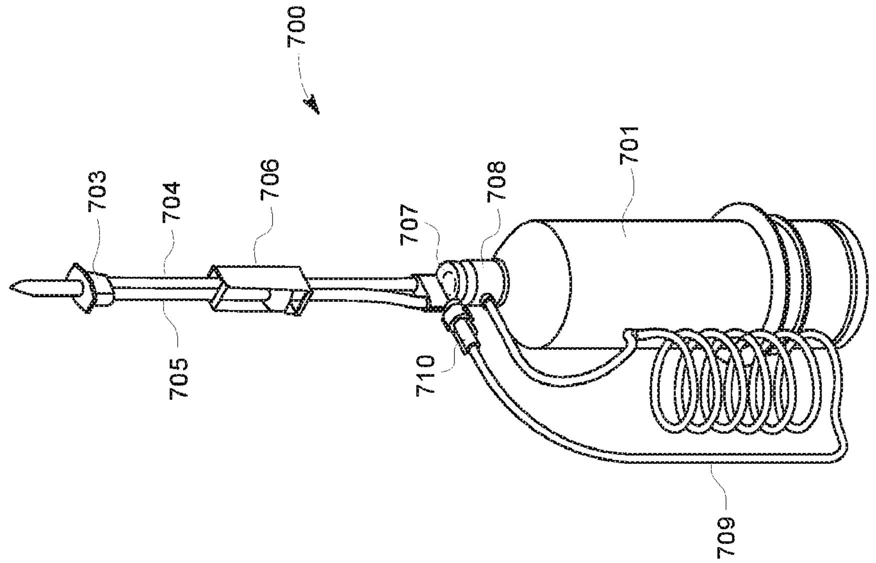
FIG. 18B is another perspective view of the fluid transfer assembly of FIG. 18A.
Figure 18A:
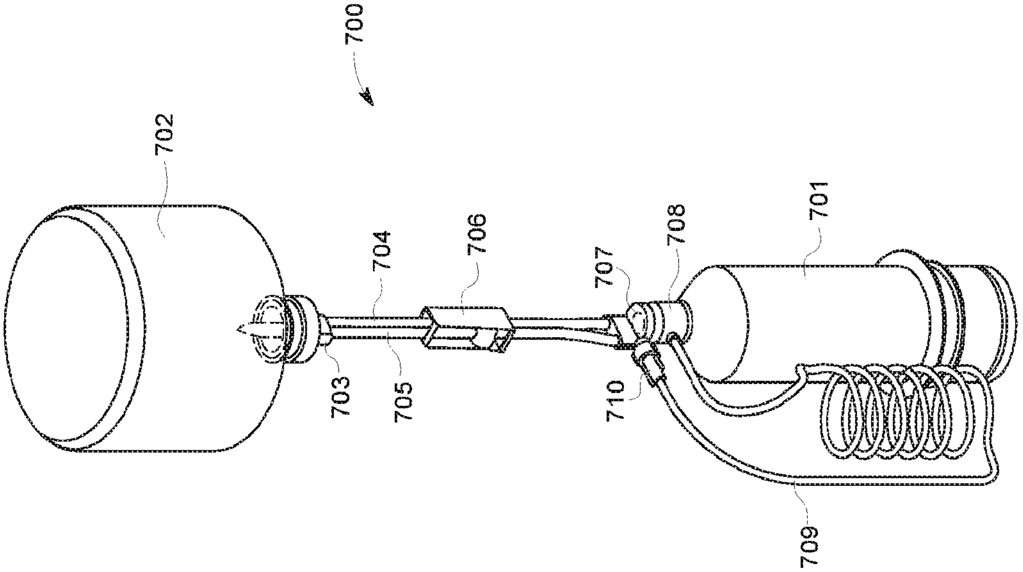
FIG. 18A is a perspective view of a fluid transfer assembly in accordance with another example of the present disclosure.
Figure 18D:
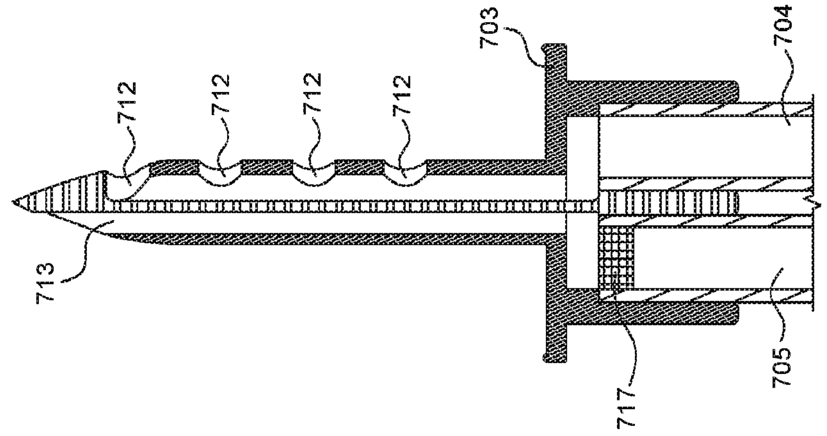
FIG. 18D is a detailed side cross-sectional view of a spike adapter of FIG. 18A.
Figure 18C:
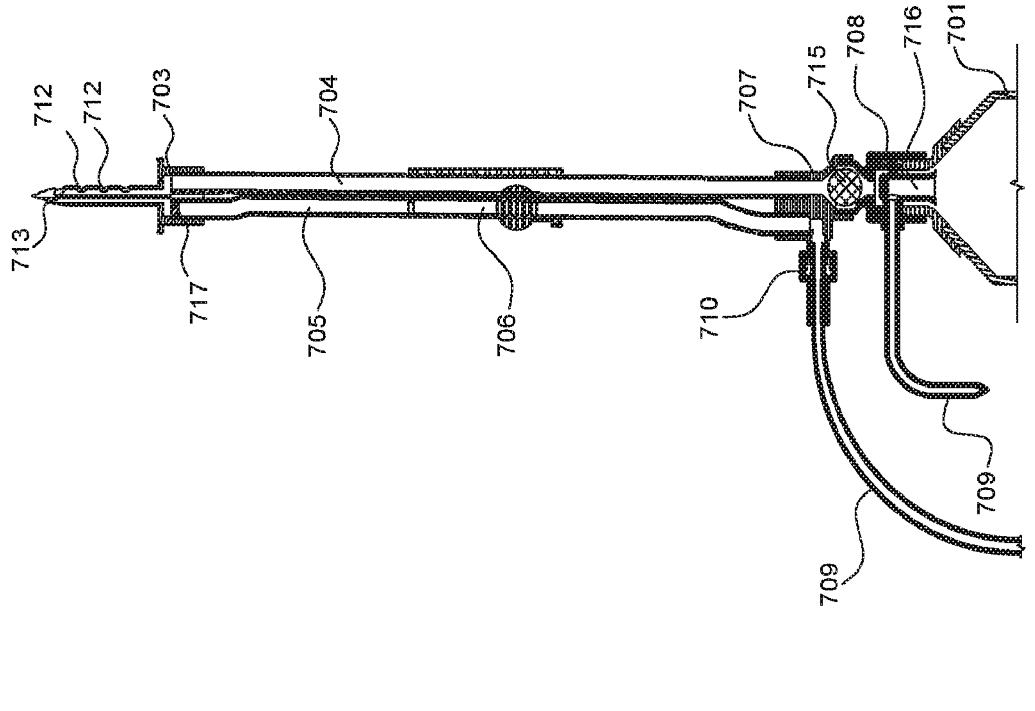
FIG. 18C is a detailed side cross-sectional view of the fluid transfer assembly of FIG. 18A.
Figure 18E:
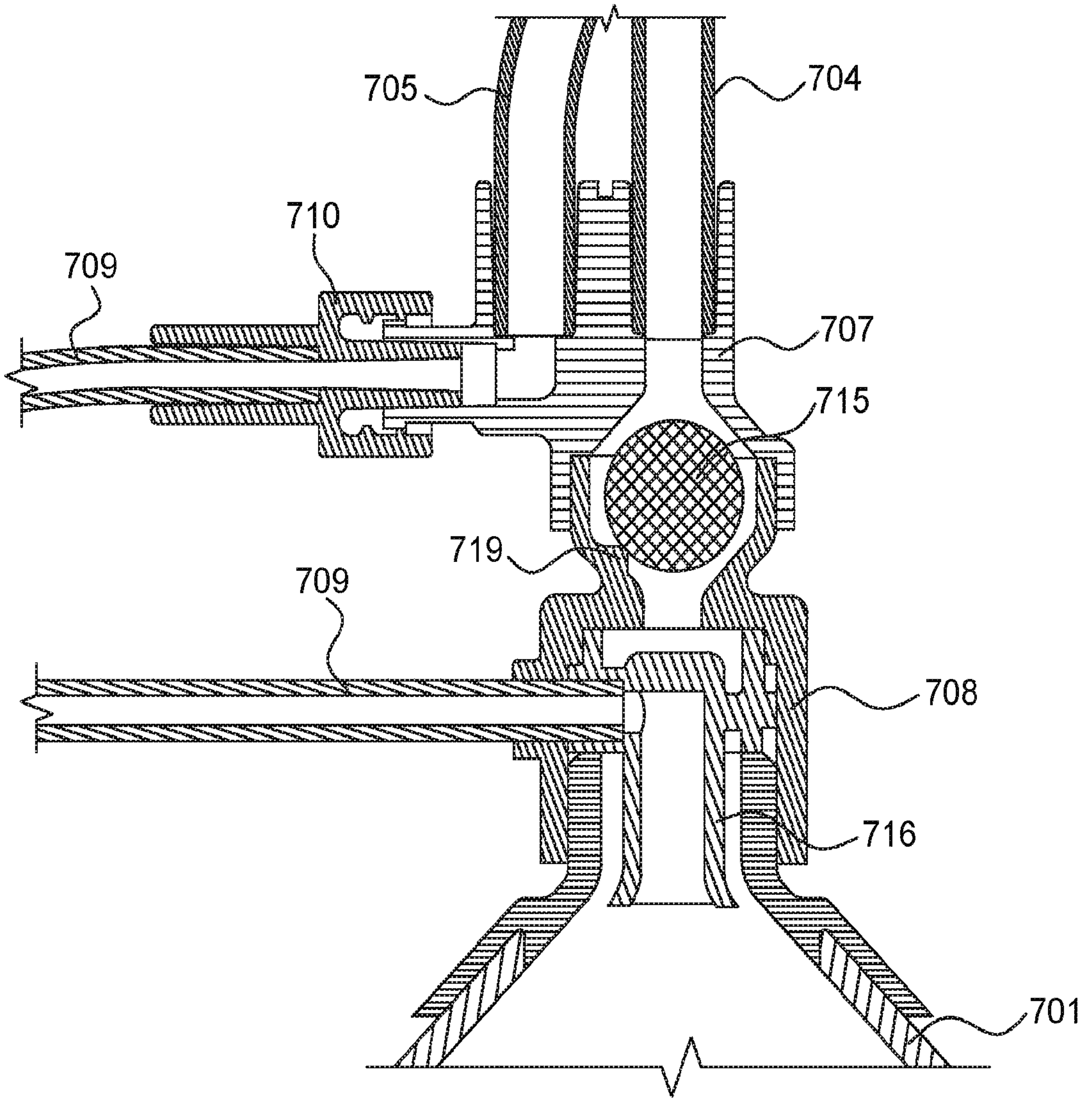
FIG. 18E is a detailed side cross-sectional view of a connection interface of the fill adapter of FIG. 18A.

Referring specifically to FIGS. 18C-18E, greater detail of the liquid paths associated with the fluid transfer assembly 700 is shown. For example, the spike adapter 703 has a plurality of liquid openings 712 extending laterally through the spike adapter 703 configured to enable liquid from the container 702 to enter the connector tube 704. The spike adapter 703 also has a conduit 713 configured for air communication with the connector tube 705 and the headspace of container 702. Openings 712 allow liquid from the container 702 to flow down to the connector cap 707. The openings 712 may have a cross-sectional area of from 0.01 to 0.10 $in^2$ or around 0.06 $in^2$. With some examples, a cross-sectional area of the conduit 713 can be between 8% and 40% smaller than a cross-sectional area of the conduit in fluid communication with the openings 712. As the syringe 701 is being filled, liquid is able to flow around an optional floating ball 715 within the valve housing 708 and into the syringe 701, as the floating ball 715 is held on a surface 719 within the valve housing 708 that enables liquid flow thereby. Once again, as discussed above with respect to FIGS. 12-13, a flow controller 716 is shaped and sized so as to direct the liquid to flow along the inner surfaces of the syringe 701 as the syringe 701 is filled via the Coandă effect.

As the liquid from the container 702 fills the syringe 701, air within the syringe 701 is able to pass through the flow controller 716, with the air then passing through a connector tube 709 and into the conduit 713 of the spike adapter 703, where the air enters the container 702 (shown in FIG. 18A). As the syringe 701 fills with liquid, the liquid itself enters the flow controller 716 and primes the connector tube 709. The liquid is prevented from entering the conduit 713 (and thus re-entering the container) via a filter 717. After the connector tube 709 is fully primed with liquid, the liquid still entering the syringe 701 urges the floating ball 715 upward, effectively sealing the syringe 701 from receiving more liquid. During an injection procedure where the liquid is delivered under pressure from the syringe 701, the floating ball 715 seats against the distal end of the valve housing 708 to prevent the flow of liquid into the liquid container 702. Flow through tubes 703, 704 may also be prevented by tube claim 706.

With specific reference to FIG. 18D, the openings 712 may be spaced apart axially relative to one another. When the spike adapter 703 is inserted into the liquid container, liquid pressure at the openings 712 from the liquid in the container increases from the distal end of the spike adapter 703 toward the proximal end of the spike adapter 703. In this manner, the liquid pressure at the distal most opening 712 will be slightly lower than the liquid pressure at the proximal most opening 712. Thus, liquid in the container will first flow through the proximal most opening 712 before flowing through the distal openings 712. Such an arrangement assures that air exiting from the conduit 713 will not enter into the openings 712 to introduce air bubbles into the syringe during a filling procedure, for example due to a Venturi effect.

After the syringe 701 is filled and the connector tube 709 is fully primed, the connector tube 709 may be detached from the connector cap 707 at the fitting 710, and a patient-side connector tube can, in turn, be connected to the fitting 710 such that the contents of the syringe 701 may be delivered to the patient via a conventional liquid delivery procedure, such as using a powered liquid injector.

Figure 19A:
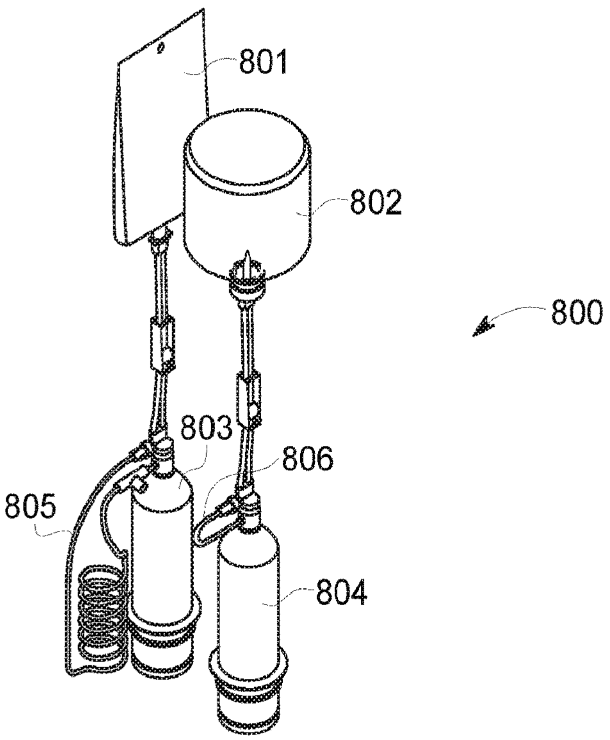
FIG. 19A is a perspective view of a fluid transfer assembly in accordance with another example of the present disclosure.
Figure 19B:
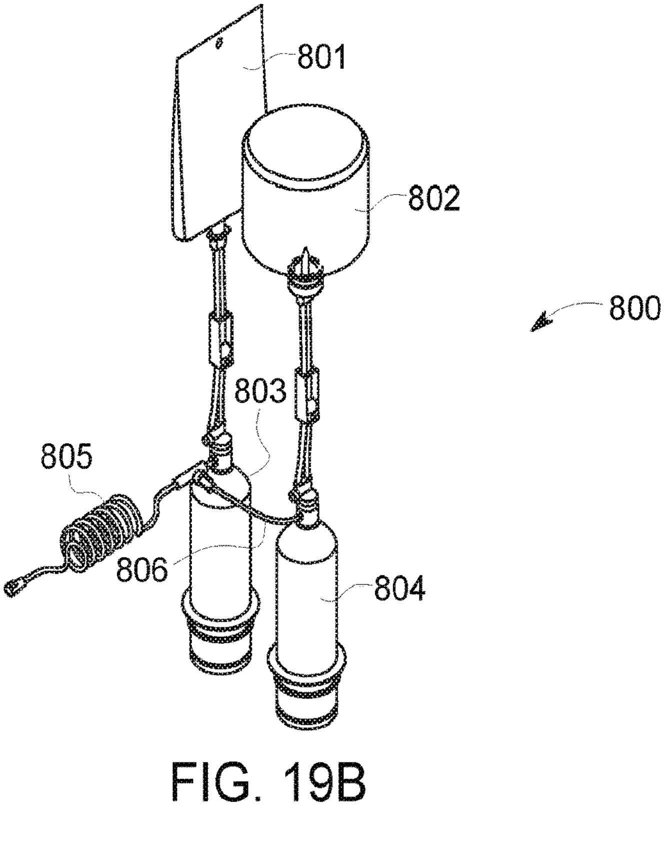
FIG. 19B is another perspective view of the fluid transfer assembly of FIG. 19A.

Turning to FIGS. 19A-19B, a fluid transfer assembly 800 in accordance with another example of the present disclosure is shown. The fluid transfer assembly 800 has a first container (e.g., a saline bag) 801 and a second container 802 (e.g., a bottle of contrast agent) liquidly coupled to respective first and second syringes 803, 804. The details of how the first and second syringes 803, 804 are filled is substantially similar to that disclosed above with respect to FIGS. 18A-18E, so further description of the fill process will be omitted herein. As FIG. 19A shows, during the fill process, a low-pressure connector tube 805 forms a passageway between the first syringe 803 and a connector tube leading to the first container 801, while a separate tube 806 provides the passageway between the second syringe 804 and a connector tube leading to the second container 802. However, referring to FIG. 19B, after filling of the first and second syringes 803, 804 with the respective liquids, the connector tube 806 may be coupled to the connector tube 805. With this fluid connection, the respective liquids within the first and second syringes 803, 804 may be combined together or delivered sequentially during the injection process and provided to the patient via a wet connection to the connector tube 805.

Figure 20:
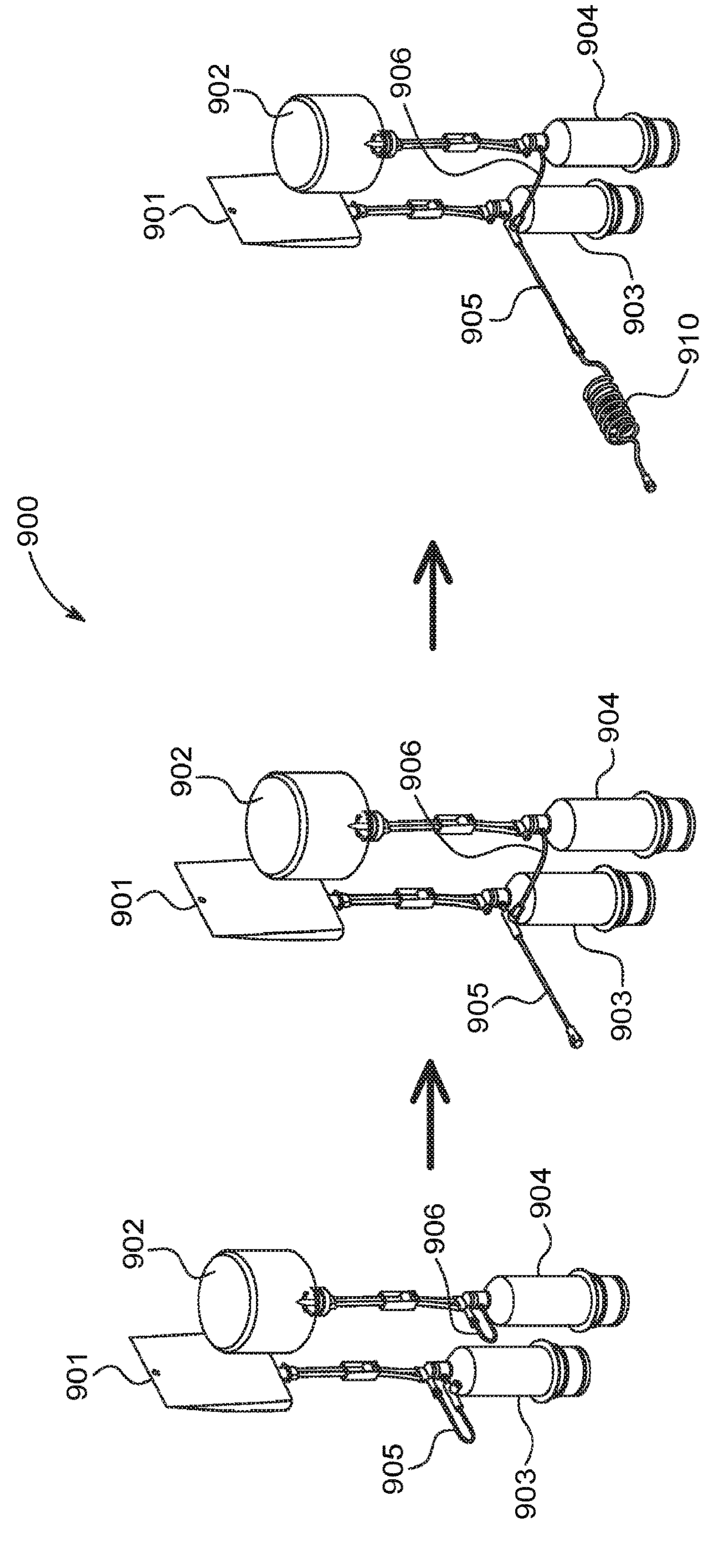
FIG. 20 is a perspective view of a fluid transfer assembly in accordance with another example of the present disclosure.

Referring to FIG. 20, a fluid transfer assembly 900 in accordance with another alternative example of the present disclosure is shown. The fluid transfer assembly 900 has a first container (e.g., a saline bag) 901 and a second container (e.g., a bottle of contrast agent) 902 liquidly coupled to respective first and second syringes 903, 904. Once again, the details of how the first and second syringes 903, 904 are filled is substantially similar to that disclosed above with respect to FIGS. 18A-18E, so further description of the fill process will be omitted herein. During the fill process, a connector tube 905 forms a passageway between the first syringe 903 and a connector tube leading to the first container 901, while a separate tube 906 provides the passageway between the second syringe 904 and a connector tube leading to the second container 902. After the filling of the first and second syringes 903, 904, the connector tube 906 may be coupled to the connector tube 905. With this fluid connection, the respective liquids within the first and second syringes 903, 904 may be combined together or delivered sequentially during the injection process. A separate low-pressure connector tube 910 may then be coupled to the connector tube 905, primed, and provided to the patient via a wet connection to the connector tube 910.

Referring now to FIGS. 21A-21F, a fluid transfer assembly 1000 in accordance with another example of the present disclosure is illustrated. In particular, the fluid transfer assembly 1000 shows greater detail regarding a flow controller 1006 held within a valve housing 1002. Similar to previous examples discussed above, the fluid transfer assembly 1000 has a valve housing 1002 having a connector cap 1012 coupled thereto, with an optional floating ball 1004 retained therein. Liquid is able to enter the valve housing 1002 via a connector tube 1013 connected to a container (not shown) positioned thereabove. The floating ball 1004 enables liquid to pass thereby by resting on a surface 1005 having liquid passages therein. The flow controller 1006 is further coupled to a connector tube 1009, which allows air and/or liquid to pass therethrough. During an injection procedure where the liquid is delivered from the syringe 1008 under pressure, the floating ball 1004 seats against the distal end of the valve housing 1002 to prevent the flow of liquid into the liquid container.

Figure 21A:
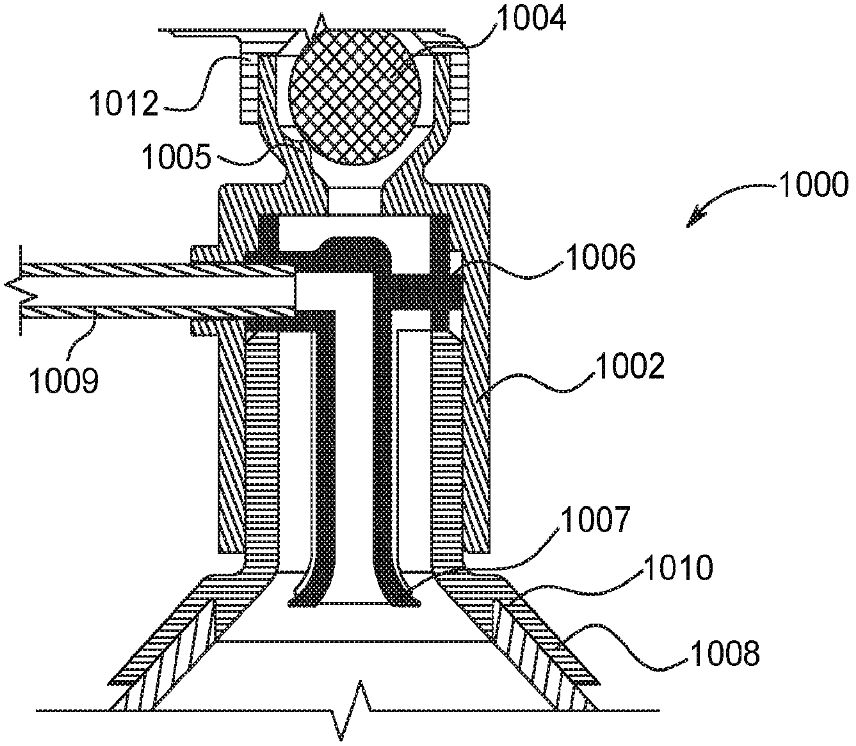
FIG. 21A is a detailed side cross-sectional view of a connection interface of a fill adapter in accordance with another aspect.
Figure 21B:
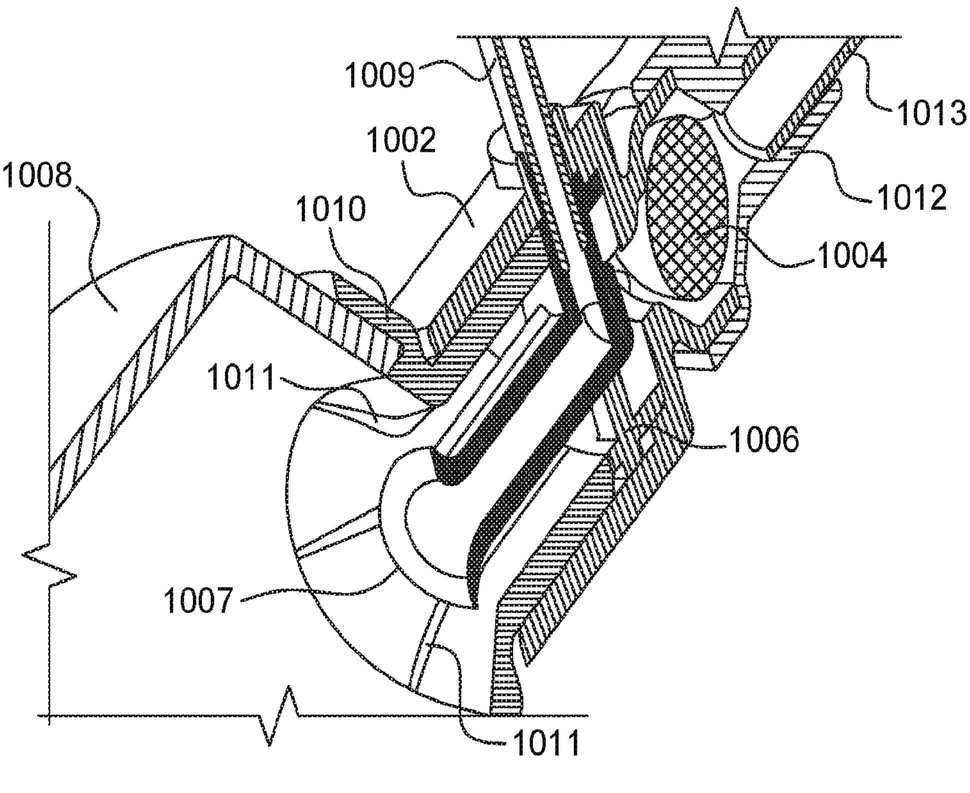
FIG. 21B is a detailed perspective cross-sectional view of the connection interface of FIG. 21A.
Figure 21C:
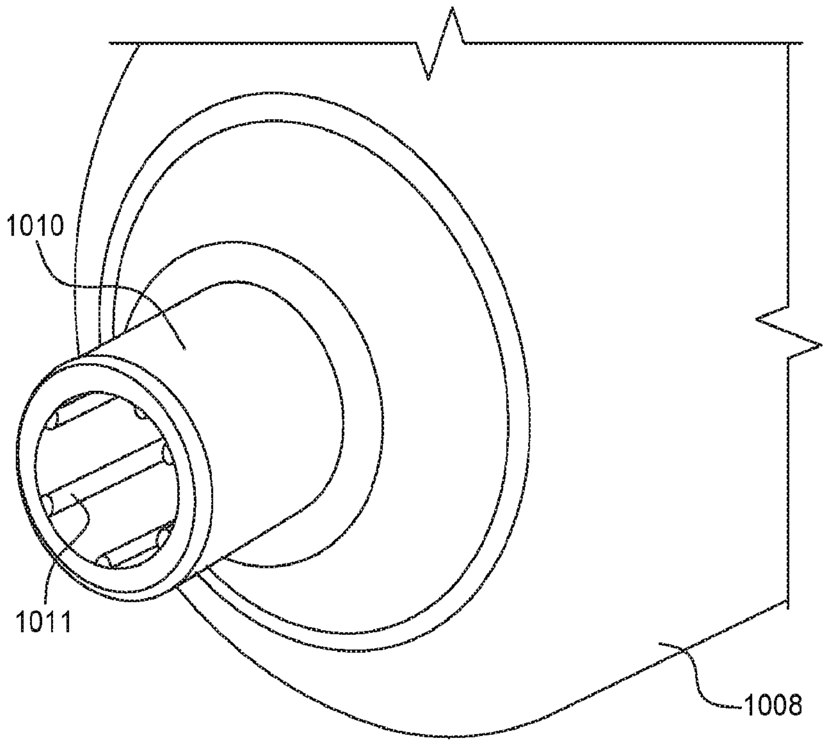
FIG. 21C is a perspective view of a syringe in accordance with the fill adapter of FIG. 21A.
Figure 21D:
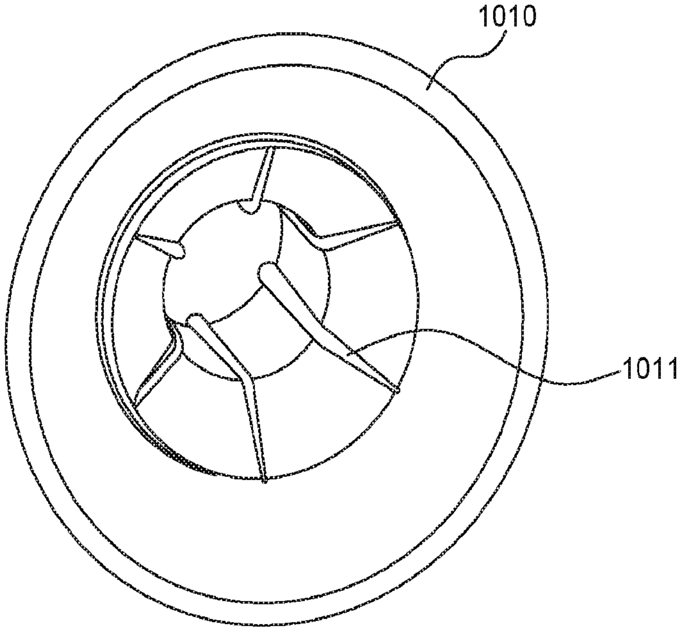
FIG. 21D is a perspective view of a ribbed connector of a fill adapter of FIG. 21A.
Figure 21E:
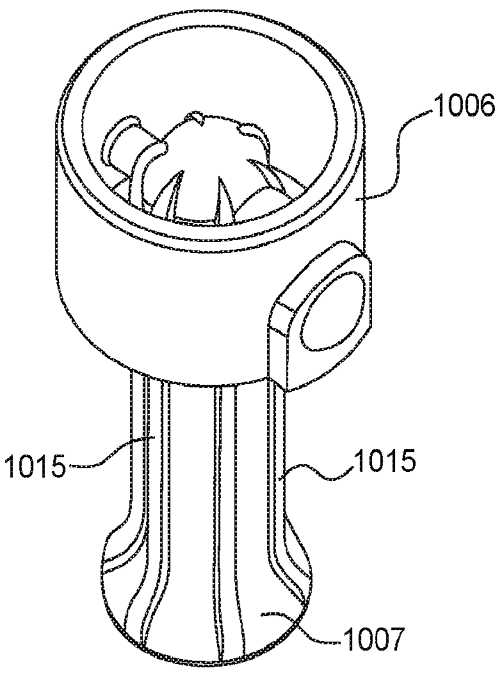
FIG. 21E is a perspective view of a flow controller of the fill adapter of FIG. 21A.
Figure 21F:
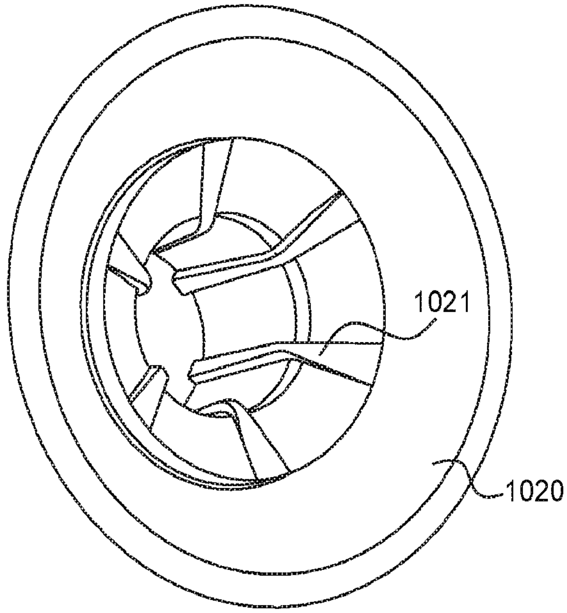
FIG. 21F is a perspective view of a ribbed connector in accordance with another example of the fill adapter of FIG. 21A.
Figure 22A:
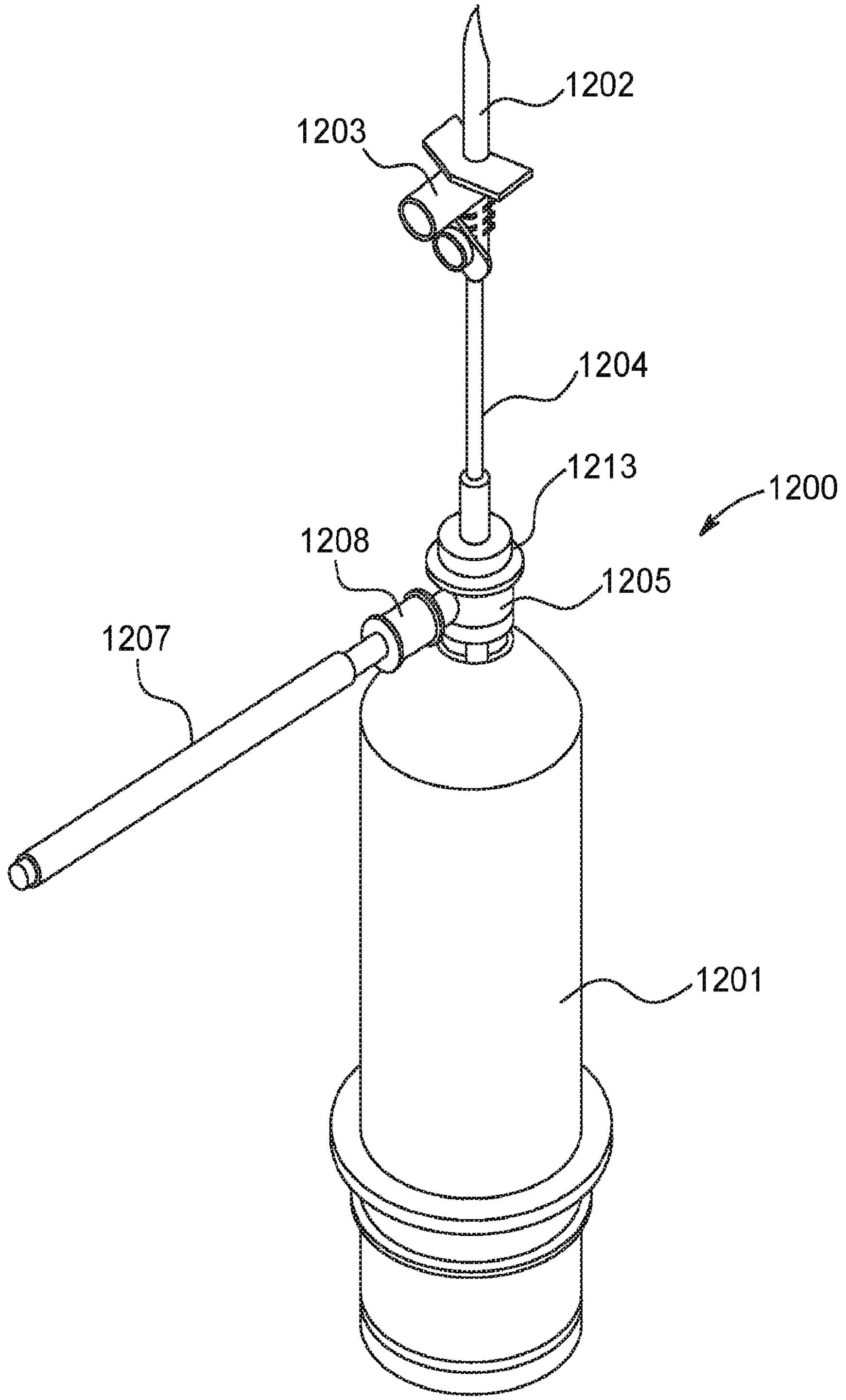
FIG. 22A is a perspective view of a fluid transfer assembly in accordance with another aspect.
Figure 22B:
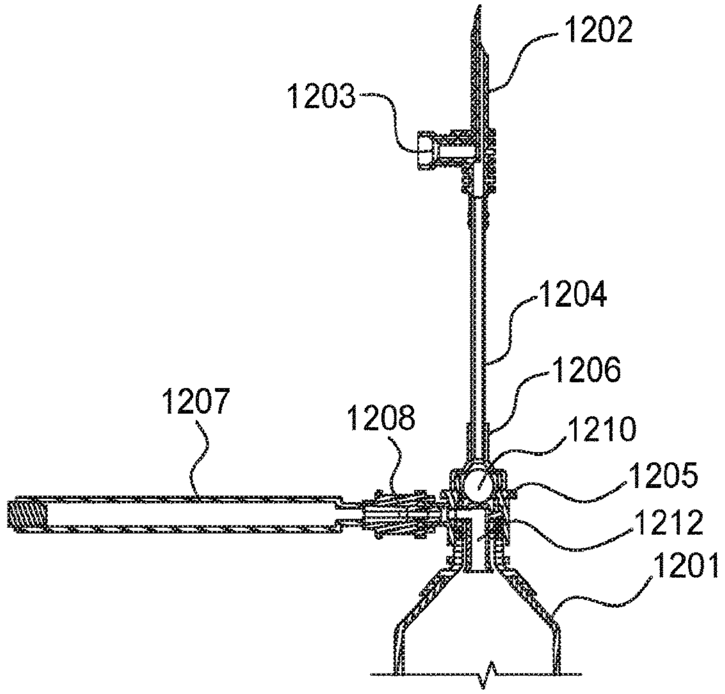
FIG. 22B is a detailed side cross-sectional view of the fluid transfer assembly of FIG. 22A.
Figure 22C:
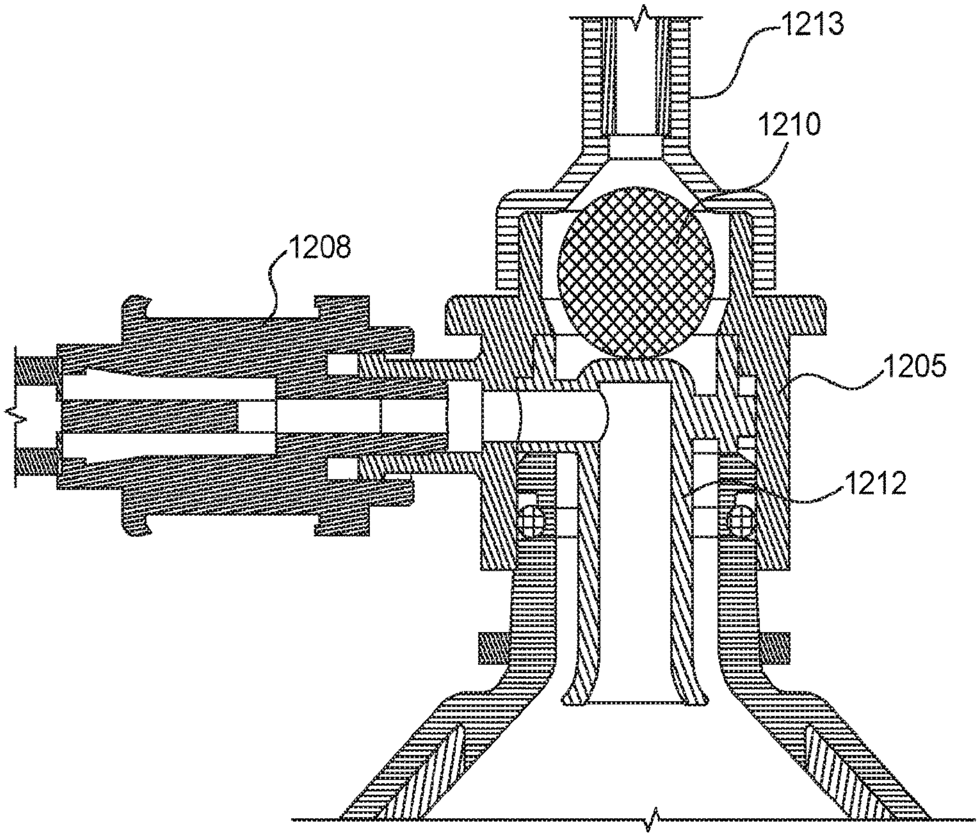
FIG. 22C is a detailed side cross-sectional view of a connection interface of the fill adapter of FIG. 22A.
Figure 22D:
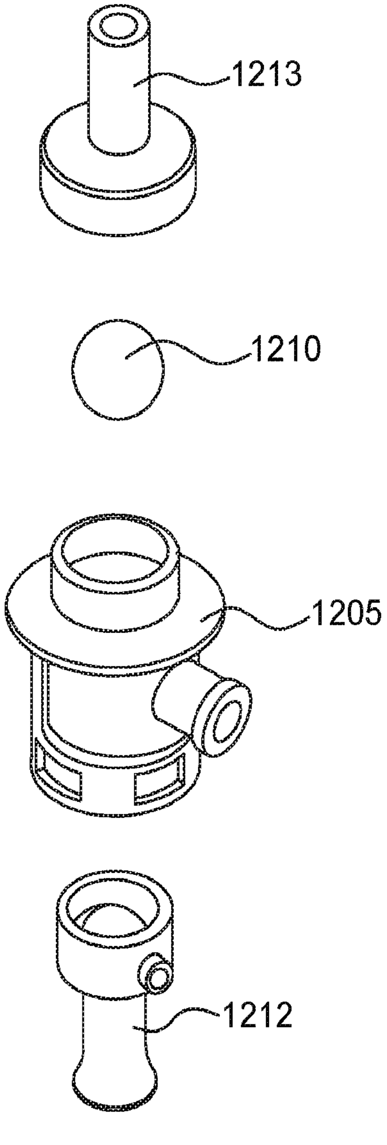
FIG. 22D is an exploded view of a valve housing of the fluid transfer assembly of FIG. 22A.

As discussed above, the flow controller 1006 is sized and shaped so as to direct the liquid flowing thereon to adhere to the inner surface of the syringe 1008 in accordance with the Coandă effect. To achieve flow in accordance with the Coandă effect, it may be advantageous to provide ribs or contours on one or both of the external surfaces of the flow controller 1006 and a ribbed connector 1010. For example. FIGS. 21C-21D illustrate the ribbed connector 1010, with a plurality of rounded ribs 1011 formed on an inner surface thereon. As liquid passes through ribbed connector 1010, the ribs 1011 may direct the liquid flow so as to encourage adhesion of the liquid to the inner surfaces of the syringe 1008. Likewise, the flow controller 1006 may be sized and shaped to further induce such liquid flow. As shown in FIG. 21E, the flow controller 1006 may have a plurality of ribs 1015 thereon, which similarly encourage uniform liquid flow. The ribs 1015 may have equal or unequal angular spacing around a longitudinal axis of the flow controller 1006. The ribs 1015, coupled with a flared end 1007, may further encourage adhesion of the liquid to the inner surfaces of syringe 1008. Also, while the ribbed connector 1010 is shown having rounded ribs 1011, it may also be advantageous to have ribs of a different shape to control flow. For example, as FIG. 21F shows, a ribbed connector 1020 may have a plurality of squared ribs 1021 having flared ends to encourage liquid flow along the inner surfaces of the syringe 1008. With some examples, a ratio of a cross-sectional area of the flared end 1007 to a cross-sectional area of an internal conduit of the flow controller 1006 may be between 5:1 to 20:1. With further examples, a radius of the flared end 1007 is desirably less than or equal to a radius of the sidewall of the syringe 1008 at a transition between the frusto-conical distal end and the syringe neck.

Next, referring to FIGS. 22A-22D, a fluid transfer assembly 1200 in accordance with another example of the present disclosure is shown. The fluid transfer assembly 1200 has a syringe 1201 and a spike adapter 1202 configured for connection to a liquid container (not shown) above syringe 1201. The spike adapter 1202 has a vent 1203 to allow air into the liquid container during the filling process. Connecting the syringe 1201 and the spike adapter 1202 is a fill tube 1204. A valve housing 1205 is coupled to the open end of the syringe 1201, with the valve housing 1205 having a connecting cap 1206 thereon and an optional floating ball 1210 retained therein. The valve housing 1205 is further configured to liquidly connect to a prime straw 1207 via a fitting 1208. When the prime straw 1207 is removed, a separate tube (not shown) may be connected to the valve housing 1205 for eventual fluid connection to the patient after priming.

The valve housing 1205 is shown coupled to the syringe 1201, with the fill tube 1204 liquidly coupled to the valve housing 1205 via the connecting cap 1206. Also within the valve housing 1205 is a bell-shaped flow controller 1212. Again, the bell-shaped contour of the surface of the flow controller 1212 directs the liquid along the interior walls of syringe 1201 in accordance with the Coandă effect. A central opening in the flow controller 1212 provides a wide channel for air to flow from the syringe 1201 to the prime tube 1207, thereby reducing the velocity of the air moving past the air/liquid interface. In this manner, slow moving air is unlikely to pull liquid in a distal direction, for example under a Bernoulli effect.

Figure 23B:
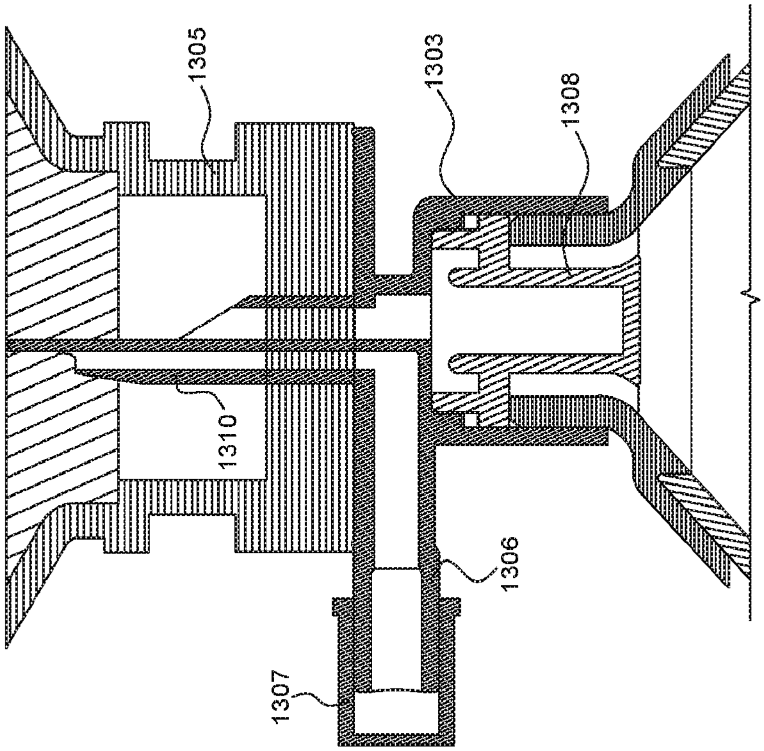
FIG. 23B is a detailed side cross-sectional view of a connection interface of the fill adapter of FIG. 23A.
Figure 23A:
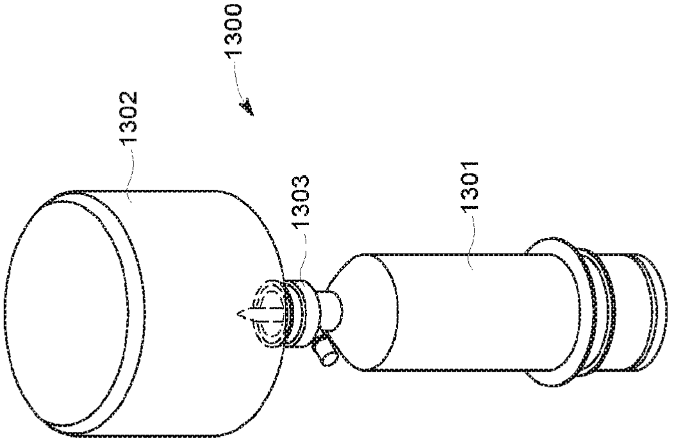
FIG. 23A is a perspective view of a fluid transfer assembly in accordance with another example of the present disclosure.
Figure 23C:
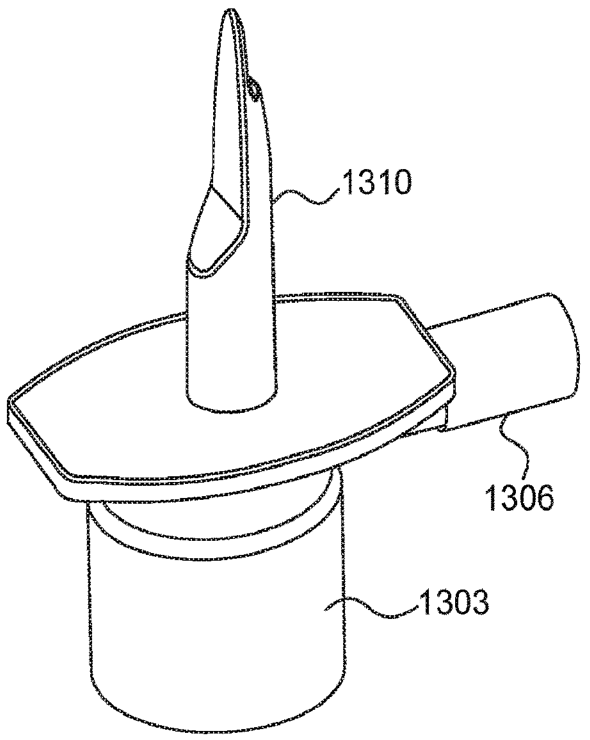
FIG. 23C is a perspective view of a spike adapter of the fluid transfer assembly of FIG. 23A.
Figure 23D:
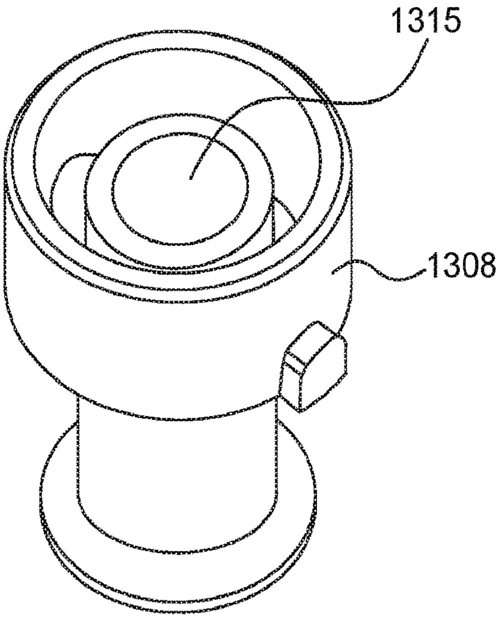
FIG. 23D is a perspective view of a flow controller in accordance with one aspect of the fill adapter of FIG. 23A.

Referring now to FIGS. 23A-23D, a fluid transfer assembly 1300 in accordance with another example of the present disclosure is shown. The fluid transfer assembly 1300 has a syringe 1301, a container 1302, and a spike adapter 1303 configured to directly liquidly connect the syringe 1301 and the container 1302. Specifically, referring to FIG. 23B, the spike adapter 1303 has a spike 1310 capable of piercing a septum or other sealed component of the container 1302. The spike 1310 has two passages formed therethrough, one in fluid connection with the syringe 1301, the other capable of venting air through vent conduit 1306 formed on the spike adapter 1303 into the container 1302, with the vent conduit 1306 being coupled to a vent cap 1307. As liquid passes through the spike 1310 from the container 1302, for example during a vacuum fill procedure, it contacts a flow controller 1308. As detailed in the examples above, the flow controller 1308 is formed so as to direct the liquid flow along the inner surfaces of syringe 1301 during the filling process. As shown in FIG. 23B and FIG. 23D, specifically, the flow controller 1308 may have an inner opening 1315 formed therein, wherein any liquid entering the flow controller 1308 is urged to flow down the peripheral surfaces of the flow controller 1308 to better direct liquid flow along the inner surfaces of syringe 1301.

Figure 24A:
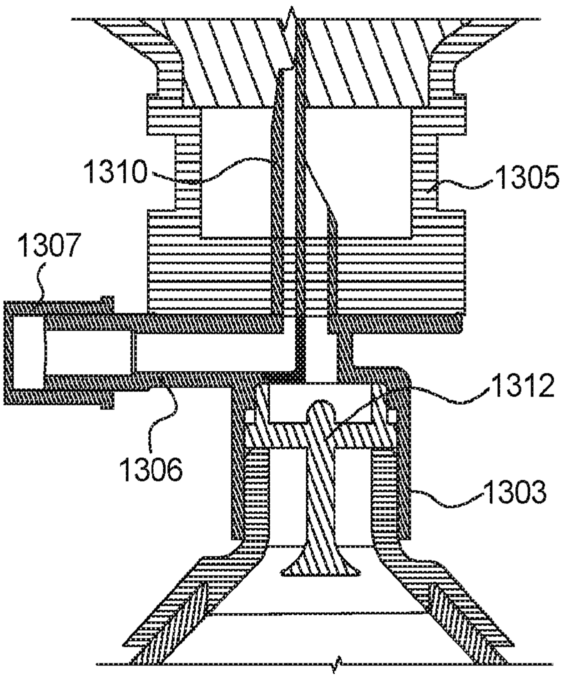
FIG. 24A is a detailed side cross-sectional view of a connection interface in accordance with another example of the fill adapter of FIG. 23A.
Figure 24B:
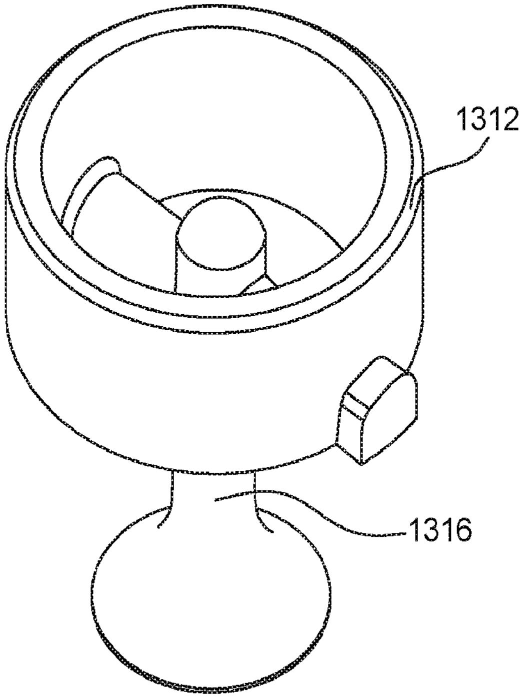
FIG. 24B is a perspective view of a flow controller of the connection interface of FIG. 39A.
Figure 25A:
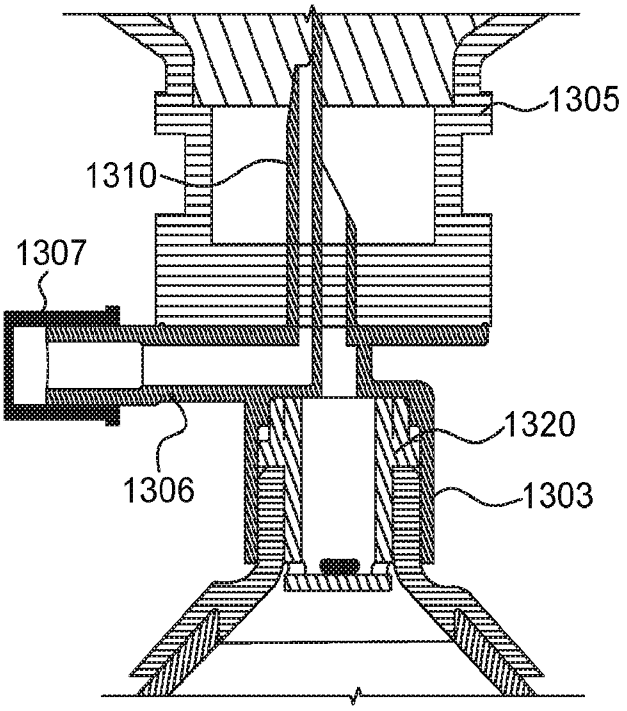
FIG. 25A is a detailed side cross-sectional view of a connection interface in accordance with another example of the fill adapter of FIG. 23A.
Figure 25B:
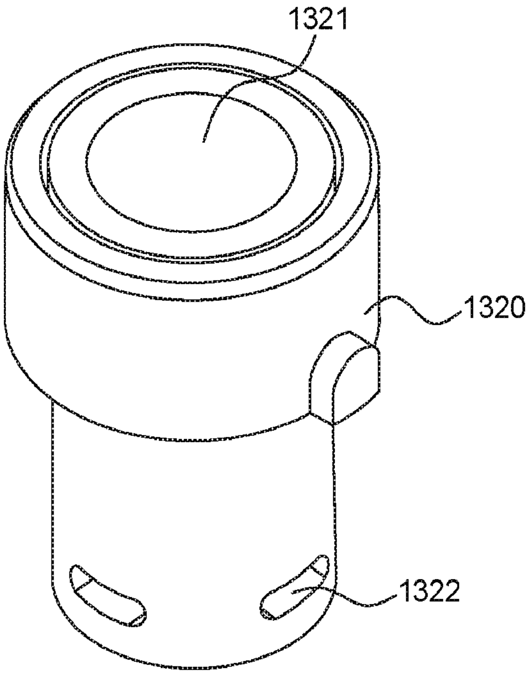
FIG. 25B is a perspective view of a flow controller of the connection interface of FIG. 25A.
Figure 26A:
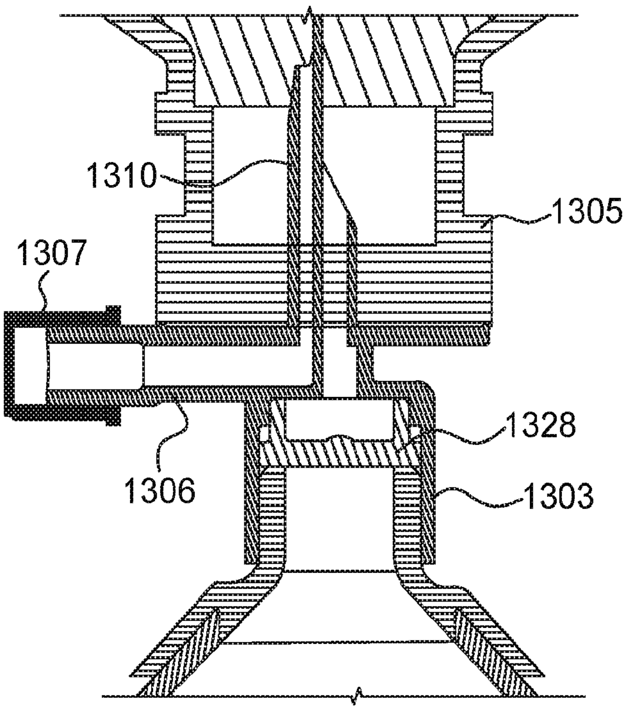
FIG. 26A is a detailed side cross-sectional view of a connection interface in accordance with another aspect of the fill adapter of FIG. 23A.
Figure 26B:
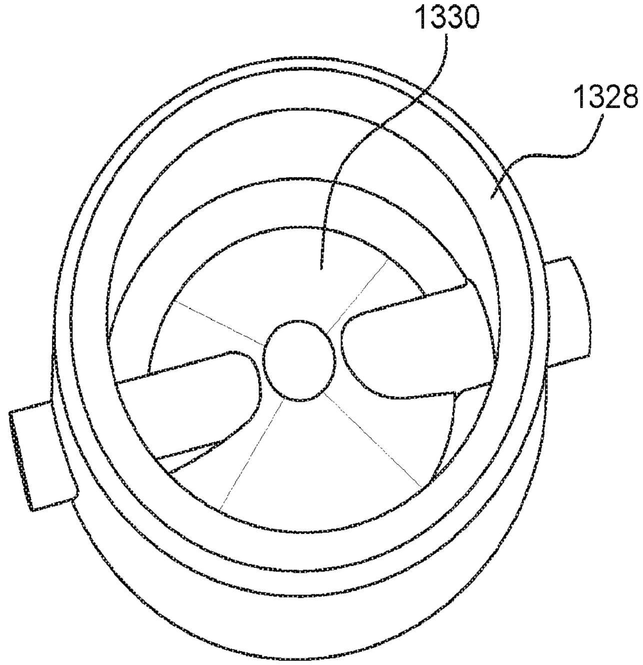
FIG. 26B is a perspective view of a flow controller of the connection interface of FIG. 26A.

While the flow controller 1308 is shown to have an inner opening 1315 formed therein, the flow controller shape and contours in accordance with the disclosure are not limited to such. For example, FIGS. 24A-24B, FIGS. 25A-25B, and FIGS. 26A-26B illustrate alternative flow controllers in accordance with alternative examples of the present disclosure. In particular, FIGS. 24A-24B show a flow controller 1312 having a solid, bell-shaped component 1316 extending therebelow, with the bell-shaped component 1316 configured to direct liquid flow along the inner surfaces of the syringe 1301. FIGS. 25A-25B show a flow controller 1320 having an opening 1321 therein, with a bottom portion of the flow controller 1320 having a plurality of openings 1322 formed therein so as to allow the liquid to pass therethrough at or near the inner surfaces of the syringe 1301. Further, FIGS. 26A-26B show a flow controller 1328 having a dome-shaped insert 1330 retainer therein to encourage the liquid passing therethrough to run along the inner surfaces of the syringe 1301. The insert 1330 may be made from an elastomeric material such that an opening formed by deflecting at least a portion of the insert 1330 as a result of liquid flow can be adjusted.

Referring now to FIGS. 27A-27G, a fluid transfer assembly 1400 in accordance with another example of the present disclosure is shown. Many aspects of the fluid transfer assembly 1400 are similar to those previously discussed with respect to earlier fluid transfer assemblies, but the fluid transfer assembly 1400 utilizes a spool valve 1415 to enable or disable flow to/from a syringe 1401, as will be discussed herein.

Specifically referring to FIGS. 27A-27G, the fluid transfer assembly 1400 has a container 1402 and the syringe 1401, with the container 1402 and the syringe 1401 liquidly coupled via dual respective connector tubes 1403, 1404. A valve housing 1406 is coupled to the syringe 1401, with the valve housing 1406 having a flow controller 1410 therein, a vent cap 1412 configured to vent air to/from the syringe 1401, and a fitting for fluid connection to a low-pressure connector tube 1405. The valve housing 1406 is further liquidly connected to a spool valve 1415, such that the spool valve 1415 enables or disables flow of liquid through the valve housing 1406 and into the syringe 1401. More specifically, the spool valve 1415 is liquidly connected to both connector tubes 1403, 1404. During a syringe filling operation, one end of the connector tube 1405 is coupled to the valve housing 1406, while a second end of the connector tube 1405, having a fitting 1408, is coupled to the spool valve 1415 at a fitting 1409. Within the spool valve 1415 is a valve member 1416 configured to be longitudinally biased to a "closed" position via a spring 1417 or other biasing member. However, when the fitting 1408 of the connector tube 1405 is coupled to the fitting 1409, a portion of the fitting 1408 urges valve member 1416 from a "closed" position (shown in FIG. 27D) to the "open" position (shown in FIG. 27B), thereby allowing liquid to flow from the connector tube 1403 into the syringe 1401, and further allowing air to from the syringe 1401 to pass through the connector tube 1405 and into the connector tube 1404 for passage to the container 1402. In this manner, the fluid transfer assembly 1400 is a closed system where no air from outside the fluid transfer assembly 1400 is introduced. Rather, the air exchange between the container 1402 and the syringe 1401 during a filling operation of the syringe 1401 is handled by the connector tubes 1403, 1404, and 1405, and only sterile air within the fluid transfer assembly 1400 is exchanged. The closed system of the fluid transfer assembly 1400 may be suitable for transferring liquids where prevention of contamination of the liquid by outside air is desired, such as with chemotherapy drugs.

Figure 27A:
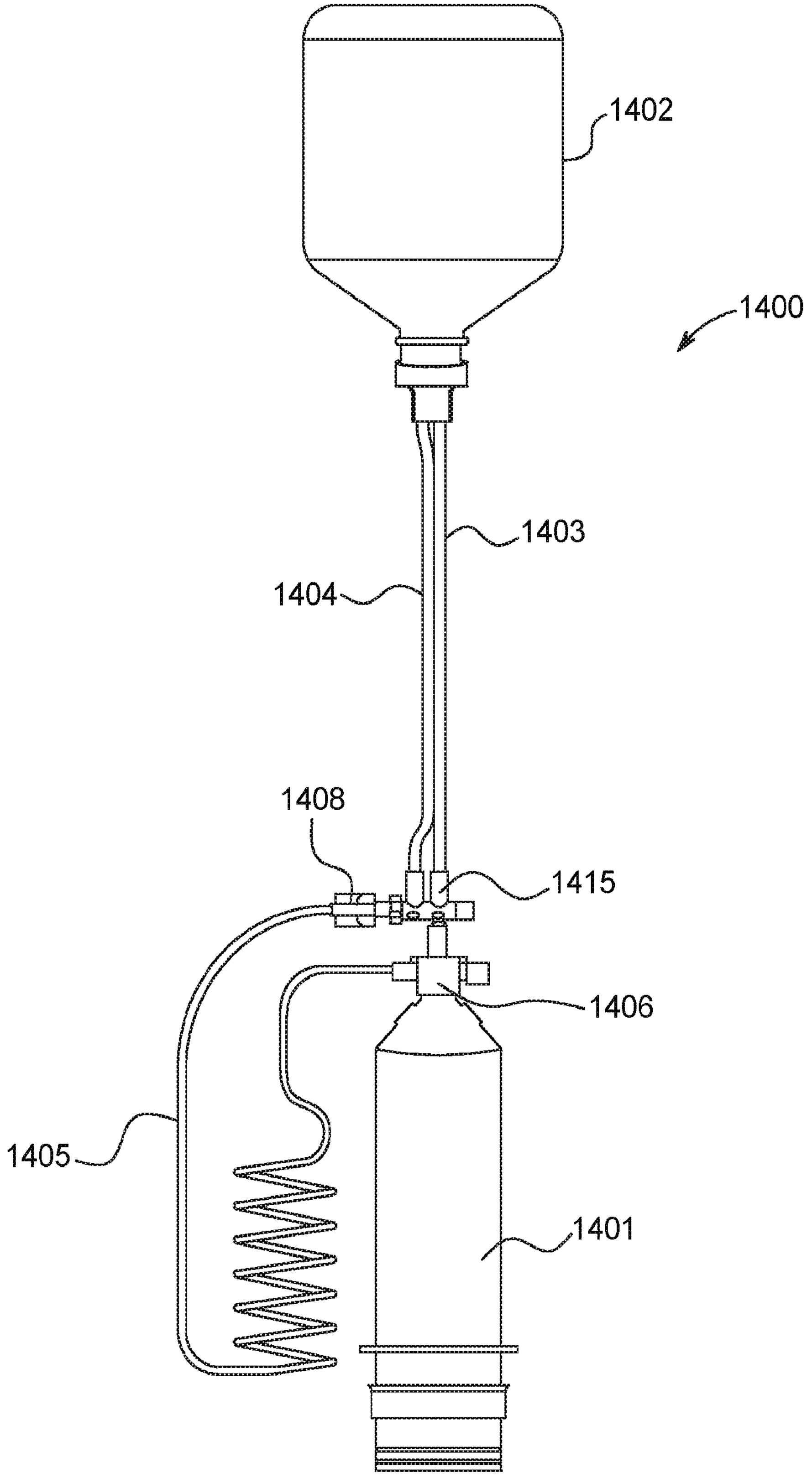
FIG. 27A is a perspective view of a fluid transfer assembly in accordance with another example of the present disclosure.
Figure 27C:
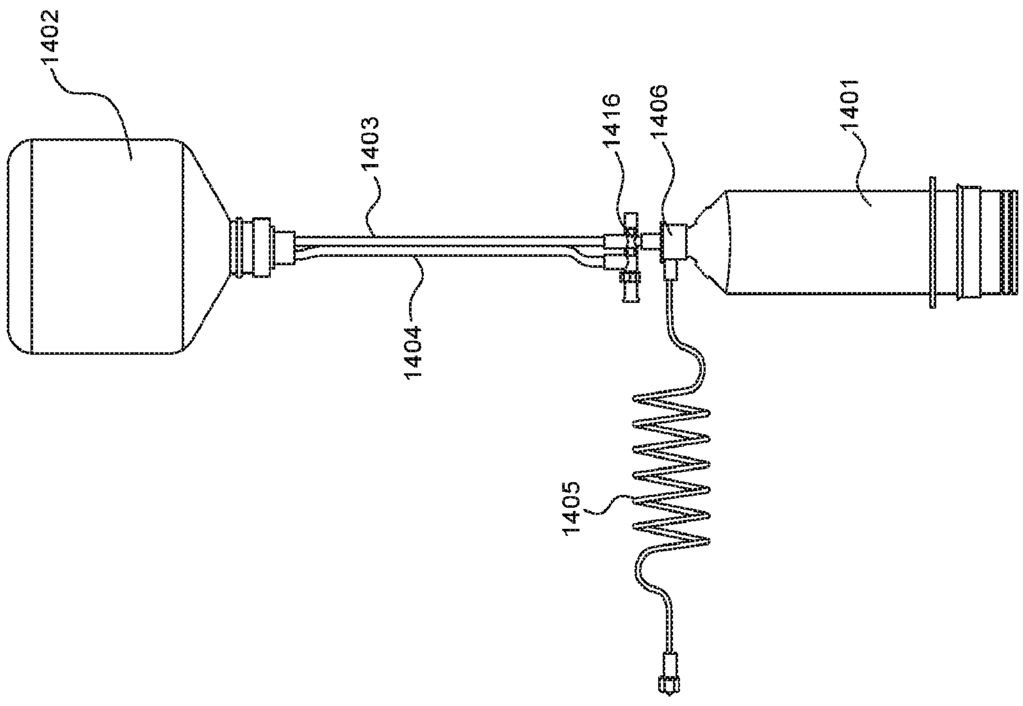
FIG. 27C is another perspective view of a fluid transfer assembly of FIG. 27A.
Figure 27B:
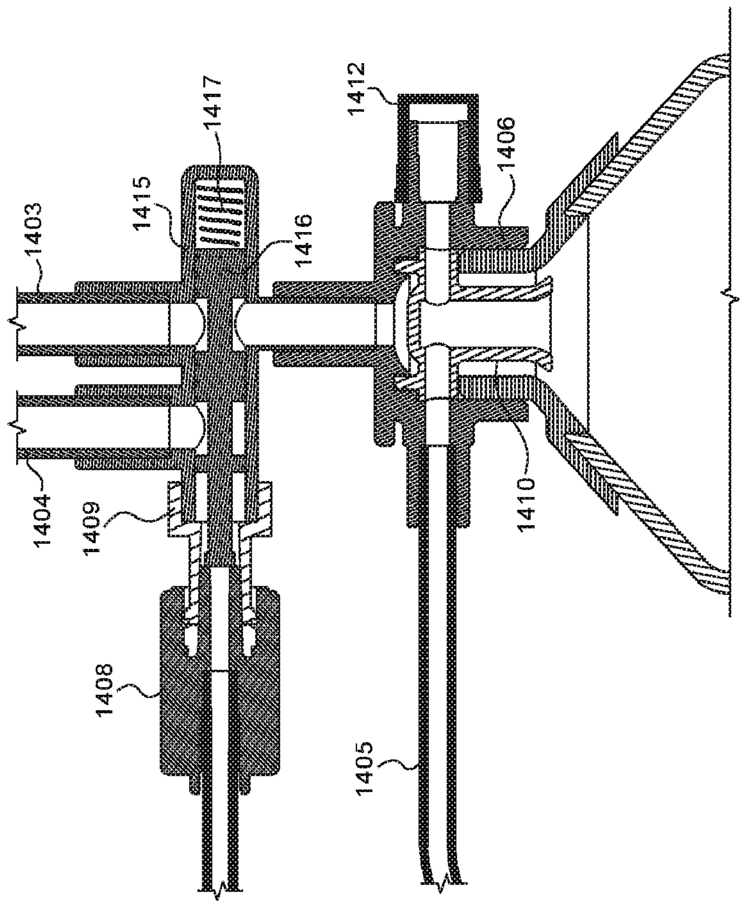
FIG. 27B is a detailed side cross-sectional view of a connection interface of the fill adapter of FIG. 27A.
Figure 27E:
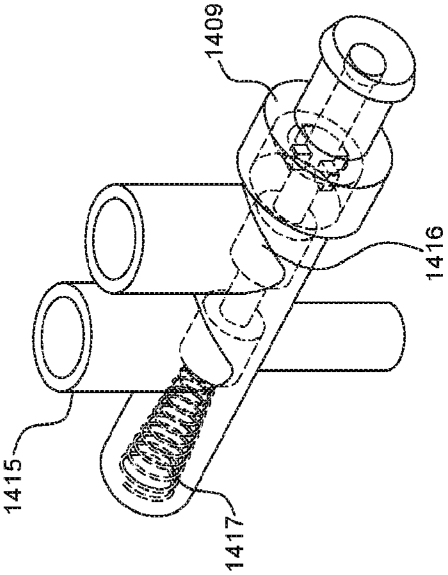
FIG. 27E is a perspective view of a spool valve of the fluid transfer assembly of FIG. 27A.
Figure 27D:
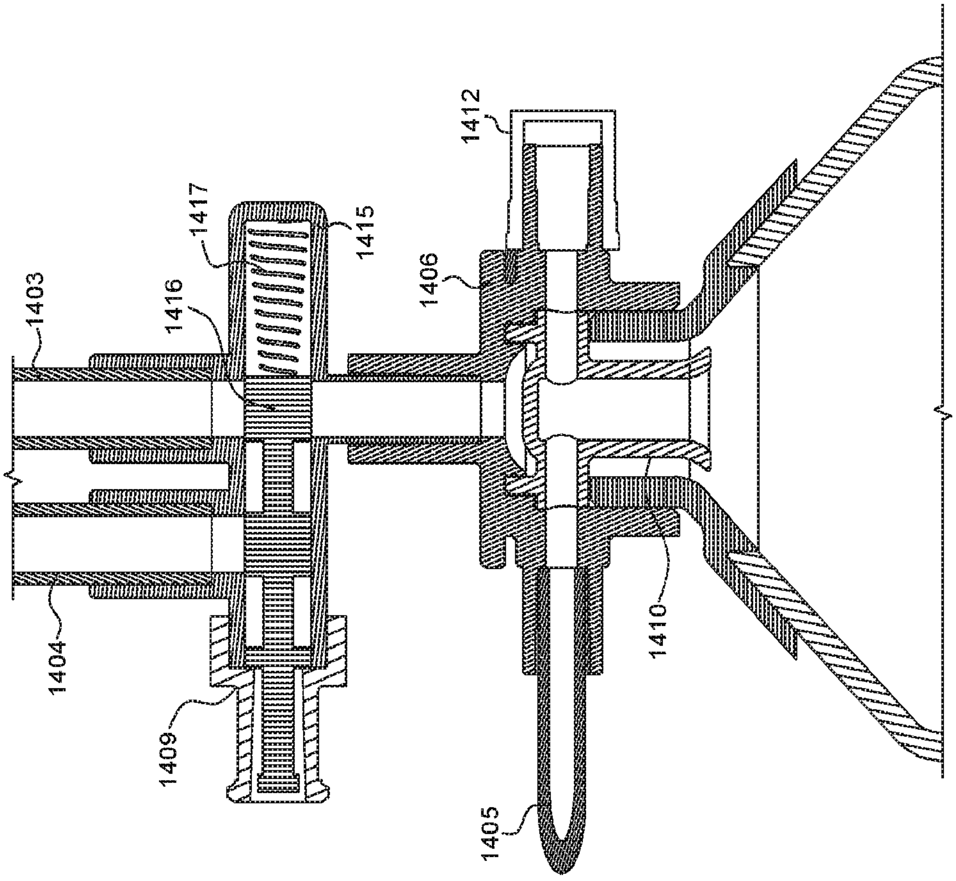
FIG. 27D is a detailed side cross-sectional view of a connection interface of the fill adapter of FIG. 27C.
Figure 27F:
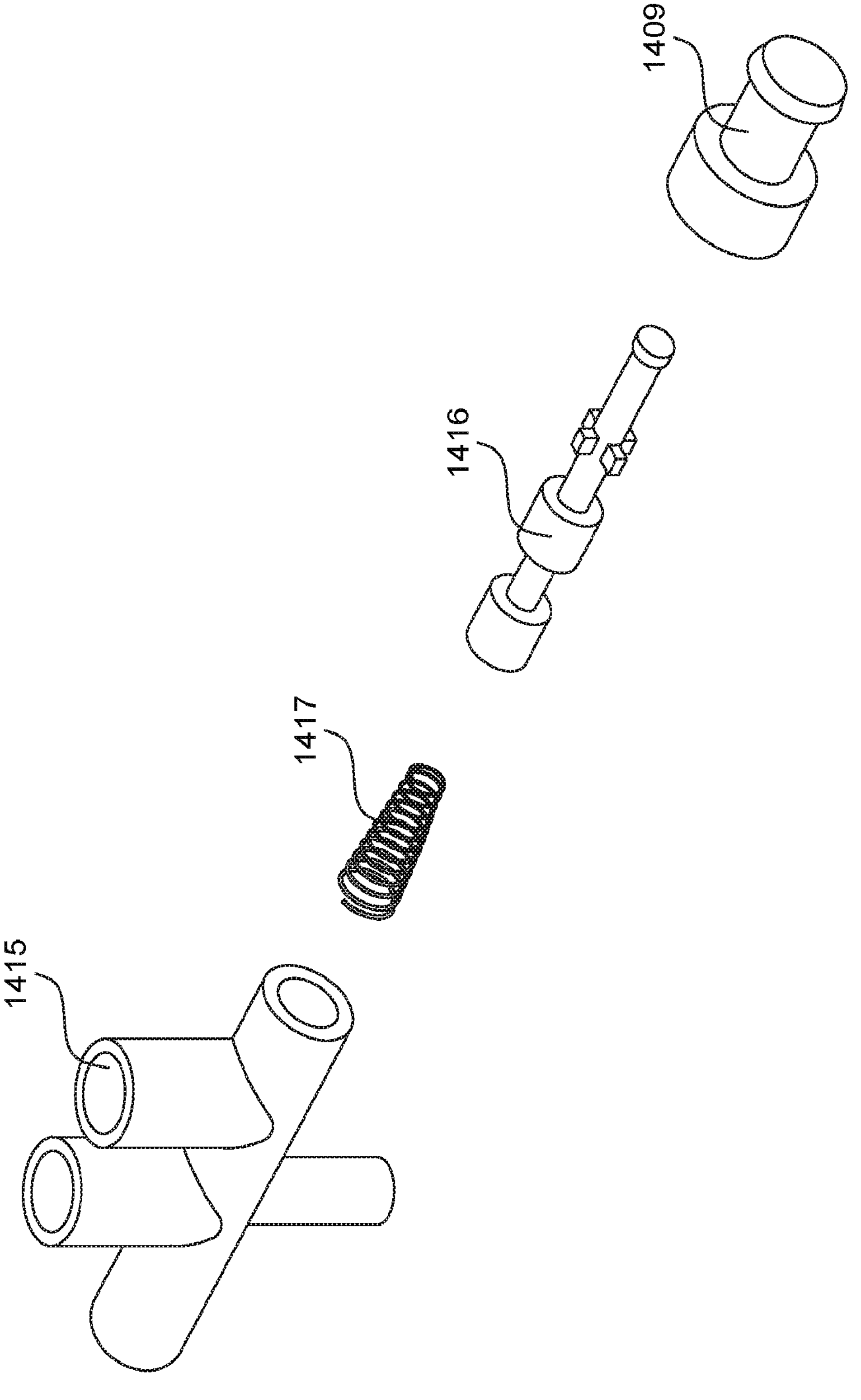
FIG. 27F is an exploded perspective view of the spool valve of FIG. 27E.
Figure 27G:
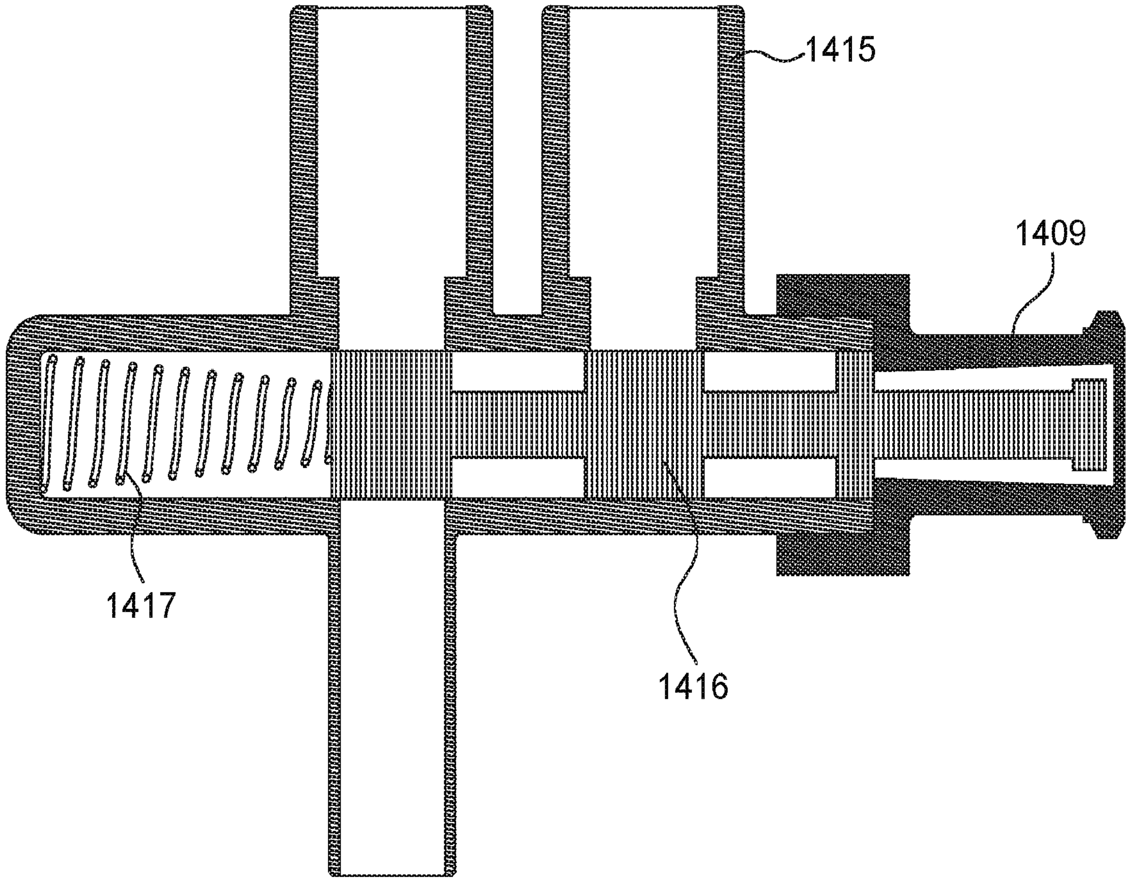
FIG. 27G is a detailed side cross-sectional view of the spool valve of FIG. 27E.

Referring to FIGS. 27C-27D, when the fitting 1408 is removed from the spool valve 1415, the valve member 1416 is no longer urged against the spring 1417. Accordingly, the spring 1417 biases the valve member 1416 to the "closed" position (FIG. 27D), thereby preventing the flow of liquid from the connector tube 1403 into the syringe 1401, and also blocking the passage of air or liquid out of the connector tube 1404.

Figure 28A:
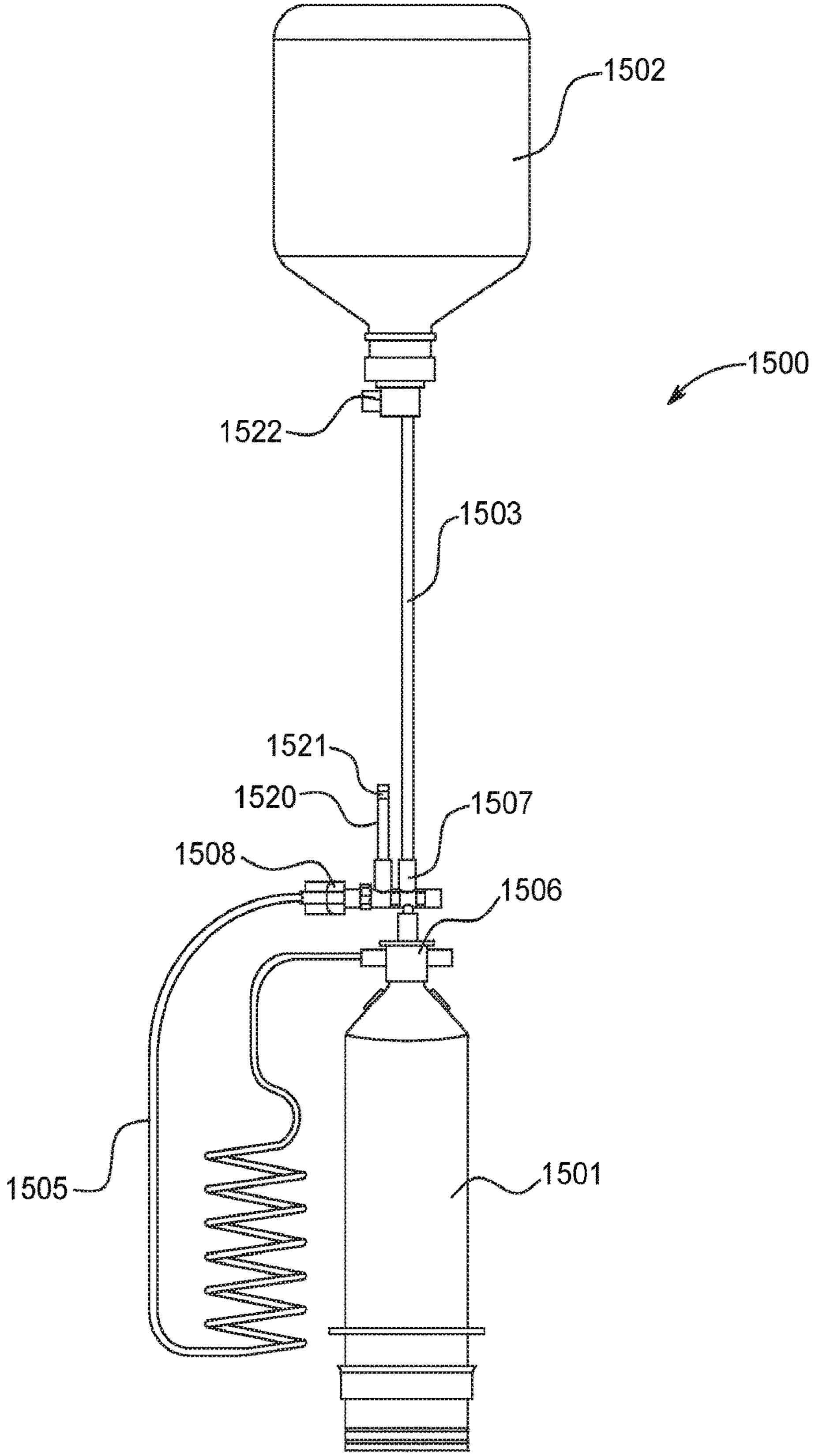
FIG. 28A is a perspective view of a fluid transfer assembly in accordance with another example of the present disclosure.
Figure 28B:
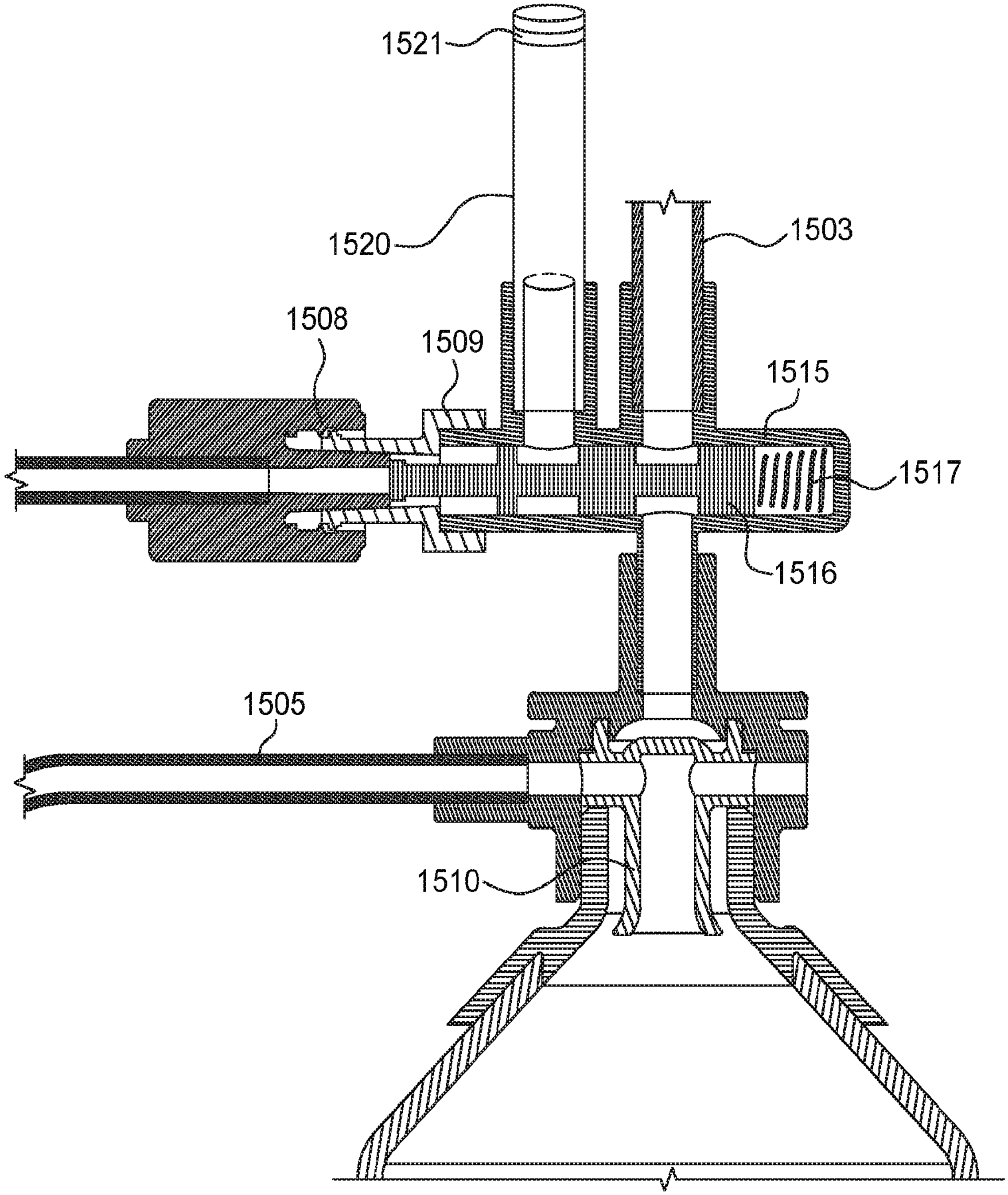
FIG. 28B is a detailed side cross-sectional view of a connection interface of the fill adapter of FIG. 28A.

Referring to FIGS. 28A-28B, a fluid transfer assembly 1500 in accordance with another aspect of the present disclosure is shown. Many aspects of the fluid transfer assembly 1500 are similar to those previously discussed above with respect to the fluid transfer assembly 1400, but the fluid transfer assembly 1500 does not require the use of a secondary tube (such as the tube 1404 in FIGS. 27A-27G) extending between a syringe 1501 and a container 1502, as described herein.

As shown in FIGS. 28A-28B, the fluid transfer assembly 1500 has the container 1502 and the syringe 1501, with the container 1502 and the syringe 1501 liquidly coupled via a single connector tube 1503. The connector tube 1503 is liquidly coupled to the container 1502 via a vented coupler 1522, which has an air filter therein so as to allow air within the container 1502 to vent during transfer of liquid between the container 1502 and the syringe 1501. A valve housing 1506 is coupled to the syringe 1501, with the valve housing 1506 having a flow controller 1510 therein, and a fitting for fluid connection to a low-pressure connector tube 1505. The valve housing 1506 is further liquidly connected to a spool valve 1515, such that the spool valve 1515 enables or disables flow of liquid through the valve housing 1506 and into the syringe 1501. More specifically, the spool valve 1515 is liquidly connected to the connector tube 1503. During a syringe filling operation, one end of the connector tube 1505 is coupled to the valve housing 1506, while a second end of the connector tube 1505, having a fitting 1508, is coupled to the spool valve 1515 at a fitting 1509. Within the spool valve 1515 is a valve member 1516 configured to be longitudinally biased to a "closed" position via a spring 1517. However, when the fitting 1508 of the connector tube 1505 is coupled to the fitting 1509, a portion of the fitting 1508 urges the valve member 1516 to the "open" position, thereby allowing liquid to flow from the connector tube 1503 into the syringe 1501. The valve member 1516 may be solid or hollow. In a hollow configuration, the valve member 1516 may allow air to pass through an inner portion of the valve 1515, while liquid flowing through the connector tube 1503 into the syringe 1501 is allowed to pass over the outer surfaces thereof.

In addition to the valve member 1516 allowing liquid to pass between the container 1502 and the syringe 1501 when in the "open" configuration, the valve member 1516 also enables air to flow from the syringe 1501, through the connector tube 1505, and out of a vented air filter 1521 located on a prime tube 1520 coupled to the spool valve 1515. Specifically, during transfer of liquid from the container 1502 into the syringe 1501, air is purged out of the syringe 1501 through connector tube 1505. The air filter 1521, which can be, for example, a 0.2 micron air filter, allows the purged air to vent to atmosphere. When the fitting 1508 is removed from the spool valve 1515, the valve member 1516 is no longer urged against the spring 1517. Accordingly, the spring 1517 biases the valve member 1516 to the "closed" position, thereby preventing the flow of liquid from the connector tube 1503 into the syringe 1501. In the "closed" position, the valve member 1516 may also block the passage of air or liquid out of the air filter 1521, but it may alternatively allow the air passage to remain open when disconnected from the connector tube 1505.

Figure 29:
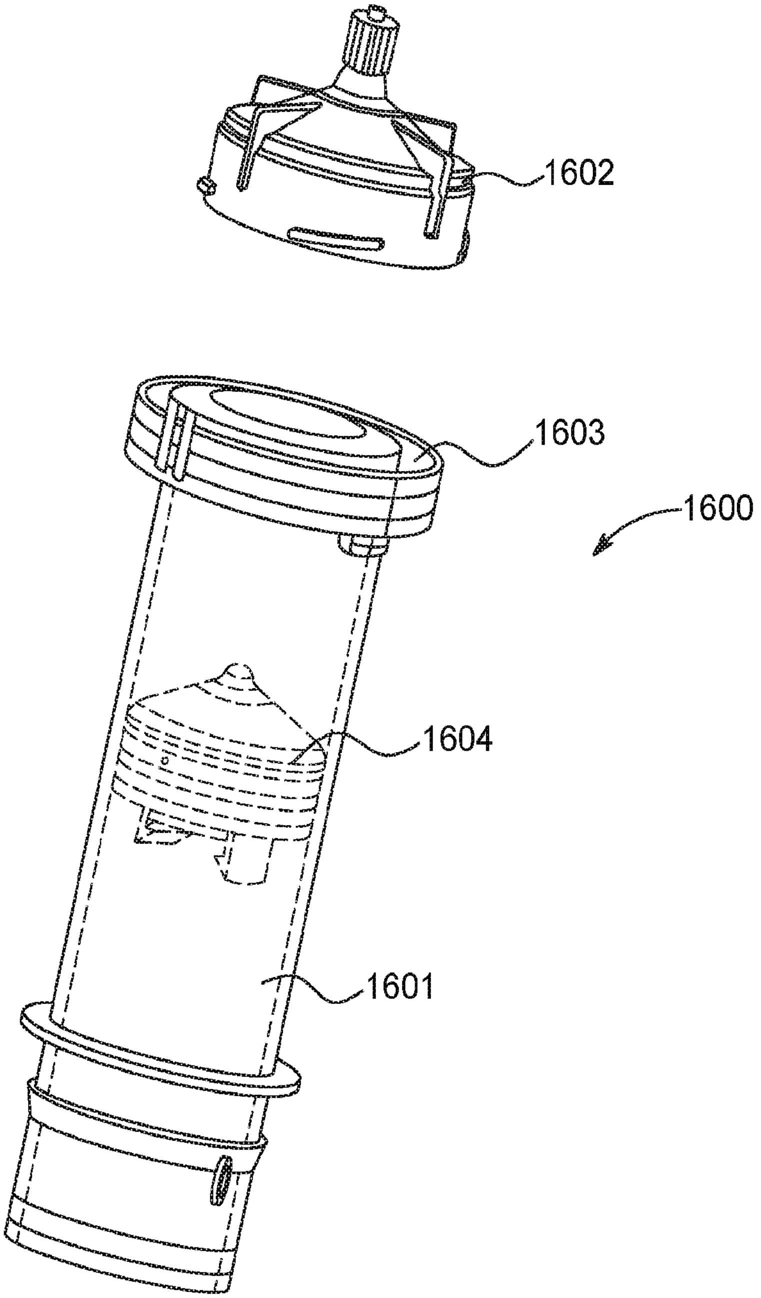
FIG. 29 is an exploded perspective view of a syringe assembly in accordance with another example of the present disclosure.

With reference to FIG. 29, a syringe 1600 in accordance with another aspect of the disclosure is shown. The syringe 1600 is configured to receive a flexible rolling diaphragm, such as the rolling diaphragm syringe 12*a* shown in FIG. 2A, within an interior space of the syringe 1600. The syringe 1600 has a base adapter 1601 having a plunger 1604 disposed therein, as well as a connector 1603 on a distal end thereof. A syringe tip 1602 is configured for removable connection with the connector 1603 via, for example, a threaded connection. The syringe tip 1602 is desirably a disposable, single-use item. However, the base adapter 1601 is a multi-use item, capable of use between many procedures and/or patients. Accordingly, instead of the entire syringe assembly being single-use (as is currently common), the syringe 1600 enables only the syringe tip 1602 to be replaced between uses. Furthermore, different types of syringe tips could be utilized with one type of base adapter.

Figure 30B:
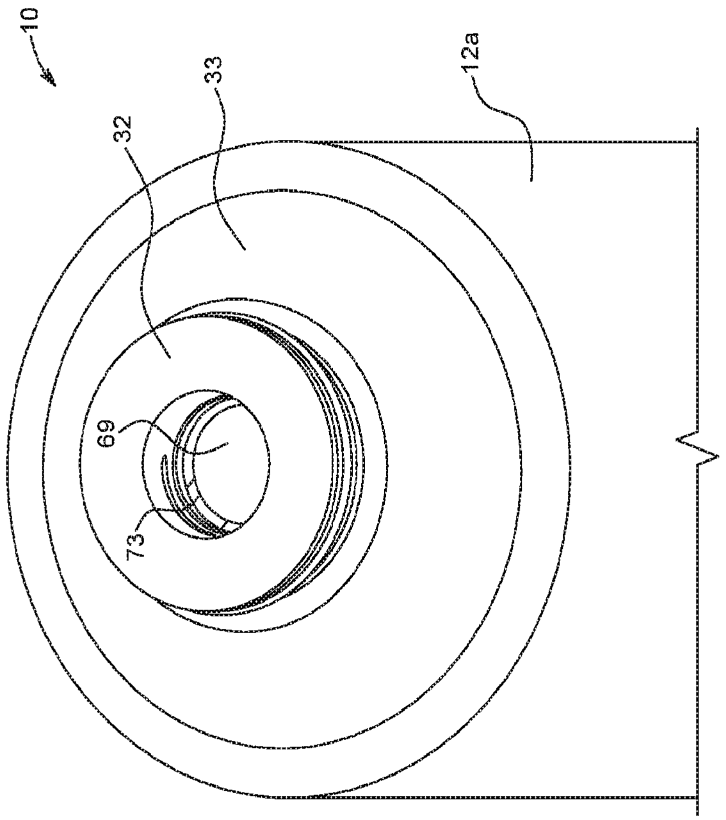
FIG. 30B is a detailed top perspective view of the syringe and fill adapter of FIG. 30A.
Figure 30A:
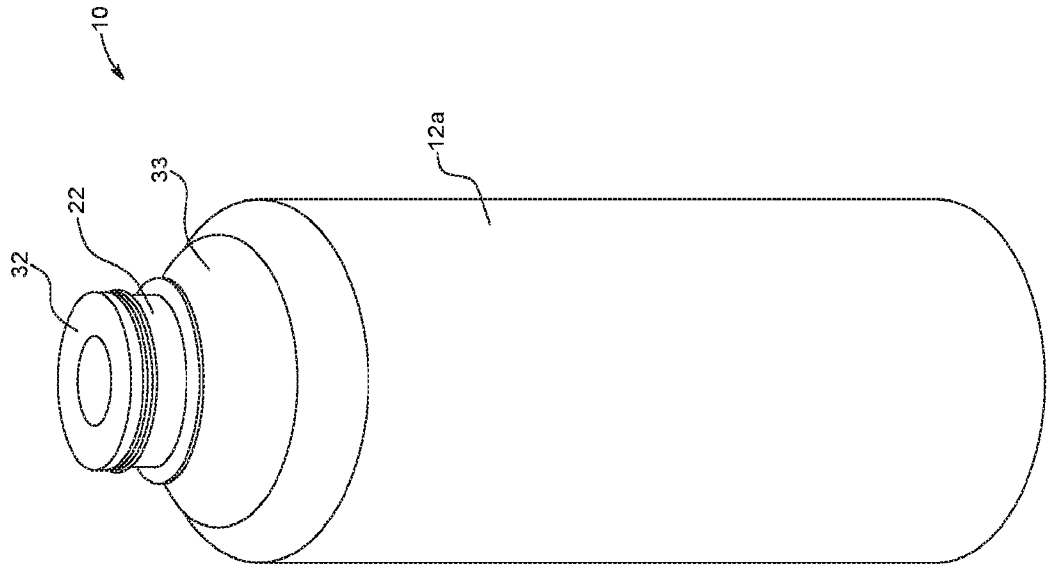
FIG. 30A is a perspective view of a syringe with a fill adapter in accordance with another example of the present disclosure.
Figure 30D:
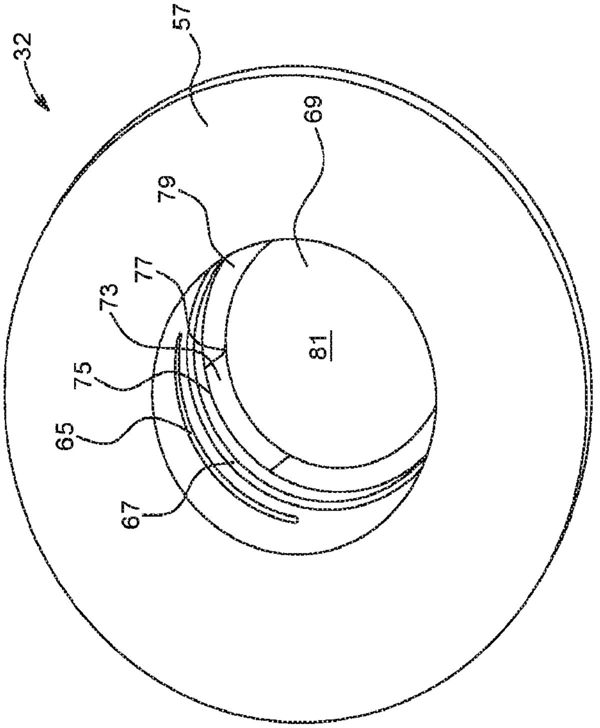
FIG. 30D is a top perspective view of the fill adapter shown in FIG. 30A removed from the syringe.
Figure 30C:
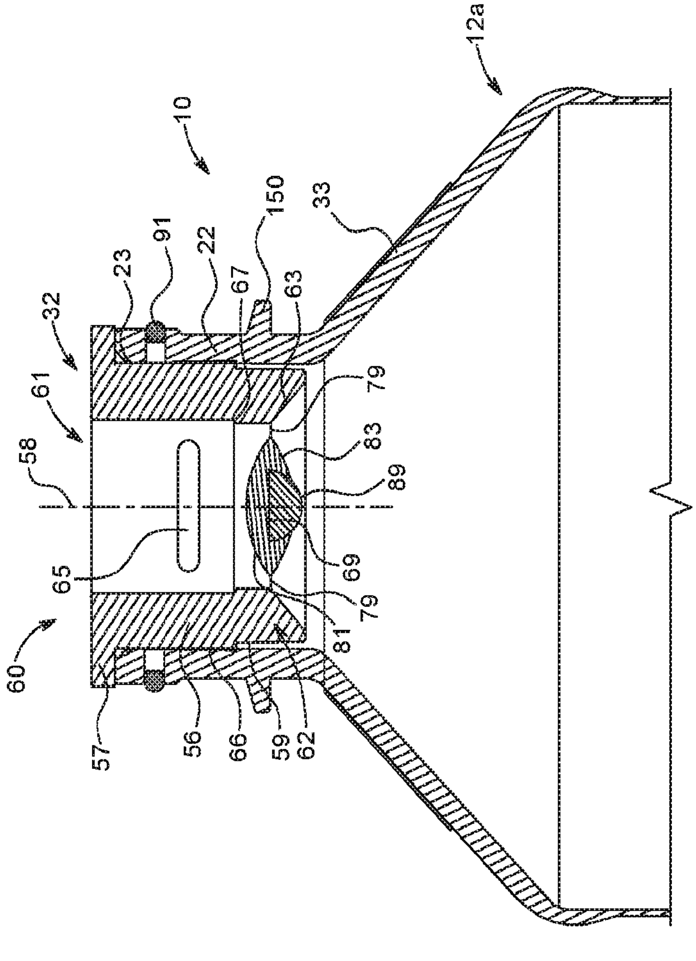
FIG. 30C is a side cross-sectional view of the syringe and fill adapter of FIG. 30A.

With reference to FIGS. 30A-30C, a fluid transfer assembly 10 is illustrated in accordance with another example of the present disclosure. The fluid transfer assembly 10 is configured to facilitate transfer of liquid from a second liquid container, such as a bottle or a bag (not shown), to a first liquid container, such as a syringe 12*a* described herein with reference to FIG. 2A. In other examples, the first liquid container may be the syringe 12*b* described herein with reference to FIG. 2B.

With continued reference to FIGS. 30A-30C, the fluid transfer assembly 10 includes a fill adapter 32 configured for facilitating a transfer of liquid between the two liquid containers, such as from the second liquid container to the syringe 12*a*. The fill adapter 32 may be removably connectable to the syringe 12*a*, such as the syringe neck 22 of the syringe 12*a*. In some examples, the fill adapter 32 may be non-removably connected to the syringe 12*a*, such as by being monolithically formed therewith, or by being non-removably attached thereto, such as by adhesive, welding, interference fit, or other mechanical connection means. The fill adapter 32 may have a unitary, single piece structure, or it may be formed from two or more components removably or non-removably coupled together. In various aspects, fill adapter 32 may flow between 2 mL/s to 20 mL/s of liquid while filling syringe 12*a*.

With reference to FIG. 30C, the fill adapter 32 has a substantially cylindrical body 56 that is configured to be received within the open distal end 23 of the syringe neck 22. A flange 57 extends radially outward from the body 56 at a distal end 60. In some examples, an outer diameter of the flange 57 may substantially correspond to an outer diameter of the syringe neck 22 such that the fill adapter 32 is flush with the syringe neck 22. In other examples, the outer diameter of the flange 57 may be larger or smaller than the outer diameter of the syringe neck 22. A longitudinal length of the body 56 along the longitudinal axis 58 may correspond to a longitudinal length of the syringe neck 22 such that a proximal end 62 of the fill adapter 32 terminates at a proximal end of the syringe neck 22 and before the syringe sidewall 20 transitions from the syringe neck 22 to a conical portion 33. In some examples, the longitudinal length of the body 56 may be longer or shorter than a transition point where the syringe sidewall 20 transitions from the syringe neck 22 to the conical portion 33. In various examples, the longitudinal length of body 56 may be between 6 mm to 100 mm.

The fill adapter 32 may be dimensioned such that it fits snuggly within the open distal end 23 of the syringe neck 22. For example, an outer sidewall 66 of the fill adapter 32 may be engaged with an inner sidewall of the syringe neck 22 due to an interference fit between an outer sidewall 66 of the fill adapter 32 and an inner sidewall 26 of the syringe neck 22. The fill adapter 32 may be removably or non-removably engaged with the syringe neck 22. In some examples, the fill adapter 32 and the syringe neck 22 may be removably or non-removably connected to one another by way of clips, fasteners, adhesive, welding, or other mechanical connection means. In some examples, an outer surface of the body 56 may have one or more recesses 59 to facilitate insertion of the fill adapter 32 into the open distal end 23 of the syringe neck 22. In various examples, an outer diameter of the body 56 of the fill adapter may be between 2.6 mm and 26 mm.

With continued reference to FIG. 30C, the fill adapter 32 has a central bore 61 extending through the body 56 along the longitudinal axis 58. The central bore 61 is configured for allowing liquid communication between the second liquid container and the interior of the syringe 12*a*. In some examples, the central bore 61 may have a uniform diameter throughout the length thereof. In other examples, at least a portion of the central bore 61 may narrow or widen in a direction from the distal end 60 to the proximal end 62 of the body 56. For example, an angled portion 63 of the central bore 61 may widen in a direction from the distal end 60 to the proximal end 62 of the body 56, such as shown in FIG. 30C. In some examples, an angle of the angled portion 63 may correspond to an angle of the conical portion 33 of the syringe 12*a*. In other examples, the angle of the angled portion 63 may have a larger or smaller angle than the angle of the conical portion 33 of the syringe 12*a*. In various examples, an angle of the angled portion 63 may be between 10 degrees and 80 degrees relative to the longitudinal axis of the body 56.

One or more slots 65 may extend through the sidewall of the body 56. In some examples, a plurality of slots 65 may extend through the sidewall of the body 56 at equal or unequal angular intervals therebetween. The slots 65 may be provided at a same axial position relative to one another, or one or more of the slots 65 may be offset axially relative to the remaining slots 65. In some examples, a ledge 67 may protrude radially inward from an inner surface of the central bore 61. The ledge 67 may be positioned proximally or distally of the one or more slots 65. The ledge 67 may be continuous or discontinuous in a circumferential direction of the central bore 61. The slots 65 and/or the ledge 67 interrupt the flow of fluid along an inner sidewall of the central bore 61. In this manner, the slots 65 and/or the ledge 67 assist in guiding the fluid flowing through the fill adapter 32 toward a central portion of the bore 61 and away from the inner sidewall of the bore 67 such that the fluid can flow over a flow controller 69, as described herein.

With continued reference to FIG. 30C, the fill adapter 32 may have the flow controller 69 disposed within the central bore 61. The flow controller 69 may be positioned at the proximal end 62 of body 56. In some examples, the flow controller 69 is connected to an inner surface of the central bore 61 by one or more spokes 73 (shown in FIG. 30D). As shown in FIG. 30D, each of the spokes 73 has a first end 75 connected to the body 56 of the fill adapter 32 and a second end 77 connected to the flow controller 69. A gap 79 between the body 56 of the fill adapter 32 and the flow controller 69 is configured to allow liquid to flow therethrough and into the interior of the syringe 12*a*.

The flow controller 69 may be positioned such that an outer edge of the flow controller 69 is aligned with a distal end of the angled portion 63. In this manner, liquid that is deflected by the flow controller 69 will be deflected toward the angled portion 63. As described herein, due to the characteristics of the Coandă effect, liquid will be attracted to the angled surface of the angled portion 63 of the fill adapter 32 and will continue flowing down the inner sidewall of the syringe 12*a*.

Figure 31B:
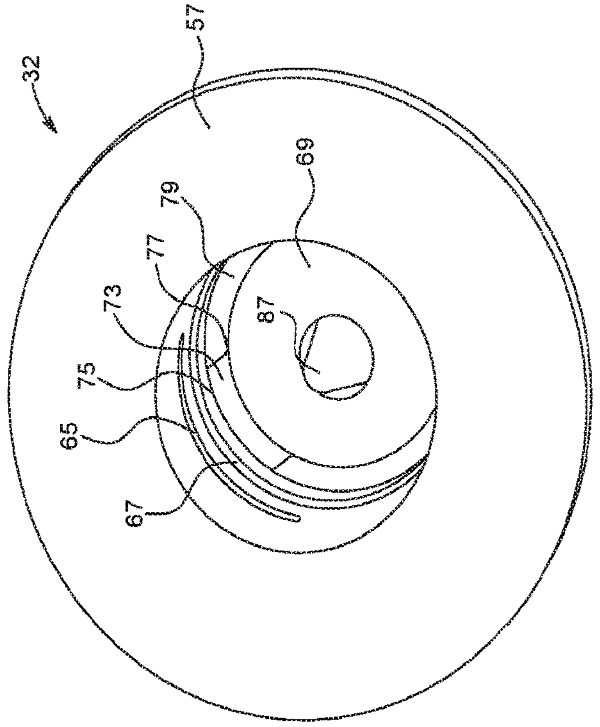
FIG. 31B is a top perspective view of the fill adapter shown in FIG. 31A removed from the syringe.
Figure 31A:
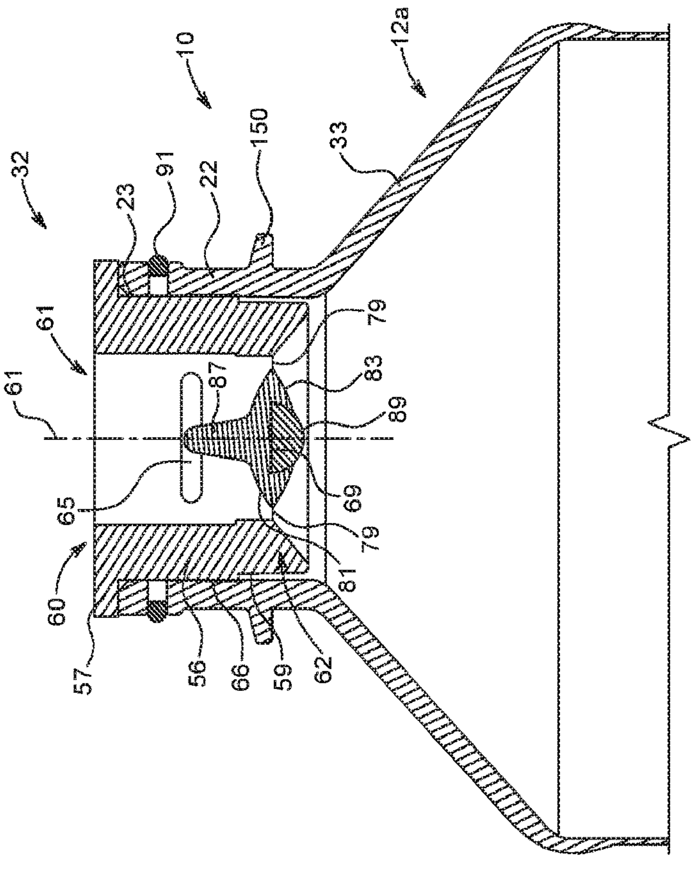
FIG. 31A is a side cross-sectional view of a syringe and a fill adapter in accordance with another example of the present disclosure.

With reference to FIG. 30D, and with continued reference to FIG. 30C, the flow controller 69 may have a curved distal surface 81 that is configured to divert liquid flowing onto the flow controller 69 in a radially outward direction toward the gap 79. The distal surface 81 may have a convex shape having uniform or non-uniform curvature. In some examples, the flow controller 69 may have a curved proximal surface 83. The proximal surface 83 may have a convex shape with a protrusion 89 in a central portion thereof. The protrusion 89 may protrude in a proximal direction from the proximal surface 83. In some examples, such as shown in FIGS. 31A-31B, a central portion of the distal surface 81 may have a flow diverter 87. The flow diverter 87 may extend distally relative to the distal surface 81. The flow diverter 87 may be configured to divert the liquid flowing through the central bore 61 of the fill adapter 32 toward outer edges of the flow controller 69 such that the liquid flows through the gap 79.

In some examples, the syringe neck 22 may have a sealing member, such as an O-ring 91. The O-ring 91 is configured to sealingly engage a cap (not shown) removably connectable to the syringe neck 22 of the syringe 12*a*. An outer portion of the syringe neck 22 may have a flange 150 configured for interacting with the cap for removably retaining the cap with the syringe neck 22. In some examples, the fill adapter 32 may be removably or non-removably connected to the cap such that the fill adapter 32 is removable from the syringe 12*a* with the removal of the cap. In other examples, the fill adapter 32 is provided separate from the cap such that the fill adapter 32 remains connected to the syringe 12*a* when the cap is removed from the syringe 12*a*.

During the filling process, a liquid from the second liquid container (not shown) above the syringe 12*a* is gravity-fed or vacuum-fed to the fill adapter 32. As the liquid flows through the central bore 61 of the fill adapter 32, the liquid contacts the flow controller 69. Due to the convex shape of the distal surface 81 of the flow controller 69, the liquid will be directed radially outward to flow through the gap 79. Due to the bell-shaped angled portion 63, the liquid is naturally attracted to flow along the conical portion 33 of the syringe 12*a* before flowing down the sidewall 20. This flow along the inside surface of the syringe 12*a* helps to reduce turbulence as the liquid fills the syringe 12*a*, which aides in reducing air bubbles from forming as the syringe 12*a* is filled. Simultaneously, air is displaced from the syringe interior and escapes into the second fluid container through the gap 79. Air/liquid exchange within the syringe 12*a* occurs substantially simultaneously through the central bore 61, without any flow hesitation or gurgling due to uneven flow characteristics.

With reference to FIGS. 32A-32D, a cap 122 may be provided on the syringe neck 22 of the syringe 12*a*. The cap 122 is configured to enclose the distal end 18 of the syringe 12*a*. The cap 122 is removably connected to the syringe neck 22 of the syringe 12*a*, for example via a threaded connection, a snap-fit connection, a friction-fit connection, or any other suitable removable connection mechanism. In some examples, the fill adapter 32 may be removably or non-removably connected to the cap 122 such that the fill adapter 32 is removable from the syringe 12*a* with the removal of the cap 122. In other examples, the fill adapter 32 is provided separate from the cap 122 such that the fill adapter 32 remains connected to the syringe 12*a* when the cap 122 is removed from the syringe 12*a*.

The cap 122 includes a port 124 configured for connection to tubing that is in liquid communication with a second liquid container (not shown) for filling the syringe 12*a* with liquid from the second liquid source. In other examples, the port 124 may be configured for connection to tubing connected to a catheter, needle, or other liquid delivery connection (not shown) inserted into a patient at a vascular access site to deliver liquid from the syringe 12*a* to the patient.

Figure 32B:
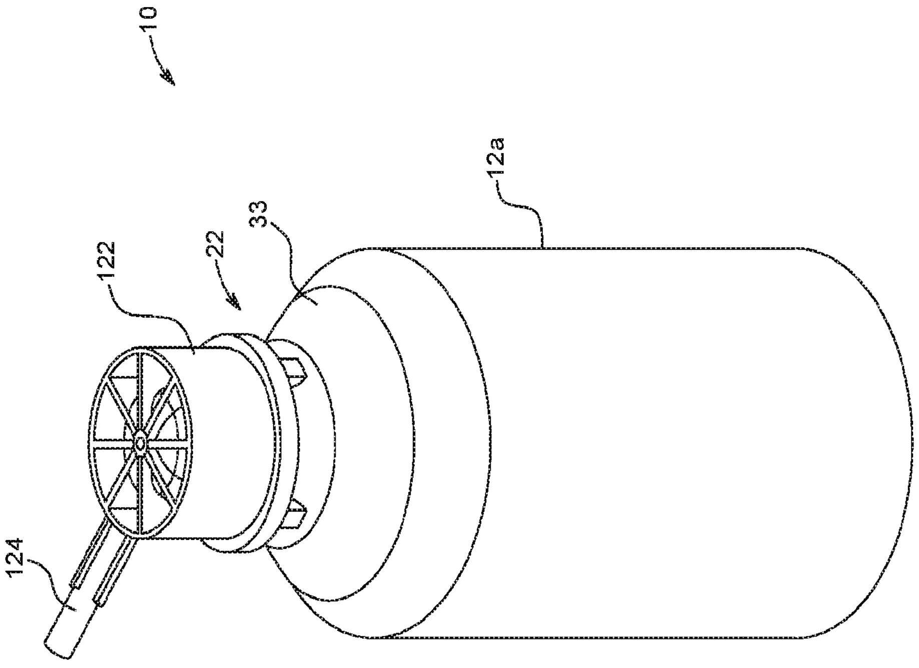
FIG. 32B is a perspective view of the syringe, fill adapter, and cap of FIG. 32A in assembled form.
Figure 32A:
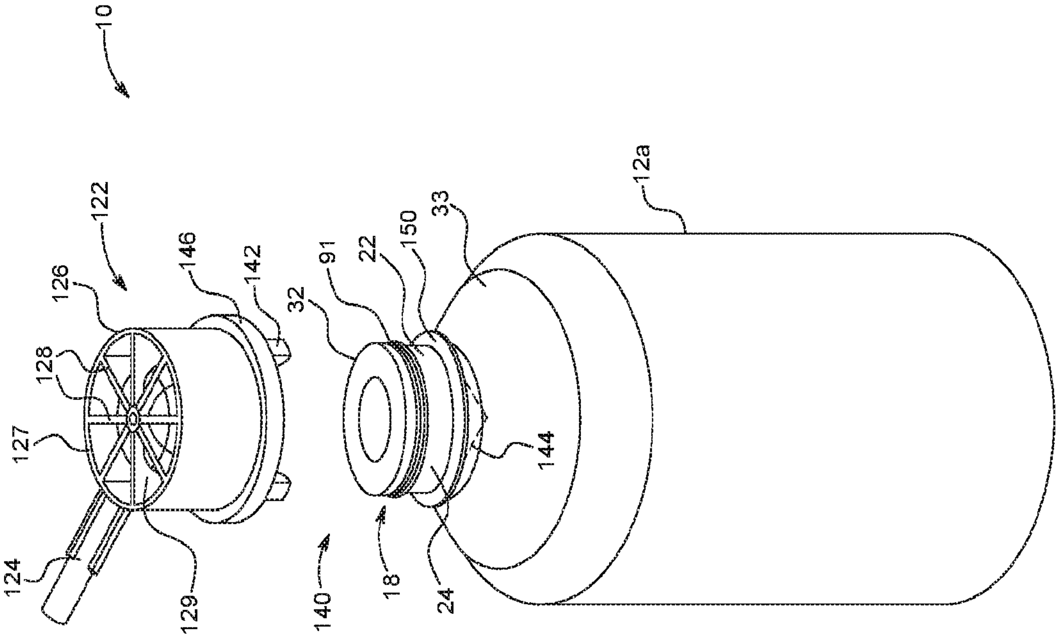
FIG. 32A is an exploded perspective view of a syringe, fill adapter, and cap in accordance with another example of the present disclosure.

In some examples, the port 124 may be provided on a radial side of the cap 122. A high crack pressure valve (not shown) may be provided on the cap 122 to permit flow of liquid through the cap 122 into the syringe 12*a* when a predetermined crack pressure is reached or exceeded, while preventing flow through the cap 122 when the head height of pressure is less than the crack pressure. In one example, the high crack pressure valve may be a slit valve or other conventional crack pressure valve. The cap 122 may have at least one gasket around an inner surface of the cap 122 for engaging an outer surface 24 of the syringe neck 22. In some examples, the gasket, such as the O-ring 91, may be provided on the outer surface 24 of the syringe neck 22. The O-ring 91 is configured to create a liquid-tight seal between the outer surface 24 of the syringe neck 22 and the inner surface of the cap 122. With reference to FIGS. 32A-32B, a distal surface 126 of the cap 122 may be configured as a substantially flat surface.

With continued reference to FIGS. 32A-32B, the cap 122 is removably connectable to the syringe 12*a* by way of a connection mechanism 140. The connection mechanism 140 is configured to securely retain the cap 122 connected to the syringe neck 22 of the syringe 12*a*, such as shown in FIG. 32B, and allow the cap 122 to be disconnected from the syringe neck 22 of the syringe 12*a* with rotation of the cap 122 about its longitudinal axis relative to the syringe 12*a*. The connection mechanism 140 has one or more tabs 142 on the cap 122 that interact with one or more cams 144 on the syringe 12*a*. When the cap 122 is connected to the syringe 12*a*, rotation of the cap 122 relative to the syringe 12*a* causes the one or more tabs 142 to interact with the one or more cams 144 to deflect the tabs 142 radially outward such that the cap 122 can be removed from the syringe 12*a*.

Figure 32D:
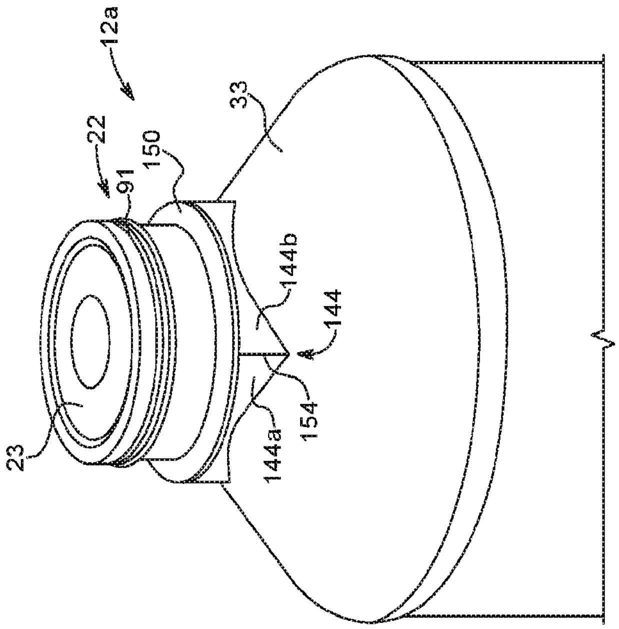
FIG. 32D is a perspective view of the syringe of FIG. 32A.
Figure 32C:
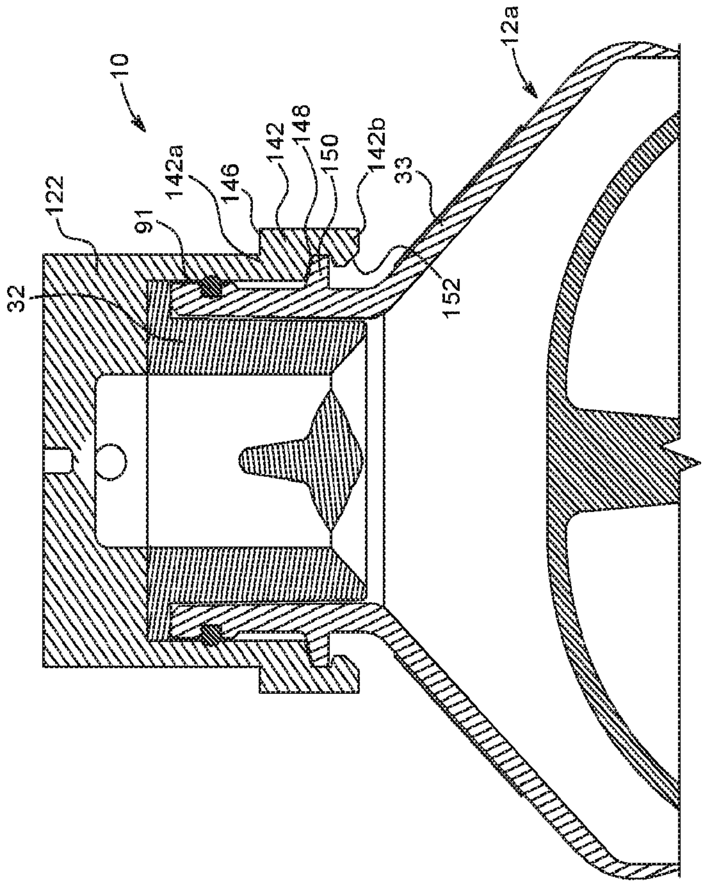
FIG. 32C is a side cross-sectional view of the syringe, fill adapter, and cap of FIG. 32A.

With reference to FIG. 32C, the tabs 142 protrude in a proximal direction from a skirt 146 that extends around an outer circumference of the cap 122. The tabs 142 may be spaced apart from one another at equal or unequal angular intervals around the skirt 146. Each tab 142 has a first end 142*a* connected to the skirt 146 and a second end 142*b* protruding proximally from the skirt 146. The second end 142*b* of each tab 142 is deflectable relative to the first end 142*a* when the tab 142 engages the cam 144. The second end 142*b* of each tab 142 has a recess 148 that is configured to engage a flange 150 extending radially outward from the outer surface 24 of the syringe neck 22. The flange 150 may extend around a portion or an entire circumference of the syringe neck 22. When engaged with the flange 150, the recess 148 prevents the cap 122 from being removed from the syringe 12*a*. Each tab 142 may have a beveled edge 152 that is configured to engage a distal surface of the flange 150 to deflect the tab 142 in a radially outward direction when the cap 122 is being connected to the syringe neck 22. After the beveled edge 152 clears the flange 150, each tab 142 can deflect back to engage the recess 148 with the flange 150, thereby connecting the cap 122 with the syringe neck 22 of the syringe 12*a*.

With reference to FIG. 32D, the cams 144 are positioned proximally of the flange 150. In some examples, a plurality of cams 144 is spaced apart from one another around an outer circumference of the syringe neck 22 below the flange 150. The cams 144 may be spaced apart from one another in equal or unequal angular intervals. For example, FIG. 32D shows a syringe 12*a* with four cams 144 spaced apart from each other at 90 degrees. In this manner, rotation of the cap 122 of less than 90 degrees causes the tabs 142 to engage the cams 144 to disconnect the cap 122 from the syringe 12*a*. Each cam 144 has a pair of ramp surfaces 144*a*, 144*b* that come together at an edge 154. In some examples, the edge 154 may terminate at an outer end of the flange 150. The ramp surfaces 144*a*, 144*b* define an engagement surface for the second end 142*b* of the tabs 142 to contact when the cap 122 is to be disconnected from the syringe 12*a*.

To remove the cap 122 from the syringe 12*a*, the cap 122 can be rotated in a first direction (e.g., clockwise) or a second direction (e.g., counterclockwise) about its longitudinal axis relative to the syringe longitudinal axis. During such rotational movement of the cap 122, the second end 142*b* of each tab 142 engages one of the ramp surfaces 144*a*, 144*b* of each cam 144. Due to the angled configuration of the ramp surfaces 144*a*, 144*b*, continued rotation of the cap 122 causes the second end 142*b* of the tabs 142 to be deflected relative to the first end 142*a* (and the flange 150), thereby allowing the tabs 142 to move past the flange 150. In this manner, the cap 122 can be disconnected from the syringe neck 22 with a simple rotation of the cap 122 relative to the syringe 12*a*.

Figure 33B:
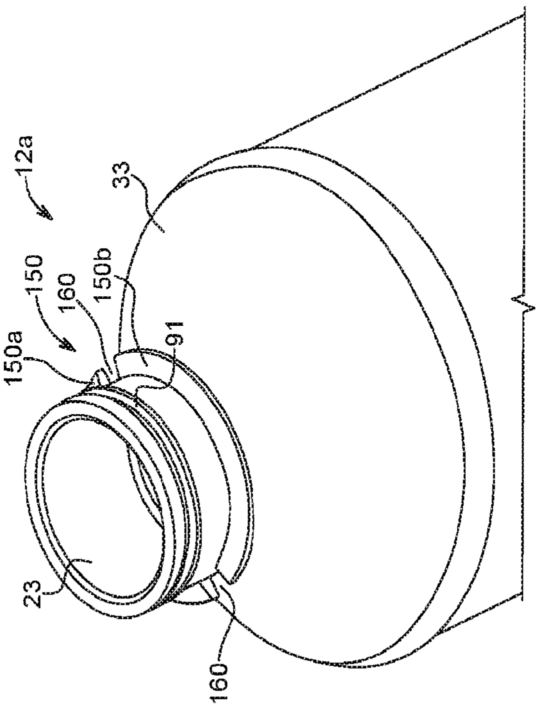
FIG. 33B is a perspective view of the syringe of FIG. 33A.
Figure 33A:
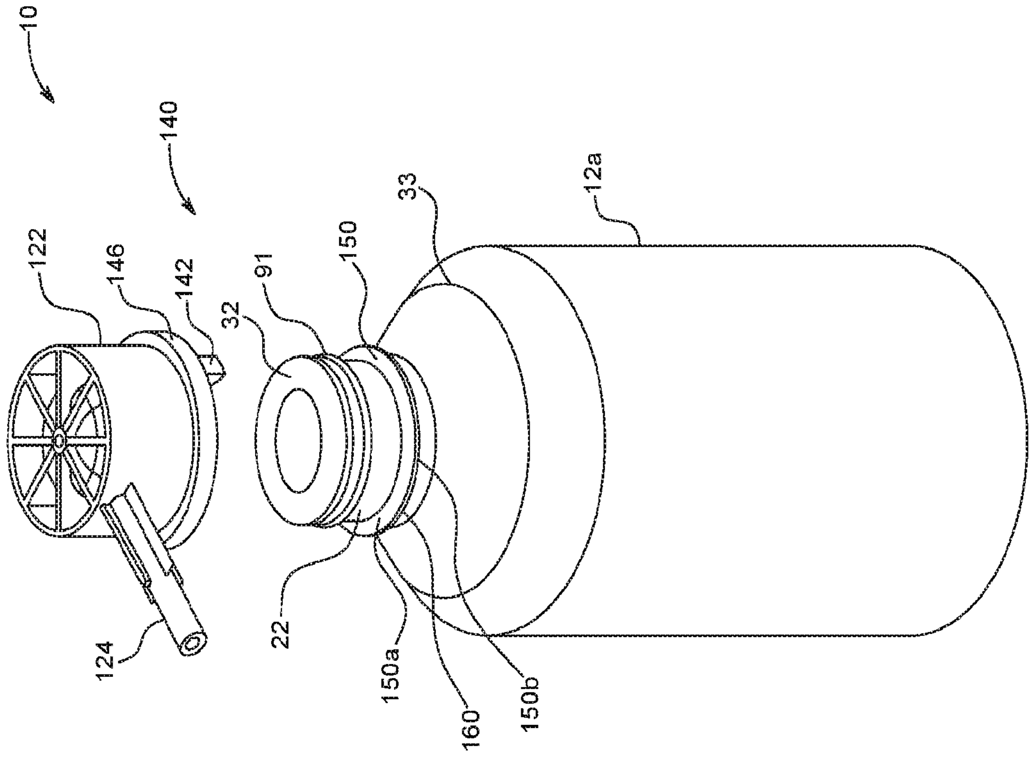
FIG. 33A is an exploded perspective view of a syringe, fill adapter, and cap in accordance with another example of the present disclosure.
Figure 33C:
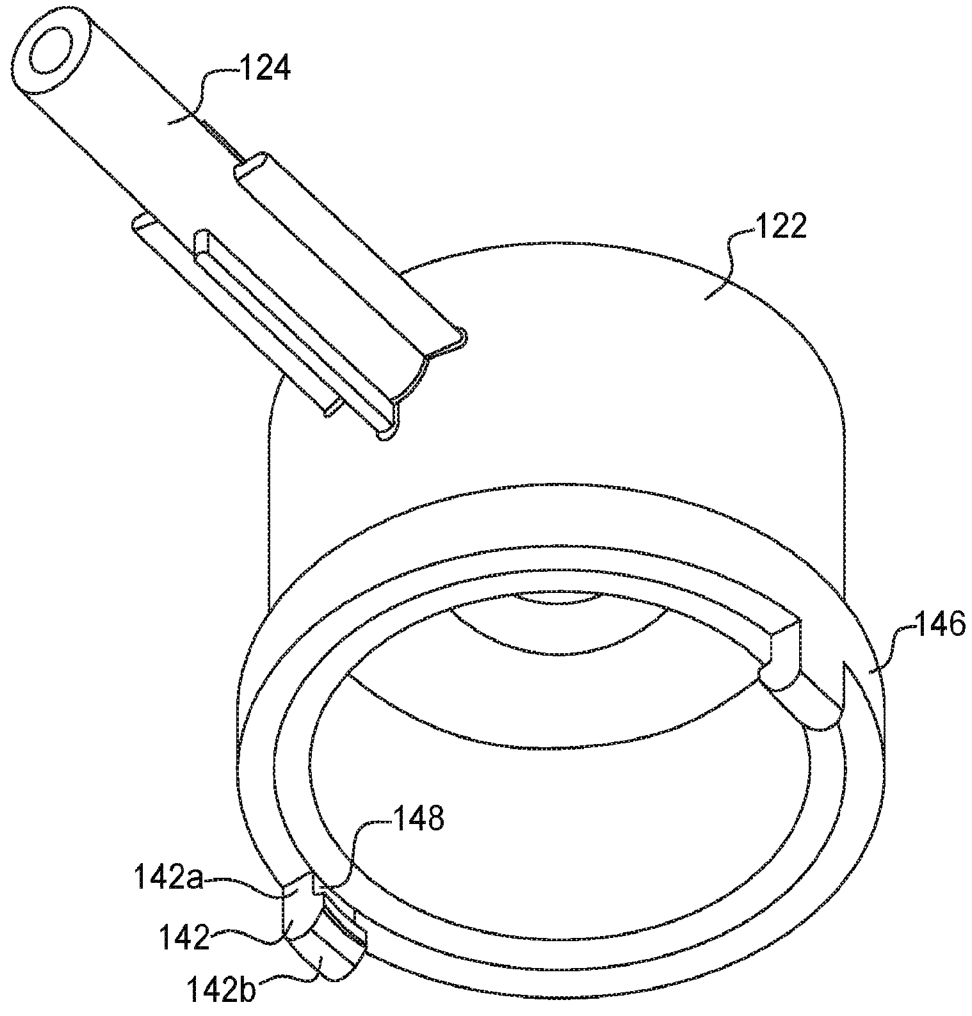
FIG. 33C is a perspective view of the cap of FIG. 33A.

With reference to FIGS. 33A-33C, a fluid transfer assembly 10 is shown in accordance with another example of the present disclosure. The components of the fluid transfer assembly 10 shown in FIGS. 33A-33C are substantially similar to the components of the fluid transfer assembly 10 described herein with reference to FIGS. 32A-32D. As the previous discussion regarding the fluid transfer assembly 10 generally shown in FIGS. 32A-32D is applicable to the examples shown in FIGS. 33A-33C, only the relative differences between the two liquid transfer assemblies 10 are discussed hereinafter.

The cap 122 is removably connectable to the syringe 12*a* by way of a connection mechanism 140. In some examples, the fill adapter 32 may be removably or non-removably connected to the cap 122 such that the fill adapter 32 is removable from the syringe 12*a* with the removal of the cap 122. In other examples, the fill adapter 32 is provided separate from the cap 122 such that the fill adapter 32 remains connected to the syringe 12*a* when the cap 122 is removed from the syringe 12*a*. The connection mechanism 140 is configured to securely retain the cap 122 connected to the syringe neck 22 of the syringe 12*a*, and allow the cap 122 to be disconnected from the syringe neck 22 of the syringe 12*a* with rotation of the cap 122 about its longitudinal axis relative to the syringe 12*a* to a removal position at which the cap 122 can be separated from the syringe 12*a* with axial movement of the cap 122 relative to the syringe 12*a*. The connection mechanism 140 has one or more tabs 142 on the cap 122 that interact with a flange 150 on the syringe 12*a*.

With reference to FIG. 33C, the one or more tabs 142 on the cap 122 protrude in a proximal direction from a skirt 146 that extends around an outer circumference of the cap 122. The tabs 142 may be spaced apart from one another at equal or unequal angular intervals around the skirt 146. Each tab 142 has a first end 142*a* connected to the skirt 146 and a second end 142*b* protruding proximally from the skirt 146. Desirably, the second end 142*b* of each tab 142 is deflectable relative to the first end 142*a*. The second end 142*b* of each tab 142 has a recess 148 that is configured to engage the flange 150 extending radially outward from the outer surface 24 of the syringe neck 22 (shown in FIG. 33B).

With reference to FIG. 33B, the flange 150 may extend around a portion of the outer circumference of the syringe neck 22. In some examples, the flange 150 may be formed as a continuous member having a first end and a second end separated by a gap 160. In other examples, the flange 150 may be formed from a plurality of segments separated from one another by two or more gaps 160. For example, the flange 150 may have two flange segments 150*a*, 150*b* separated by two gaps 160. The flange segments 150*a*, 150*b* may have equal or unequal length and may be separated by gaps 160 having equal or unequal width. Each gap 160 defines a removal position at which the tabs 142 can be aligned for removal of the cap 122 from the syringe neck 22, as discussed herein. Desirably, the number of tabs 142 corresponds to the number of gaps 160. When engaged with the flange 150, the recess 148 prevents the cap 122 from being removed from the syringe 12*a*. Each tab 142 may have a beveled edge 152 that is configured to engage a distal surface of the flange 150 to deflect the tab 142 in a radially outward direction when the cap 122 is being connected to the syringe neck 22. After the beveled edge 152 clears the flange 150, each tab 142 can deflect back to engage the recess 148 with the flange 150, thereby connecting the cap 122 with the syringe neck 22 of the syringe 12*a*.

To remove the cap 122 from the syringe 12*a*, the cap 122 can be rotated in a first direction (e.g., clockwise) or a second direction (e.g., counterclockwise) about its longitudinal axis relative to the syringe longitudinal axis. During such rotational movement of the cap 122, the tabs 142 can be rotated to the removal position by aligning the tabs 142 with the gaps 160 between the flange segments 150*a*, 150*b*. When the cap 122 is rotated to the removal position, the gaps 160 create a clearance space for the tabs 142 to clear the flange segments 150*a*, 150*b*. The cap 122 can be disconnected from the syringe neck 22 with axial movement of the cap 122 relative to the syringe 12*a*.

Figure 34B:
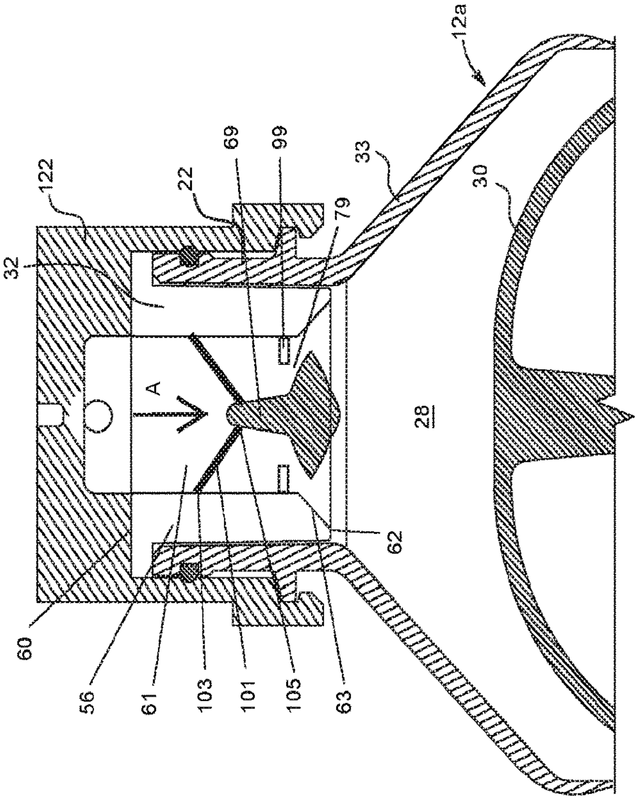
FIG. 34B is a side cross-sectional view of the syringe and the fill adapter of FIG. 34A, showing the flow controller in an open position.
Figure 34A:
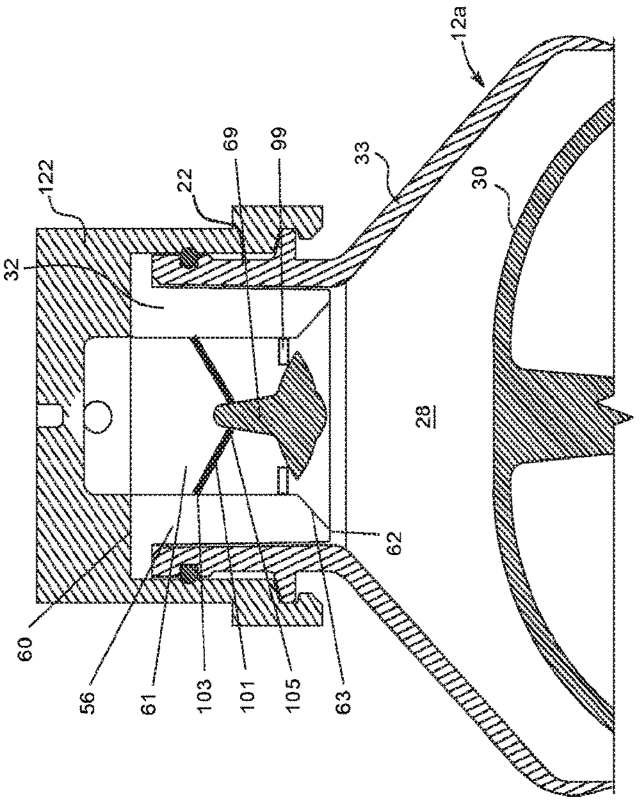
FIG. 34A is a side cross-sectional view of a syringe and a fill adapter in accordance with another example of the present disclosure, showing a flow controller in a closed position.

With reference to FIG. 34A-34B, a fill adapter 32 is illustrated in accordance with another example of the present disclosure. The fill adapter 32 is configured to facilitate transfer of liquid from a second liquid container, such as a bottle or a bag (not shown), to a first liquid container, such as a syringe 12*a*. The components of the fill adapter 32 shown in FIG. 34 are substantially similar to the components of the fill adapter 32 described herein with reference to FIGS. 30A-31B except where noted. As the previous discussion regarding the fill adapter 32 generally shown in FIGS. 30A-31B is applicable to the example shown in FIG. 34, only the relative differences between the two fill adapters 32 are discussed herein.

The fill adapter 32 is dimensioned such that it fits snuggly within the open distal end of the syringe neck 22, such as due to engagement of an outer sidewall of the fill adapter 32 with an inner sidewall of the syringe neck 22. A body 56 of the fill adapter 32 has a central bore 61 extending along a longitudinal axis. The central bore 61 is configured for allowing liquid communication between the second liquid container and the interior of the syringe 12*a*. The bore 61 has an angled portion 63 that widens in a direction from a distal end 60 to a proximal end 62 of the body 56. A sealing lip 99 may protrude radially inward from an inner surface of the central bore 61. The sealing lip 99 may be positioned distally of the angled portion 63. Desirably, the sealing lip 99 is continuous in a circumferential direction of the central bore 61. In some examples, the sealing lip 99 may be made from the same or different material as the body 56. For example, the sealing lip 99 may be made from a flexible elastomeric material, while the body 56 is made from a rigid plastic material.

The fill adapter 32 has a flow controller 69 disposed within the central bore 61. The flow controller 69 may be positioned at the proximal end 62 and is connected to an inner surface of the central bore 61 by one or more resiliently elastic elements 101. Each of the resiliently elastic elements 101 has a first end 103 connected to the body 56 of the fill adapter 32 and a second end 105 connected to the flow controller 69. The flow controller 69 is movable axially in a direction of the longitudinal axis due to liquid flow in a direction from the distal end 60 to the proximal end 62. The resiliently elastic elements 101 bias the flow controller 69 against the sealing lip 99 when no liquid flow is present. In this manner, the flow controller 69 and the sealing lip 99 define a seal to prevent liquid from dripping between the flow controller 69 and the sealing lip 99. Thus, the fill adapter 32 may be removed from the syringe 12*a* without spilling any liquid that may remain in the fill adapter 32. In some examples, the fill adapter 32 may be removably or non-removably connected to a cap 122 such that removal of the cap 122 from the syringe 12*a* also removes the fill adapter 32.

During a vacuum filling procedure, such as when an end wall 30 of the syringe 12*a* is retracted in a proximal direction by a drive member of a liquid injector (not shown), vacuum generated within an interior volume 28 of the syringe 12*a* pulls the flow controller 69 in the proximal direction against the restoring force of the resiliently elastic elements 101. In other examples, liquid pressure due to a head height of liquid in the second container once the fill adapter 32 is connected to the second container will push the flow controller 69 in the proximal direction in the direction of arrow A in FIG. 34B against the restoring force of the resiliently elastic elements 101. Movement of the flow controller 69 in the proximal direction unseats it from the sealing lip 99, thereby opening a gap 79 between the inner circumference of the sealing lip 99 and an outer circumference of the flow controller 69, such as shown in FIG. 34B. The flow controller 69 may have a curved distal surface that is configured to divert liquid flowing onto the flow controller 69 in a radially outward direction toward the gap 79. In this manner, liquid can flow into the interior volume 28 of the syringe 12*a* through the gap 79. As described herein, due to the characteristics of the Coandă effect, liquid will be attracted to the angled surface of the angled portion 63 of the fill adapter 32 and will continue flowing down the inner sidewall of the syringe 12*a*. This flow along the inside surface of the syringe 12*a* helps to reduce turbulence as the liquid fills the syringe 12*a*, which aides in reducing air bubbles from forming as the syringe 12*a* is filled.

Proximal movement of the flow controller 69 in the direction of arrow A in FIG. 34B can be a function of the head pressure of the liquid in the second container, or the vacuum generated by a drive member of the liquid injector pulling the end wall 30 of the syringe 12*a* (or a plunger 31 of the syringe 12*b* in FIG. 2B) in the proximal direction, against the restoring force of the resiliently elastic members 101 acting in the distal direction. In this manner, the size of the gap 79 can be controlled to widen or narrow the gap 79 in order to optimize liquid flow due to the characteristics of the Coandă effect.

While several examples of syringes, adapters, and systems and methods of connection for use in medical liquid delivery systems are shown in the accompanying figures and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

What is claimed is:

1. A fill adapter for delivery of a medical liquid to a syringe, the fill adapter comprising:
- a body having a distal end, a proximal end, and a central bore extending between the distal end and the proximal end along a longitudinal axis, the central bore having an angled portion at the proximal end of the body such that a diameter of the central portion increases at the angled portion in a direction from the distal end toward the proximal end; and
- a flow controller disposed within the central bore and having a convex curved distal surface, wherein the flow controller defines a gap formed between an outer surface of the convex curved distal surface of the flow controller and an inner surface of the central bore,
- wherein the convex curved distal surface of the flow controller is shaped to direct liquid flowing through the central bore to flow through the gap, along the angled portion, and along an interior surface of a sidewall of the syringe under a Coandă effect.

2. The fill adapter of claim 1, wherein at least a portion of the flow controller is connected to the inner surface of the central bore by one or more spokes having a first end connected to the inner surface of the central bore and a second end connected to the flow controller.

3. The fill adapter of claim 2, wherein each of the one or more spokes is resiliently elastic such that the flow controller is movable in a direction of the longitudinal axis of the body with the flow of the liquid.

4. The fill adapter of claim 1, wherein the curved distal surface has a flow diverter extending distally from a central portion of the curved distal surface, the flow diverter shaped to direct liquid flowing through the central bore in a radially outward direction toward the gap.

5. The fill adapter of claim 1, wherein the flow controller has a curved proximal surface.

6. The fill adapter of claim 5, wherein the curved proximal surface of the flow controller is convex.

7. The fill adapter of claim 1, wherein the body has a flange at the distal end, the flange extending radially outward relative to an outer surface of the body.

8. The fill adapter of claim 1, wherein at least a portion of the body is configured to be removably received within an open distal end of the syringe.

9. A fluid transfer assembly comprising:
- a syringe for receiving a medical liquid therein, the syringe comprising:
  - a proximal end, a conical distal end having an open-ended syringe neck, and a sidewall extending between the proximal end and the distal end along a longitudinal axis, the syringe defining an interior volume for receiving the medical liquid therein; and
- a fill adapter received within the open-ended syringe neck, the fill adapter comprising:
  - a body having a distal end, a proximal end, and a central bore extending between the distal end and the proximal end along a longitudinal axis, the central bore having an angled portion at the proximal end of the body such that a diameter of the central portion increases at the angled portion in a direction from the distal end toward the proximal end; and a flow controller disposed within the central bore and having a convex curved distal surface, wherein the flow controller defines a gap formed between an outer surface of the convex curved distal surface of the flow controller and an inner surface of the central bore, wherein the convex curved distal surface of the flow controller is shaped to direct liquid flowing through the central bore to flow through the gap, along the angled portion, and along an interior surface of the conical distal end of the syringe and along the sidewall of the syringe under a Coandă effect.

10. The fluid transfer assembly of claim 9, wherein an outer portion of the syringe neck has a flange extending around at least a portion of a circumference of the syringe neck.

11. The fluid transfer assembly of claim 10, wherein at least a portion of the flange is configured to engage a cap for enclosing the open-ended syringe neck at the distal end of the syringe.

12. The fluid transfer assembly of claim 9, wherein the syringe has a drive member engagement portion protruding proximally from an end wall enclosing the proximal end and configured for engagement with a drive member of a fluid injector.

13. The fluid transfer assembly of claim 9, wherein the sidewall of the syringe is flexible and rolls upon itself when the syringe is acted upon by a drive member of a fluid injector such that an outer surface of the sidewall is folded in a radially inward direction as the drive member is advanced from the proximal end to the distal end, and wherein the outer surface of the sidewall is unfolded in a radially outward direction as the drive member is retracted from the distal end to the proximal end.

14. The fluid transfer assembly of claim 9, wherein at least a portion of the flow controller is connected to the inner surface of the central bore by one or more spokes, and wherein each of the one or more spokes has a first end connected to the inner surface of the central bore and a second end connected to the flow controller.

15. A fluid transfer assembly comprising:

a syringe for receiving a medical liquid therein, the syringe comprising:

a proximal end, a distal end having an open-ended syringe neck, and a sidewall extending between the proximal end and the distal end along a longitudinal axis, the syringe defining an interior volume for receiving the medical liquid therein;

a fill adapter received within the open-ended syringe neck, the fill adapter comprising:

a body having a distal end, a proximal end, and a central bore extending between the distal end and the proximal end along a longitudinal axis, the central bore having an angled portion at the proximal end of the body such that a diameter of the central portion increases at the angled portion in a direction from the distal end toward the proximal end; and a flow controller disposed within the central bore such that a gap is formed between an outer surface of the flow controller and an inner surface of the central bore; and a cap secured to the syringe neck, the cap having a nozzle in liquid communication with the interior volume of the rolling diaphragm syringe, wherein the flow controller is shaped to direct liquid flowing through the central bore to flow through the gap, along the angled portion, and along an interior surface of the sidewall of the syringe under a Coandă effect.

16. The fluid transfer assembly of claim 15, wherein an outer portion of the syringe neck has a flange extending around at least a portion of a circumference of the syringe neck, and wherein the cap has one or more tabs configured to releasably engage at least a portion of the flange.

17. The fluid transfer assembly of claim 16, wherein the one or more tabs has a first end connected to the cap and a second end extending proximally from the first end, and wherein the second end is deflectable in a radially outward direction when the cap contacts the flange on the syringe neck.

* * * * *